(12) United States Patent
Ito et al.

(10) Patent No.: US 8,293,748 B2
(45) Date of Patent: *Oct. 23, 2012

(54) P38 MAP KINASE INHIBITORS

(75) Inventors: Kazuhiro Ito, London (GB); Peter Strong, London (GB); William Garth Rapeport, London (GB); Peter John Murray, London (GB); John King-Underwood, Pendock (GB); Jonathan Gareth Williams, Nottingham (GB); Stuart Thomas Onions, Nottingham (GB); Simon Christopher Hirst, Nottingham (GB); David Michel Adrien Taddei, Nottingham (GB); Catherine Elisabeth Charron, London (GB)

(73) Assignee: Respivert Ltd. (GB)

( * ) Notice: Subject to any disclaimer, the term of this patent is extended or adjusted under 35 U.S.C. 154(b) by 0 days.

This patent is subject to a terminal disclaimer.

(21) Appl. No.: 13/121,999

(22) PCT Filed: Oct. 2, 2009

(86) PCT No.: PCT/GB2009/051304
§ 371 (c)(1),
(2), (4) Date: Mar. 31, 2011

(87) PCT Pub. No.: WO2010/038086
PCT Pub. Date: Apr. 8, 2010

(65) Prior Publication Data
US 2011/0212962 A1    Sep. 1, 2011

(30) Foreign Application Priority Data
Oct. 2, 2008 (GB) .................................. 0818033.3
Dec. 11, 2008 (GB) .................................. 0822609.4

(51) Int. Cl.
| A61K 31/496 | (2006.01) |
| A61K 31/505 | (2006.01) |
| A61K 31/4427 | (2006.01) |
| C07D 403/02 | (2006.01) |
| C07D 403/14 | (2006.01) |
| C07D 401/02 | (2006.01) |
| C07D 401/14 | (2006.01) |

(52) U.S. Cl. ................... 514/253.09; 514/269; 514/340; 544/333; 544/364; 546/275.4

(58) Field of Classification Search ............ 514/253.09, 514/269, 340; 544/333, 364; 546/274.5
See application file for complete search history.

(56) References Cited

U.S. PATENT DOCUMENTS

| 6,525,046 B1 | 2/2003 | Cirillo et al. |
| 6,916,814 B2 | 7/2005 | Moss et al. |
| 7,329,670 B1 | 2/2008 | Dumas et al. |
| 7,625,915 B2 | 12/2009 | Dumas et al. |
| 2004/0180906 A1 | 9/2004 | Flynn et al. |
| 2004/0192653 A1 | 9/2004 | Munson et al. |
| 2007/0010529 A1 | 1/2007 | Takahashi et al. |
| 2008/0113967 A1 | 5/2008 | Flynn et al. |
| 2008/0207699 A1 | 8/2008 | Hoelzemann et al. |
| 2008/0300281 A1 | 12/2008 | Dumas et al. |

FOREIGN PATENT DOCUMENTS

| DE | 102005015253 | 10/2006 |
| WO | WO 99-23091 | 5/1999 |
| WO | WO 99/32110 | 7/1999 |
| WO | WO 99/32111 | 7/1999 |
| WO | WO 99/32455 | 7/1999 |
| WO | WO 99/47529 | 9/1999 |
| WO | WO 00/43384 | 7/2000 |
| WO | WO 01/04115 | 1/2001 |
| WO | WO 02/066442 | 8/2002 |
| WO | WO 02/092576 | 11/2002 |
| WO | WO 03/005999 | 1/2003 |
| WO | WO 03/068228 | 8/2003 |
| WO | WO 03/072569 | 9/2003 |
| WO | WO 03/084503 | 10/2003 |
| WO | WO 2004/014387 | 2/2004 |
| WO | WO 2004/021988 | 3/2004 |
| WO | WO 2004/060306 | 7/2004 |
| WO | WO 2004/078746 | 9/2004 |
| WO | WO 2004/089929 | 10/2004 |

(Continued)

OTHER PUBLICATIONS

Friedenreich, Christine M. State of the epidemiological evidence on physical activity and cancer prevention. European Journal of Cancer, 46, (2010), 2593-2604.*
U.S. Appl. No. 13/121,445, filed Mar. 29, 2011, Ito et al.
U.S. Appl. No. 13/133,998, filed Aug. 9, 2011, Ito et al.
U.S. Appl. No. 13/139,010, filed Aug. 9, 2011, Ito et al.
U.S. Appl. No. 13/262,266, filed Sep. 30, 2011, Ito et al.
Dumas et al., "Synthesis and Pharmacological Characterization of a Potent, Orally Active p38 Kinase Inhibitor", Bioorganic & Medicinal Chemistry Letters 12 (2002) 1559-1562.
International Search Report, PCT/GB2009/051304, Apr. 15, 2010.

Primary Examiner — Joseph K. McKane
Assistant Examiner — Samantha Shterengarts
(74) Attorney, Agent, or Firm — Mary A. Appollina

(57) ABSTRACT

There are provided inter alia compounds of formula (I)

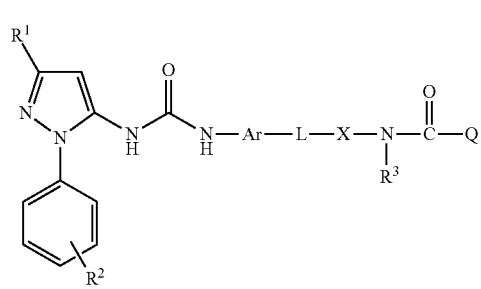

wherein $R^1$, Ar, L, X, $R^3$ and Q are as defined in the specification for use in therapy, especially in the treatment of inflammatory diseases.

19 Claims, 1 Drawing Sheet

FOREIGN PATENT DOCUMENTS

| | | |
|---|---|---|
| WO | WO 2004/100946 | 11/2004 |
| WO | WO 2005/018624 | 3/2005 |
| WO | WO 2005/048948 | 6/2005 |
| WO | WO 2005/110994 | 11/2005 |
| WO | WO 2005/113511 | 12/2005 |
| WO | WO 2006/009741 | 1/2006 |
| WO | WO 2006/014290 | 2/2006 |
| WO | WO 2006/015775 | 2/2006 |
| WO | WO 2006/028524 | 3/2006 |
| WO | WO 2006/043090 | 4/2006 |
| WO | WO 2006/062984 | 6/2006 |
| WO | WO 2006/068591 | 6/2006 |
| WO | WO 2006/072589 | 7/2006 |
| WO | WO 2006/081034 | 8/2006 |
| WO | WO 2007/002635 | 1/2007 |
| WO | WO 2007/017083 | 2/2007 |
| WO | WO 2007/038425 | 4/2007 |
| WO | WO 2007/059202 | 5/2007 |
| WO | WO 2007/064872 | 6/2007 |
| WO | WO 2008/016192 | 2/2008 |

\* cited by examiner

FIGURE 1. The Effect of compound Example 1 on LPS-induced neutrophil accumulation in BAL
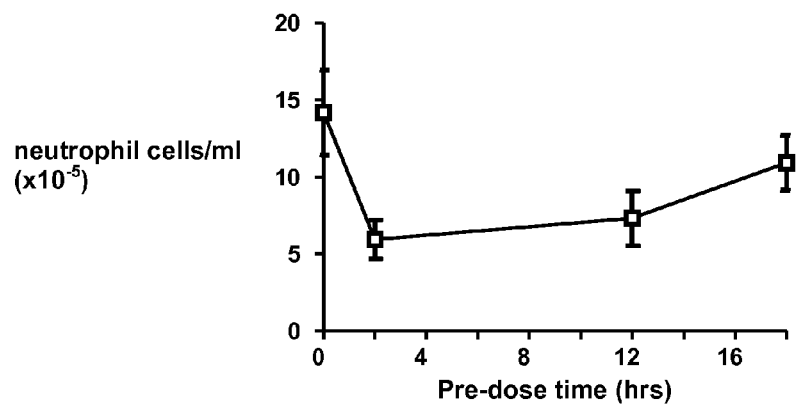
FIGURE 2. The effect of compound Example 1 on LPS-induced neutrophil accumulation in BAL
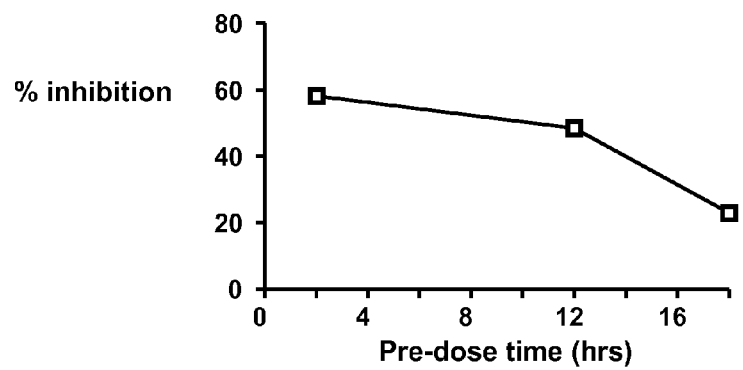

P38 MAP KINASE INHIBITORS

This application is a National Stage application under 35 U.S.C. 371 of PCT International Application No. PCT/GB2009/051304, filed Oct. 2, 2009, which claims priority from Patent Application No. GB 0818033.3, filed Oct. 2, 2008 and GB 0822609.4, filed Dec. 11, 2008, the contents of which are hereby incorporated by reference.

FIELD OF THE INVENTION

The invention relates to compounds which are inhibitors of p38 mitogen-activated protein kinase enzymes (referred to herein as p38 MAP kinase inhibitors), particularly the alpha and gamma kinase sub-types thereof, and their use in therapy, including in pharmaceutical combinations, especially in the treatment of inflammatory diseases, including inflammatory diseases of the lung, such as COPD.

BACKGROUND OF THE INVENTION

Four p38 MAPK isoforms (alpha, beta, gamma and delta respectively) have been identified, each displaying a tissue-specific expression pattern. The p38 MAPK alpha and beta isoforms are ubiquitously expressed throughout the body and are found in many different cell types. The p38 MAPK alpha and beta isoforms are inhibited by certain known small molecule p38 MAPK inhibitors. Earlier generations of compounds were highly toxic due to the ubiquitous expression pattern of these isoforms and off-target effects of the compounds. More recent inhibitors are improved to be highly selective for p38 MAPK alpha and beta isoforms and have a wider safety margin.

Less is known about the p38 MAPK gamma and delta isoforms. These isoforms are expressed in specific tissues/cells (unlike the p38 alpha and p38 beta isoforms). The p38 MAPK-delta isoform is expressed more in the pancreas, testes, lung, small intestine and kidney. It is also abundant in macrophages (Smith, S. J. (2006) *Br. J. Pharmacol.* 149:393-404) and detectable in neutrophils, CD4+ T cells and endothelial cells (www.genecard.org, Karin, K. (1999) *J. Immunol.*). Very little is known about the expression of p38 MAPK gamma but it is expressed more in brain and heart, as well as in lymphocytes and macrophages (www.genecard.org).

Selective small molecule inhibitors of p38 MAPK-gamma and -delta are not currently available, but one existing compound, BIRB 796, is known to have pan-isoform inhibitory activity. The p38 gamma and p38 delta inhibition is observed at higher concentrations of the compound than those required to inhibit p38 alpha and p38 beta (Kuma, Y. (2005) *J. Biol. Chem.* 280:19472-19479). BIRB 796 also impaired the phosphorylation of p38 MAPKs or JNKs by the upstream kinase MKK6 or MKK4. Kuma discussed the possibility that the conformational change caused by the binding of the inhibitor to the MAPK may affect the structure of both its phosphorylation site and the docking site for the upstream activator, therefore impairing the phosphorylation of p38 MAPKs or JNKs.

p38 MAP kinase is believed to play a pivotal role in many of the signalling pathways that are involved in initiating and maintaining chronic, persistent inflammation in human disease, for example, severe asthma and COPD. There is now an abundant literature which demonstrates that p38 MAP kinase is activated by a range of pro-inflammatory cytokines and that its activation results in the recruitment and release of further pro-inflammatory cytokines. Indeed, data from some clinical studies demonstrate beneficial changes in disease activity in patients during treatment with p38 MAP kinase inhibitors. For instance Smith, S. J. (2006) *Br. J. Pharmacol.* 149:393-404 describes the inhibitory effect of p38 MAP kinase inhibitors on cytokine release from human macrophages. Use of inhibitors of p38 MAP kinase in the treatment of chronic obstructive pulmonary disease (COPD) is proposed. Small molecule inhibitors targeted to p38 MAPKα/β have proved to be effective in reducing various parameters of inflammation in cells and tissues obtained from patients with COPD, who are generally corticosteroid insensitive, (Smith, S. J. (2006) *Br. J. Pharmacol.* 149:393-404) and in vivo animal models (Underwood, D. C. et al. (2000) 279:895-902; Nath, P. et al. (2006) *Eur. J. Pharmacol.* 544:160-167). Irusen and colleagues also suggested the possibility of involvement of p38 MAPKα/β on corticosteroid insensitivity via reduction of binding affinity of glucocorticoid receptor (GR) in nuclei (Irusen, E. et al., (2002) *J. Allergy Clin. Immunol.*, 109:649-657). Clinical experience with a range of p38 MAP kinase inhibitors, including AMG548, BIRB 796, VX702, SCIO469 and SCIO323 is described in Lee et al. (2005) *Current Med. Chem.* 12:2979-2994.

COPD is a condition in which the underlying inflammation has been reported to be substantially resistant to the anti-inflammatory effects of inhaled corticosteroids. Consequently, an effective strategy for treating COPD may well be to develop an intervention which both has inherent anti-inflammatory effects and is able to increase the sensitivity of lung tissues from COPD patients to inhaled corticosteroids. The recent publication of Mercado et al (2007; *American Thoracic Society Abstract* A56) demonstrates that silencing p38 gamma has the potential to restore sensitivity to corticosteroids. Thus there may be a "two pronged" benefit to the use of a p38 MAP kinase inhibitor for the treatment of COPD.

However, the major obstacle hindering the utility of p38 MAP kinase inhibitors in the treatment of human chronic inflammatory diseases has been the toxicity observed in patients. This has been sufficiently severe to result in the withdrawal from clinical development of many of the compounds progressed, including all those specially mentioned above.

There remains a need to identify and develop new compounds therapeutically useful as p38 MAP kinase inhibitors which have improved therapeutic potential, in particular which are more efficacious, longer acting and/or less toxic at the relevant therapeutic dose. An objective of the present invention is to provide compounds which inhibit p38 MAP kinase with certain sub-type specificity, which show good anti-inflammatory potential.

SUMMARY OF THE INVENTION

According to the invention, there is provided a compound of formula (I)

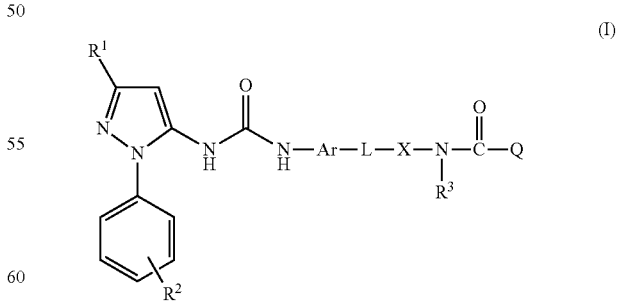

(I)

wherein $R^1$ is $C_{1-6}$ alkyl optionally substituted by a hydroxyl group;
$R^2$ is H or $C_{1-6}$ alkyl optionally substituted by a hydroxyl group;
$R^3$ is H, $C_{1-6}$ alkyl or $C_{0-3}$ alkyl$C_{3-6}$ cycloalkyl Ar is a naphthyl or a phenyl ring either of which may be optionally substituted by one or more groups independently selected from $C_{1-6}$ alkyl, $C_{1-6}$ alkoxy, amino, $C_{1-4}$ mono or di-alkyl amino;

L is a saturated or unsaturated branched or unbranched $C_{1-8}$ alkylene chain, wherein one or more carbons are optionally replaced by —O— and the chain is optionally substituted by one or more halogen atoms, X is 5 or 6 membered heteroaryl group containing at least one nitrogen atom and optionally including 1 or 2 further heteroatoms selected from O, S and N;

Q is selected from:
a) a saturated or unsaturated, branched or unbranched $C_{1-10}$ alkyl chain, wherein at least one carbon (for example 1, 2 or 3 carbons, suitably 1 or 2, in particular 1) is replaced by a heteroatom selected from O, N, $S(O)_p$, wherein said chain is optionally, substituted by one or more groups independently selected from oxo, halogen, an aryl group, a heteroaryl group or a heterocyclyl group, each aryl, heteroaryl or heterocyclyl group bearing 0 to 3 substituents selected from halogen, $C_{1-6}$ alkyl, $C_{1-6}$ alkoxy, $C_{1-6}$ haloalkyl, amino, $C_{1-4}$ mono or di-alkyl amino, with the proviso that the atom linked directly to the carbonyl in —$NR^3C(O)$— is not an oxygen or a sulfur atom; and b) a $C_{0-8}$ alkyl$C_{5-6}$ heterocycle said heterocyclyl group comprising at least one heteroatom (for example 1, 2 or 3, suitably 1 or 2, in particular 1 heteroatom) selected from O, N and S, and is optionally substituted by one or two or three groups independently selected from halogen, $C_{1-6}$ alkyl, $C_{1-6}$ alkoxy, $C_{1-6}$ haloalkyl, amino, $C_{1-4}$ mono and di-alkyl amino; and p is 0, 1 or 2;

or a pharmaceutically acceptable salt or solvate thereof, including all stereoisomers and tautomers thereof.

BRIEF DESCRIPTION OF THE FIGURES

FIG. 1 shows pre-dose time against neutrophil number in BALF for the compound of Example 1 in the LPS-induced neutrophil accumulation test.

FIG. 2 shows pre-dose time against % inhibition of neutrophilia for the compound of Example 1 in the LPS-induced neutrophil accumulation test.

DETAILED DESCRIPTION OF THE INVENTION

Alkyl as used herein refers to straight chain or branched chain alkyl, such as, without limitation, methyl, ethyl, propyl, iso-propyl, butyl, and tert-butyl. In one embodiment alkyl refers to straight chain alkyl.

Alkoxy as used herein refers to straight or branched chain alkoxy, for example methoxy, ethoxy, propoxy, butoxy. Alkoxy as employed herein also extends to embodiments in which the oxygen atom is located within the alkyl chain, for example —$CH_2CH_2OCH_3$ or —$CH_2OCH_3$. In one embodiment the alkoxy is linked through oxygen to the remainder of the molecule. In one embodiment the disclosure relates to straight chain alkoxy.

In one embodiment of the disclosure there is provided compounds of formula (I), wherein $R^1$ is methyl, ethyl, propyl, iso-propyl, butyl or tert-butyl, in particular tert-butyl.

In one embodiment $R^1$ is —$C(CH_3)_2CH_2OH$.

In one embodiment $R^2$ is methyl, ethyl, propyl, iso-propyl, butyl, or tert-butyl, in particular methyl.

In one embodiment $R^2$ is —$CH_2OH$.

In one embodiment $R^2$ is in the 2, 3, or 4 position (i.e. ortho, meta or para position), in particular the para (4) position.

In one embodiment Ar is napthyl.

In one embodiment Ar is not substituted with optional substituents.

In one embodiment Ar is substituted with 1 or 2 groups.

In one embodiment L is a straight chain linker, for example:
—$(CH_2)_n$— wherein n is 1, 2, 3, 4, 5, 6, 7 or 8; or
—$(CH_2)_nO(CH_2)_m$— wherein n and m are independently 0, 1, 2, 3, 4, 5, 6 or 7, with the proviso that n+m is zero or an integer from 1 to 7, for example where n is 0 and m is 1 or 2 or alternatively, for example, where n is 1 or 2 and m is 0.

In one embodiment L is a branched chain linker $R^aO(CH_2)_m$ wherein m is zero or an integer 1, 2, 3, 4 or 5 and $R^a$ is $C_{2-7}$ branched alkyl, with the proviso that the number of carbons in $R^a$+m is an integer from 2 to 7, especially where m is 0, in particular —$CH(CH_3)O$—.

In one embodiment L is a branched chain linker $(CH_2)_nOR^b$ wherein n is zero or an integer 1, 2, 3, 4 or 5 and $R^b$ is $C_{2-7}$ branched alkyl, with the proviso that the number of carbons in $R^b$+n is an integer from 2 to 7, in particular —$OCH(CH_3)$— or —$OC(CH_3)_2CH_2$—.

In one embodiment L is a branched chain linker $R^aOR^b$ wherein $R^a$ and $R^b$ are independently selected from $C_{2-7}$ branched alkylene with the proviso that the number of carbons in $R^a+R^b$ is an integer from 4 to 7.

In one embodiment $R^3$ is H.

In one embodiment $R^3$ is methyl, ethyl, propyl or iso-propyl.

Halogen includes fluoro, chloro, bromo or iodo, in particular fluoro, chloro or bromo, especially fluoro or chloro.

In one embodiment the chain L includes 1, 2 or 3 halogen atom substituents, independently selected from fluoro, chloro, and bromo, for example an alkylene carbon may bear one or two chloro or fluorine atoms and a terminal methyl group may bear one, two or three fluorine atoms or one, two or three chlorine atoms to provide a group such as trifluoromethyl or trichloromethyl.

In one embodiment X is selected from, pyrrole, oxazole, thiazole, isothiazole, imidazole, pyrazole, isoxazole, oxadiazole, pyridazine, pyrimidine, pyrazine, or 1,2,3 and 1,2,4 triazole, in particular, pyrimidine, imidazole or pyridine, and especially pyridine.

In one embodiment of the fragment Q the $C_{1-10}$ alkyl chain wherein at least one carbon (for example 1, 2 or 3 carbons, in particular 1 or 2 carbons) is replaced by a heteroatom selected from O, N, $S(O)_p$, wherein said chain is optionally, substituted by one or more groups selected from oxo, halogen, an aryl group, a heteroaryl group or an heterocyclyl group, each aryl, heteroaryl or heterocyclyl group bearing 0 to 3 substituents selected from halogen, $C_{1-6}$ alkyl, $C_{1-6}$ alkoxy, $C_{1-6}$ haloalkyl, amino, $C_{1-4}$ mono or di-alkyl amino.

In one embodiment Q is a saturated or unsaturated, branched or unbranched $C_{1-8}$ alkyl chain or $C_{1-6}$ alkyl chain, wherein at least one carbon is replaced by a heteroatom selected from —O, —N, $S(O)_p$.

In one embodiment the heteroatom(s) replacing carbon(s) in the alkyl chain fragment of Q are selected from N and O.

In one embodiment the alkyl chain fragment of Q does not bear any optional substituents.

In one embodiment the alkyl chain fragment of Q bears 1, 2, or 3, for example 1 or 2, in particular 1 optional substituent.

It will be clear to persons skilled in the art that the heteroatom may replace a primary, secondary or tertiary carbon, that is a $CH_3$, —$CH_2$— or a —CH—, group, as technically appropriate.

In one embodiment p is 0 or 2.

In one embodiment compounds of the disclosure include those in which the fragment —NR$^3$C(O)Q in formula I is represented by:

—NR$^3$C(O)CH$_2$OC$_{1-6}$ alkyl, in particular —NR$^3$C(O)CH$_2$OCH$_3$, especially —NHC(O)CH$_2$OCH$_3$;

—NR$^3$C(O)CH$_2$O(CH$_2$)$_2$OCH$_3$, in particular —NHC(O)CH$_2$O(CH$_2$)$_2$OCH$_3$;

—NR$^3$C(O)CH(CH$_3$)OCH$_3$ in particular —NHC(O)CH(CH$_3$)OCH$_3$;

—NR$^3$C(O)CH$_2$NHCH$_3$ in particular —NHC(O)CH$_2$NHCH$_3$;

—NR$^3$C(O)CH$_2$NHCH$_2$CH$_2$OCH$_3$ in particular —NHC(O)CH$_2$NH(CH$_2$)$_2$OCH$_3$;

—NR$^3$C(O)CH$_2$SCH$_3$, in particular —NHC(O)CH$_2$SCH$_3$;

—NR$^3$C(O)CH$_2$S(O)$_2$CH$_3$, in particular —NHC(O)CH$_2$S(O)$_2$CH$_3$;

—NR$^3$C(O)NH$_2$ in particular —NHC(O)NH$_2$;

—NR$^3$C(O)NHC$_{1-7}$ alkyl, in particular —NHC(O)NHCH$_3$

—NR$^3$C(O)N(C$_{1-4}$ alkyl)C$_{1-5}$ alkyl in particular —NHC(O)N(CH$_3$)$_2$; or —NR$^3$C(O)CHN[(CH$_2$)$_2$OCH$_3$]$_2$ in particular —NHC(O)CHN[(CH$_2$)$_2$OCH$_3$]$_2$ Thus in one embodiment a nitrogen atom in the alkyl chain is directly bonded to the carbonyl of the fragment —NR$^3$C(O) and additionally may, for example, be a terminal amino group, suitably —NR$^3$C(O)N(CH$_3$)$_2$ or —NR$^3$C(O)NHCH$_3$.

In one embodiment Q is a saturated or unsaturated, branched or unbranched C$_{1-10}$ alkyl chain, wherein at least one carbon is replaced by a heteroatom selected from O, N, and S(O)$_p$, wherein said chain is substituted by an aryl group bearing 0 to 3 substituents, for example 1, 2 or 3, such as 1 or 2 substituents independently selected from halogen, C$_{1-6}$ alkyl, C$_{1-6}$ alkoxy, C$_{1-6}$ haloalkyl, amino and C$_{1-4}$ mono or di alkyl amino. In one embodiment the said aryl group is phenyl, for example substituted phenyl or unsubstituted phenyl.

Examples of the fragment —NR$^3$C(O)Q wherein Q comprises substituted phenyl include: —NR$^3$C(O)CH$_2$NHCH$_2$C$_6$H$_5$(OCH$_3$) and —NR$^3$C(O)CH$_2$N(CH$_3$)CH$_2$C$_6$H$_5$(OCH$_3$).

In one embodiment Q is a saturated or unsaturated, branched or unbranched C$_{1-10}$ alkyl chain, wherein at least one carbon is replaced by a heteroatom selected from O, N, and S(O)$_p$, wherein said chain is substituted by a heteroaryl group bearing 0 to 3 substituents for example 1, 2 or 3, such as 1 or 2 substituents selected from halogen, C$_{1-6}$ alkyl, C$_{1-6}$ alkoxy, C$_{1-6}$ alkyl amino, C$_{1-4}$ mono or di alkyl amino. In one embodiment the said heteroaryl group is selected from, thiophene, oxazole, thiazole, isothiazole, imidazole, pyrazole, isoxazole, isothiazole, oxadiazole, 1,2,3 or 1,2,4 triazole, pyridine, pyridazine, pyrimidine, pyrazine and, in particular pyridine and pyrimidine, especially pyridine.

In one embodiment Q is a saturated or unsaturated, branched or unbranched C$_{1-10}$ alkyl chain, wherein at least one carbon is replaced by a heteroatom selected from O, N and S(O)$_p$ wherein said chain is substituted by a heterocyclyl group bearing 0 to 3 substituents, for example 1, 2 or 3, such as 1 or 2 substituents selected from halogen, C$_{1-6}$ alkyl, C$_{1-6}$ alkoxy, C$_{1-6}$ haloalkyl amino, C$_{1-4}$ mono or di alkyl amino.

In one embodiment said heterocyclyl is selected, from a 5 or 6 membered saturated or partially unsaturated ring system comprising one or more (for example 1, 2 or 3 suitably 1 or 2, in particular 1) heteroatoms independently selected from O, N and S, for example pyrrolidine, tetrahydrofuran, tetrahydrothiophene, piperidine, piperazine, morpholine, and 1,4-dioxane.

In one embodiment compounds of the disclosure include compounds of formula (I) in which the fragment —NR$^3$C(O)C$_{0-8}$alkylheterocyclyl is represented by:

—NHC(O)-(tetrahydropyranyl), such as —NHC(O)-(tetrahydro-2H-pyran-4-yl),

—NHC(O)-(morpholinyl) such as —NHC(O)-(4-morpholinyl),

—NHC(O)-(pyrrolidinyl), such as —NHC(O)-(pyrrolidin-1-yl),

—NHC(O)-(piperazinyl), such as —NHC(O)-(piperazin-1-yl),

—NHC(O)-(methylpiperazinyl), such as —NHC(O)-(4-methylpiperazin-1-yl),

—NHC(O)-[(methoxyethyl)piperazinyl], such as —NHC(O)-[4-(2-methoxyethyl)piperazin-1-yl], —NHC(O)CH$_2$-(tetrahydropyranyl), such as —NHC(O)CH$_2$-(tetrahydro-2H-pyran-4-yl)

—NHC(O)CH$_2$-(morpholinyl), such as —NHC(O)CH$_2$-(4-morpholinyl),

—NHC(O)CH$_2$— (pyrrolidinyl), such as —NHC(O)CH$_2$-(pyrrolidin-1-yl),

—NHC(O)CH$_2$— (piperazinyl), such as —NHC(O)CH$_2$-(piperazin-1-yl), and

NHC(O)CH$_2$-(methylpiperazinyl), such as —NHC(O)CH$_2$-(4-methylpiperazin-1-yl).

—NHC(O)CH$_2$-[(methoxyethyl)piperazinyl], such as —NHC(O)CH$_2$-[4-(2-methoxyethyl)piperazin-1-yl].

In one embodiment of the fragment Q, the saturated or unsaturated, branched or unbranched C$_{1-10}$ alkyl chain, wherein at least one carbon is replaced by a heteroatom selected from —O, —N, S(O)$_p$ is selected from: —CH$_2$OCH$_2$—, —CH$_2$NHCH$_2$—, —CH$_2$NH— and —CH$_2$OCH$_2$CH$_2$—. These fragments may optionally terminate in an aryl group, a heteroaryl group or a heterocyclyl group as defined for fragment Q above.

In one embodiment the disclosure relates to compounds of formula (IA)

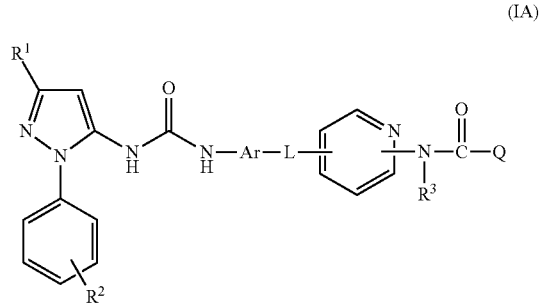

(IA)

wherein R$^1$, R$^2$, Ar, L, R$^3$ and Q are as defined above.

In a further embodiment the disclosure relates to compounds of formula (IB)

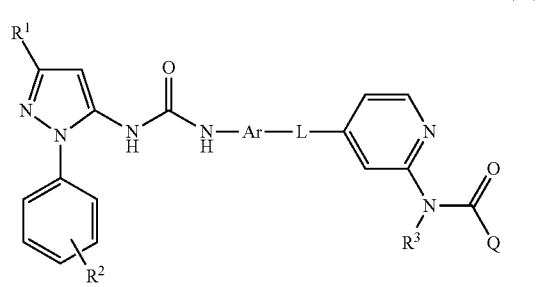

(IB)

wherein R$^1$, R$^2$, Ar, L, R$^3$ and Q are as defined above.

In yet another embodiment the disclosure relates to compounds of formula (IC)

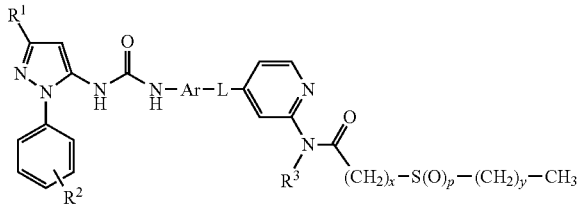

(IC)

wherein $R^1$, $R^2$, Ar, L and $R^3$ are as defined above and p is 0, 1 or 2, in particular 0 or 2, especially 0, and x is an integer from 1 to 6 (including 2, 3, 4 and 5) and y is zero or an integer from 1 to 5 (including 2, 3 and 4) with proviso that x+y is an integer from 1 to 6, for example x is 1 and y is 1.

In one embodiment the disclosure relates to compounds of formula (ID)

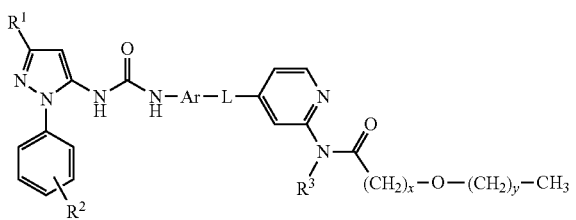

(ID)

wherein $R^1$, $R^2$, Ar, L and $R^3$ are as defined above
x is an integer from 1 to 6 (including 2, 3, 4 and 5) and y is zero or an integer from 1 to 5 (including 2, 3 and 4),
with the proviso that x+y is an integer from 1 to 6, for example x is 1 and y is 0.

In one embodiment of the compounds of formula (ID) the fragment —$NR^3C(O)(CH_2)_xO(CH_2)_yCH_3$ is: —$NR^3C(O)CH_2OCH_3$, especially —$NHC(O)CH_2OCH_3$ In one embodiment the compound is not: N-(4-((4-(3-(3-tert-Butyl-1-p-tolyl-1H-pyrazol-5-yl)ureido)naphthalen-1-yloxy)methyl)pyridin-2-yl)-2-methoxyacetamide.

In one embodiment the compound is:
N-(4-((4-(3-(3-tert-Butyl-1-p-tolyl-1H-pyrazol-5-yl)ureido)naphthalen-1-yloxy)methyl)pyridin-2-yl)-2-methoxyacetamide;
Methyl 4-((4-(3-(3-tert-butyl-1-p-tolyl-1H-pyrazol-5-yl)ureido)naphthalen-1-yloxy)methyl)pyridin-2-ylurea;
N-(4-((4-(3-(3-tert-Butyl-1-p-tolyl-1H-pyrazol-5-yl)ureido)naphthalen-1-yloxy)methyl)pyridin-2-yl)tetrahydro-2H-pyran-4-carboxamide;
(S)—N-(4-((4-(3-(3-tert-Butyl-1-p-tolyl-1H-pyrazol-5-yl)ureido)naphthalen-1-yloxy)methyl)pyridin-2-yl)-2-methoxypropanamide;
(R)—N-(4-((4-(3-(3-tert-Butyl-1-p-tolyl-1H-pyrazol-5-yl)ureido)naphthalen-1-yloxy)methyl)pyridin-2-yl)-2-methoxypropanamide;
N-(4-((4-(3-(3-tert-Butyl-1-p-tolyl-1H-pyrazol-5-yl)ureido)naphthalen-1-yloxy)methyl)pyridin-2-yl)-2-(methylthio)acetamide;
N-(4-((4-(3-(3-tert-Butyl-1-p-tolyl-1H-pyrazol-5-yl)ureido)naphthalen-1-yloxy)methyl)pyridin-2-yl)-2-morpholinoacetamide;
N-(4-((4-(3-(3-tert-Butyl-1-p-tolyl-1H-pyrazol-5-yl)ureido)naphthalen-1-yloxy)methyl)pyridin-2-yl)-2-(pyrrolidin-1-yl)acetamide;
N-(4-((4-(3-(3-tert-Butyl-1-p-tolyl-1H-pyrazol-5-yl)ureido)naphthalen-1-yloxy)methyl)pyridin-2-yl)-2-(4-methylpiperazin-1-yl)acetamide;
N-(4-((4-(3-(3-tert-Butyl-1-p-tolyl-1H-pyrazol-5-yl)ureido)naphthalen-1-yloxy)methyl)pyridin-2-yl)-2-(4-(2-methoxyethyl)piperazin-1-yl)acetamide;
N-(4-((4-(3-(3-tert-Butyl-1-p-tolyl-1H-pyrazol-5-yl)ureido)naphthalen-1-yloxy)methyl)pyridin-2-yl)-2-(2-methoxyethylamino)acetamide;
N-(4-((4-(3-(3-tert-Butyl-1-p-tolyl-1H-pyrazol-5-yl)ureido)naphthalen-1-yloxy)methyl)pyridin-2-yl)-2-(dimethylamino)acetamide;
N-(4-((4-(3-(3-tert-Butyl-1-p-tolyl-1H-pyrazol-5-yl)ureido)naphthalen-1-yloxy)methyl)pyridin-2-yl)-2-(methylamino)acetamide;
N-(4-((4-(3-(3-tert-Butyl-1-p-tolyl-1H-pyrazol-5-yl)ureido)naphthalen-1-yloxy)methyl)pyridin-2-yl)-2-((4-methoxybenzyl)(methyl)amino)acetamide;
1-(4-((3-Methylureidopyridin-4-yl)methoxy)naphthalen-1-yl)-3-(3-tert-butyl-1-p-tolyl-1H-pyrazol-5-yl)urea;
N-(4-((4-(3-(3-tert-Butyl-1-p-tolyl-1H-pyrazol-5-yl)ureido)naphthalen-1-yloxy)methyl)pyridin-3-yl)-2-methoxyacetamide;
N-(4-((4-(3-(3-tert-Butyl-1-p-tolyl-1H-pyrazol-5-yl)ureido)naphthalen-1-yloxy)methyl)pyridin-3-yl)-2-(2-methoxyethoxy)acetamide;
N-(4-(2-(4-(3-(3-tert-Butyl-1-p-tolyl-1H-pyrazol-5-yl)ureido)naphthalen-1-yloxy)ethyl)pyridin-2-yl)-2-methoxyacetamide;
N-(4-(2-(4-(3-(3-tert-Butyl-1-p-tolyl-1H-pyrazol-5-yl)ureido)naphthalen-1-yloxy)ethyl)pyridin-2-yl)-2-(2-methoxyethoxy)acetamide;
4-(2-(4-(3-(3-tert-Butyl-1-p-tolyl-1H-pyrazol-5-yl)ureido)naphthalen-1-yloxy)ethyl)-1-methyl-3-(pyridin-2-yl)urea;
4-(2-(4-(3-(3-tert-Butyl-1-p-tolyl-1H-pyrazol-5-yl)ureido)naphthalen-1-yloxy)ethyl)-3-(pyridin-2-yl)urea;
N-(4-(2-(4-(3-(3-tert-Butyl-1-p-tolyl-1H-pyrazol-5-yl)ureido)naphthalen-1-yloxy)ethyl)pyridin-3-yl)-2-(2-methoxyethoxy)acetamide;
N-(4-((4-(3-(3-tert-Butyl-1-p-tolyl-1H-pyrazol-5-yl)ureido)naphthalen-1-yloxy)methyl)pyrimidin-2-yl)-2-methoxyacetamide; or
N-(1-(2-(4-(3-(3-tert-butyl-1-p-tolyl-1H-pyrazol-5-yl)ureido)naphthalen-1-yloxy)ethyl)-1H-imidazol-4-yl)-2-methoxy acetamide.

Examples of salts of compound (I) include all pharmaceutically acceptable salts, such as, without limitation, acid addition salts of strong mineral acids such as HCl and HBr salts and addition salts of strong organic acids such as a methansulfonic acid salt.

Examples of solvates include hydrates.

The compounds described herein may include one or more chiral centres, and the disclosure extends to include racemates, enantiomers and stereoisomers resulting therefrom. In one embodiment one enantiomeric form is present in a substantially purified form that is substantially free of the corresponding enantiomeric form.

The disclosure also extends to all polymorphic forms of the compounds herein defined.

Compounds of formula I can be prepared by a process comprising reacting compounds of formula (II):

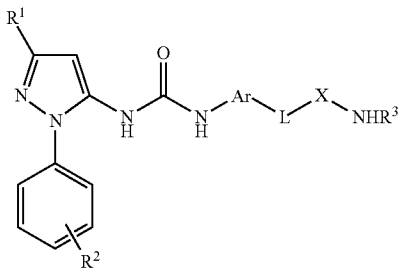
(II)

where Ar, L, X and $R^3$ are as defined above for compounds of formula (I)
with a compound of formula (III):

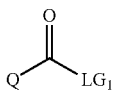
(III)

where Q is as defined above for compounds of formula (I), and $LG_1$ is a leaving group for example halogen, such as chloro.

The reaction is suitably carried out in the presence of a base (e.g. diisopropylethylamine). The reaction is suitably carried out in an aprotic solvent or solvent mixture, e.g. DCM and DMF.

Compounds of formula (II) can be prepared by reacting a compound of formula (IV)

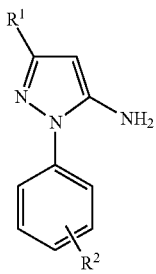
(IV)

where $R^1$ and $R^2$ are as defined above for compounds of formula (I), with a compound of formula (V):

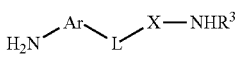
(V)

wherein Ar, L, X and $R^3$ are defined above for compounds of formula (I)
and a compound of formula (VI):

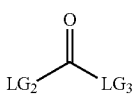
(VI)

wherein $LG_2$ and $LG_3$ each independently represent leaving groups (e.g. $LG_2$ and $LG_3$ both represent imidazolyl or halogen such as chloro).

The reaction is suitably carried out in an aprotic solvent (e.g. dichloromethane), using appropriate protecting groups for chemically sensitive groups.

A compound of formula (V) may be prepared by reduction of a compound of formula (VII)

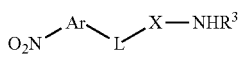
(VII)

wherein Ar, L, X and $R^3$ are as defined above for compounds of formula (I),
for example by hydrogenation in the presence of a catalyst such as platinum supported on carbon.

The reaction is suitably carried out in polar protic solvent or mixture of solvents (e.g. methanol and acetic acid).

A compound of formula (VII) wherein L represents —$(CH_2)_nO(CH_2)_m$— or $(CH_2)_nOR^b$, as defined above, wherein n is zero may be prepared by reaction of a compound of formula (VIIIa) or (VIIIb)

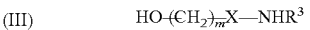
(VIIIa)

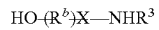
(VIIIb)

or analogues thereof wherein the alkylene chain is substituted, for example, by one or more halogen atoms and wherein X is as defined above for compounds of formula (I) with a compound of formula (IX) or (X)

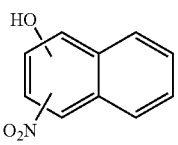
(IX)

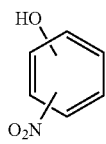
(X)

wherein compounds (IX) and (X) may bear optional substitutents as defined above for compounds of formula (I).

The reaction may be performed under Mitsunobu conditions, such as in the presence of triphenylphosphine and diisopropylazodicarboxylate. The reaction is suitably carried out in a polar aprotic solvent (e.g. tetrahydrofuran, in particular anhydrous tetrahydrofuran).

Compounds of formulae (III), (IV), (VI), (VIIIa), (VIIIb), (IX) and (X) are either commercially available, or are known, or are novel and can be readily prepared by conventional methods. See for example Regan, J. et al.; *J. Med. Chem.*, 2003, 46, 4676-4686, WO00/043384, WO2007/087448 and WO2007/089512.

Protecting groups may be required to protect chemically sensitive groups during one or more of the reactions described above, to ensure that the process is efficient. Thus if desired or necessary, intermediate compounds may be protected by the use of conventional protecting groups. Protecting groups and means for their removal are described in "Protective Groups in Organic Synthesis", by Theodora W. Greene and Peter G. M. Wuts, published by John Wiley & Sons Inc; 4$^{th}$ Rev Ed., 2006, ISBN-10: 0471697540.

Novel intermediates are claimed as an aspect of the invention.

In one aspect the compounds are useful in treatment, for example COPD and/or asthma.

The compounds developed to date have typically been intended for oral administration. This strategy involves optimizing compounds which achieve their duration of action by an appropriate pharmacokinetic profile. This ensures that there is a sufficient drug concentration established and maintained after and between doses to provide clinical benefit. The inevitable consequence of this approach is that all body tissues, especially liver and gut, are likely to be exposed to therapeutically active concentrations of the drug, whether or not they are adversely affected by the disease being treated.

An alternative strategy is to design treatment approaches in which the drug is dosed directly to the inflamed organ (topical therapy). While this approach is not suitable for treating all chronic inflammatory diseases, it has been extensively exploited in lung diseases (asthma, COPD), skin diseases (atopic dermatitis and psoriasis), nasal diseases (allergic rhinitis) and gastrointestinal diseases (ulcerative colitis).

In topical therapy, efficacy can be achieved either by (i) ensuring that the drug has a sustained duration of action and is retained in the relevant organ to minimize the risks of systemic toxicity or (ii) producing a formulation which generates a "reservoir" of the active drug which is available to sustain the drug's desired effects. Approach (i) is exemplified by the anticholinergic drug tiotropium (Spiriva), which is administered topically to the lung as a treatment for COPD, and which has an exceptionally high affinity for its target receptor resulting in a very slow off rate and a consequent sustained duration of action.

In one aspect of the disclosure the compounds herein are particularly suitable for topical delivery, such as topical delivery to the lungs, in particular for the treatment of COPD.

In one aspect the compounds have a longer duration of actions than BIRB 796.

In one embodiment the compounds are suitable for sensitizing patients to treatment with a corticosteroid.

The compounds herein may also be useful for the treatment of rheumatoid arthritis.

Further, the present invention provides a pharmaceutical composition comprising a compound according to the disclosure optionally in combination with one or more pharmaceutically acceptable diluents or carriers.

Diluents and carriers may include those suitable for parenteral, oral, topical, mucosal and rectal administration.

As mentioned above, such compositions may be prepared e.g. for parenteral, subcutaneous, intramuscular, intravenous, intra-articular or peri-articular administration, particularly in the form of liquid solutions or suspensions; for oral administration, particularly in the form of tablets or capsules; for topical e.g. pulmonary or intranasal administration, particularly in the form of powders, nasal drops or aerosols and transdermal administration; for mucosal administration e.g. to buccal, sublingual or vaginal mucosa, and for rectal administration e.g. in the form of a suppository.

The compositions may conveniently be administered in unit dosage form and may be prepared by any of the methods well-known in the pharmaceutical art, for example as described in Remington's Pharmaceutical Sciences, 17th ed., Mack Publishing Company, Easton, Pa., (1985). Formulations for parenteral administration may contain as excipients sterile water or saline, alkylene glycols such as propylene glycol, polyalkylene glycols such as polyethylene glycol, oils of vegetable origin, hydrogenated naphthalenes and the like. Formulations for nasal administration may be solid and may contain excipients, for example, lactose or dextran, or may be aqueous or oily solutions for use in the form of nasal drops or metered spray. For buccal administration typical excipients include sugars, calcium stearate, magnesium stearate, pregelatinated starch, and the like.

Compositions suitable for oral administration may comprise one or more physiologically compatible carriers and/or excipients and may be in solid or liquid form. Tablets and capsules may be prepared with binding agents, for example, syrup, acacia, gelatin, sorbitol, tragacanth, or poly-vinylpyrollidone; fillers, such as lactose, sucrose, corn starch, calcium phosphate, sorbitol, or glycine; lubricants, such as magnesium stearate, talc, polyethylene glycol, or silica; and surfactants, such as sodium lauryl sulfate. Liquid compositions may contain conventional additives such as suspending agents, for example sorbitol syrup, methyl cellulose, sugar syrup, gelatin, carboxymethyl-cellulose, or edible fats; emulsifying agents such as lecithin, or acacia; vegetable oils such as almond oil, coconut oil, cod liver oil, or peanut oil; preservatives such as butylated hydroxyanisole (BHA) and butylated hydroxytoluene (BHT). Liquid compositions may be encapsulated in, for example, gelatin to provide a unit dosage form.

Solid oral dosage forms include tablets, two-piece hard shell capsules and soft elastic gelatin (SEG) capsules.

A dry shell formulation typically comprises of about 40% to 60% concentration of gelatin, about a 20% to 30% concentration of plasticizer (such as glycerin, sorbitol or propylene glycol) and about a 30% to 40% concentration of water. Other materials such as preservatives, dyes, opacifiers and flavours also may be present. The liquid fill material comprises a solid drug that has been dissolved, solubilized or dispersed (with suspending agents such as beeswax, hydrogenated castor oil or polyethylene glycol 4000) or a liquid drug in vehicles or combinations of vehicles such as mineral oil, vegetable oils, triglycerides, glycols, polyols and surface-active agents.

Suitably the compound of formula (I) is administered topically to the lung. Hence we provide according to the invention a pharmaceutical composition comprising a compound of the disclosure optionally in combination with one or more topically acceptable diluents or carriers. Topical administration to the lung may be achieved by use of an aerosol formulation. Aerosol formulations typically comprise the active ingredient suspended or dissolved in a suitable aerosol propellant, such as a chlorofluorocarbon (CFC) or a hydrofluorocarbon (HFC). Suitable CFC propellants include trichloromonofluoromethane (propellant 11), dichlorotetrafluoromethane (propellant 114), and dichlorodifluoromethane (propellant 12). Suitable HFC propellants include tetrafluoroethane (HFC-134a) and heptafluoropropane (HFC-227). The propellant typically comprises 40% to 99.5% e.g. 40% to 90% by weight of the total inhalation composition. The formulation may comprise excipients including co-solvents (e.g. ethanol) and surfactants (e.g. lecithin, sorbitan trioleate and the like). Aerosol formulations are packaged in canisters and a suitable dose is delivered by means of a metering valve (e.g. as supplied by Bespak, Valois or 3M).

Topical administration to the lung may also be achieved by use of a non-pressurised formulation such as an aqueous solution or suspension. This may be administered by means of a nebuliser.

Topical administration to the lung may also be achieved by use of a dry-powder formulation. A dry powder formulation will contain the compound of the disclosure in finely divided form, typically with a mass mean diameter (MMAD) of 1-10 microns. The formulation will typically contain a topically acceptable diluent such as lactose, usually of large particle size e.g. a mass mean diameter (MMAD) of 100 μm or more.

Example dry powder delivery systems include SPINHALER, DISKHALER, TURBOHALER, DISKUS and CLICKHALER.

Compounds according to the disclosure are intended to have therapeutic activity. In a further aspect, the present invention provides a compound of the disclosure for use as a medicament.

Compounds according to the disclosure may also be useful in the treatment of respiratory disorders including COPD (including chronic bronchitis and emphysema), asthma, paediatric asthma, cystic fibrosis, sarcoidosis, idiopathic pulmonary fibrosis, allergic rhinitis, rhinitis, sinusitis, especially asthma, chronic bronchitis and COPD.

Compounds of the disclosure may also re-sensitise the patient's condition to treatment with a corticosteroid, when the patient's condition has become refractory to the same.

Compounds according to the disclosure are also expected to be useful in the treatment of certain conditions which may be treated by topical or local therapy including allergic conjunctivitis, conjunctivitis, allergic dermatitis, contact dermatitis, psoriasis, ulcerative colitis, inflamed joints secondary to rheumatoid arthritis or osteoarthritis.

Compounds of the disclosure are also expected to be useful in the treatment of certain other conditions including rheumatoid arthritis, pancreatitis, cachexia, inhibition of the growth and metastasis of tumours including non-small cell lung carcinoma, breast carcinoma, gastric carcinoma, colorectal carcinomas and malignant melanoma.

Thus, in a further aspect, the present invention provides a compound as described herein for use in the treatment of the above mentioned conditions.

In a further aspect, the present invention provides use of a compound as described herein for the manufacture of a medicament for the treatment of the above mentioned conditions.

In a further aspect, the present invention provides a method of treatment of the above mentioned conditions which comprises administering to a subject an effective amount of a compound of the disclosure or a pharmaceutical composition thereof.

A compound of the disclosure may also be administered in combination with one or more other active ingredients e.g. active ingredients suitable for treating the above mentioned conditions. For example possible combinations for treatment of respiratory disorders include combinations with steroids (e.g. budesonide, beclomethasone dipropionate, fluticasone propionate, mometasone furoate, fluticasone furoate), beta agonists (e.g. terbutaline, salbutamol, salmeterol, formoterol) and/or xanthines (e.g. theophylline).

Abbreviations

AcOH glacial acetic acid
aq aqueous
Ac acetyl
ATP adenosine-5'-triphosphate
BALF bronchoalveolae lavage fluid
br broad
BSA bovine serum albumin
CatCart® catalytic cartridge
CDI 1,1-carbonyl-diimidazole
COPD chronic obstructive pulmonary disease
d doublet
DCM dichloromethane
DIAD diisopropylazadicarboxylate
DIBAL-H diisobutylaluminum hydride
DIPEA N,N-diisopropylethylamine
DMF N,N-dimethylformamide
DMSO dimethyl sulfoxide
EtOAc ethyl acetate
FCS foetal calf serum
hr hour(s)
HRP horseradish peroxidase
JNK c-Jun N-terminal kinase
MAPK mitogen protein activated protein kinase
MeOH methanol
min Minute(s)
MTT 3-(4,5-Dimethylthiazol-2-yl)-2,5-diphenyltetrazolium bromide
PBS phosphate buffered saline
PPh$_3$ triphenylphosphine
RT room temperature
RP HPLC reverse phase high performance liquid chromatography singlet
SCX solid supported cation exchange
SDS sodium dodecyl sulfate
t triplet
TFA trifluoroacetic acid
THF tetrahydrofuran
TMB 3.3', 5.5'-tetramethylbenzidine
TNFα tumor necrosis factor alpha General Procedures All starting materials and solvents were either obtained from commercial sources or prepared according to the literature citation.

Hydrogenations were preformed on a Thales H-cube flow reactor under the conditions stated.

Organic solutions were routinely dried over magnesium sulfate.

SCX was purchased with Supelco and treated with 1M aqueous HCl prior to use. The reaction mixture to be purified was first diluted with MeOH and made acidic with a few drops of AcOH. This solution was loaded directly onto the SCX and washed with MeOH. The desired material was then eluted by washing with 1% NH$_3$ in MeOH.

Column chromatography was performed on Silicycle pre-packed silica (230-400 mesh, 40-63 µM) cartridges using the amount indicated.

Preparative Reverse Phase High Performance Liquid Chromatography:

Agilent Scalar column C18, 5 µm (21.2×50 mm), flow rate 28 mL/min eluting with a H$_2$O-MeCN gradient containing 0.1% v/v formic acid over 10 mins using UV detection at 215 and 254 nm. Gradient information: 0.0-0.5 min: 95% H$_2$O-5% MeCN; 0.5-7.0 min; Ramped from 95% H$_2$O-5% MeCN to 5% H$_2$O-95% MeCN; 7.0-7.9 min: Held at 5% H$_2$O-95% MeCN; 7.9-8.0 min: Returned to 95% H$_2$O-5% MeCN; 8.0-10.0 min: Held at 95% H$_2$O-5% MeCN.

Analytical Methods

Reverse Phase High Performance Liquid Chromatography:

Agilent Scalar column C18, 5 µm (4.6×50 mm) or Waters XBridge C18, 5 µm (4.6×50 mm) flow rate 2.5 mL/min eluting with a H$_2$O-MeCN gradient containing 0.1% v/v formic acid over 7 min employing UV detection at 215 and 254 nm. Gradient information: 0.0-0.1 min: 95% H$_2$O-5% MeCN; 0.1-5.0 min; Ramped from 95% H$_2$O-5% MeCN to 5% H$_2$O-95% MeCN; 5.0-5.5 min: Held at 5% H$_2$O-95% MeCN; 5.5-5.6 min: Held at 5% H$_2$O-95% MeCN, flow rate increased to 3.5 ml/min; 5.6-6.6 min: Held at 5% H$_2$O-95% MeCN, flow rate 3.5 ml/min; 6.6-6.75 min: Returned to 95% H$_2$O-5% MeCN, flow rate 3.5 ml/min; 6.75-6.9 min: Held at 95% H$_2$O-5% MeCN, flow rate 3.5 ml/min; 6.9-7.0 min: Held at 95% H$_2$O-5% MeCN, flow rate reduced to 2.5 ml/min.

$^1$H NMR Spectroscopy:

Bruker Avance III 400 MHz using residual undeuterated solvent as reference

Intermediate A: 1-(4-((2-Aminopyridin-4-yl)methoxy)naphthalen-1-yl)-3-(3-tert-butyl-1-p-tolyl-1H-pyrazol-5-yl)urea

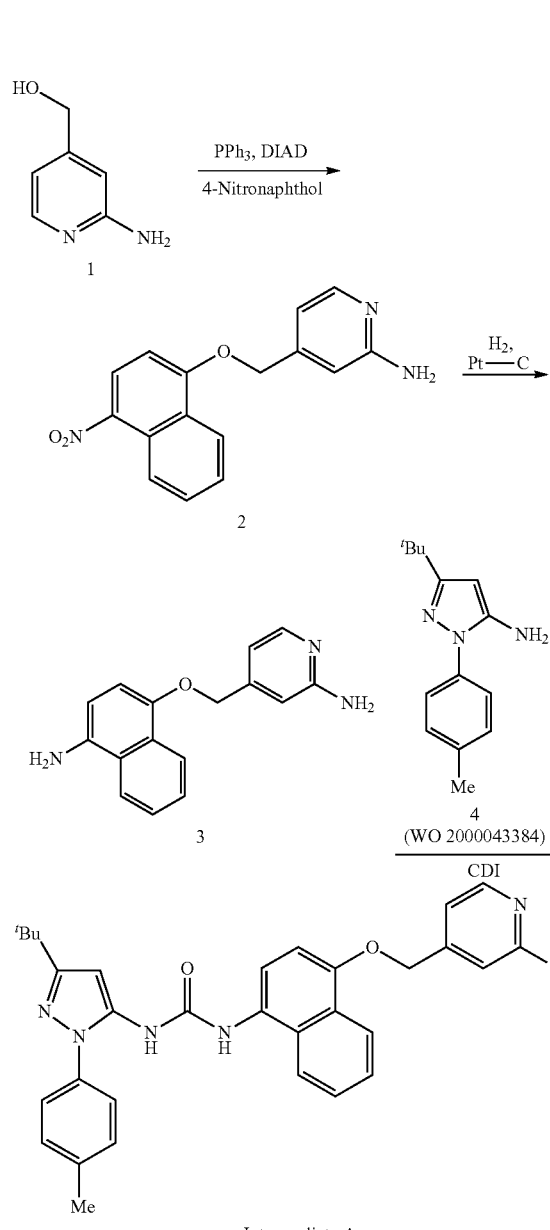

2-Amino-4-((4-nitronaphthalen-1-yloxy)methyl)pyridine (2)

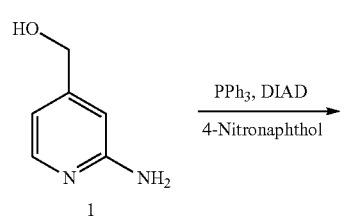

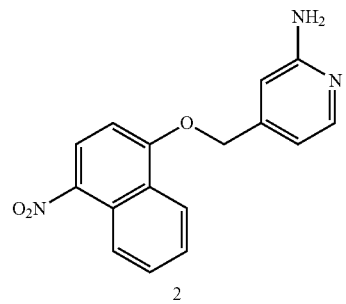

To a solution of 4-nitronaphthol (5.17 g, 27.3 mmol), PPh$_3$ (10.75 g, 41.0 mmol) and 2-aminopyridine-4-methanol (1) (5.09 g, 41.0 mmol) in THF (50 mL) was added dropwise DIAD (8.07 mL, 41.0 mmol) at −15° C. The mixture was stirred overnight at RT and the volatiles removed in vacuo. The crude product was triturated from EtOAc (150 mL), filtered off and washed with EtOAc (100 mL). A second trituration from MeOH (100 mL) gave 2-amino-4-((4-nitronaphthalen-1-yloxy)methyl)pyridine (2) (4.54 g, 56%) as a yellow solid: m/z 296 (M+H)$^+$ (ES$^+$).

2-Amino-4-((4-aminonaphthalen-1-yloxy)methyl)pyridine (3)

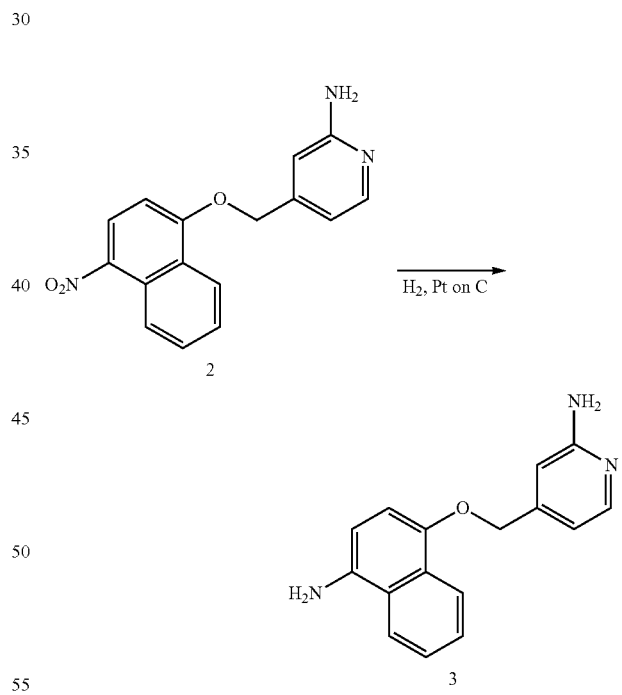

2-Amino-4-((4-nitronaphthalen-1-yloxy)methyl)pyridine (2) (4.50 g, 15.24 mmol) in MeOH (200 mL) and AcOH (200 mL) was passed through a Thales H-cube (2.0 mL·min$^{-1}$, 40° C., 55 mm 10% Pt/C Cat-Cart, full hydrogen mode) and the volatiles were removed in vacuo. The crude product was subjected to SCX capture and release eluting with 1% NH$_3$ in MeOH solution and the solvent was removed in vacuo to give 2-amino-4-((4-aminonaphthalen-1-yloxy)methyl)pyridine (3) (3.82 g, 94%) as a purple solid: m/z 266 (M+H)$^+$ (ES$^+$).

(Intermediate A): 1-(4-((2-Aminopyridin-4-yl)methoxy)naphthalen-1-yl)-3-(3-tert-butyl-1-p-tolyl-1H-pyrazol-5-yl)urea

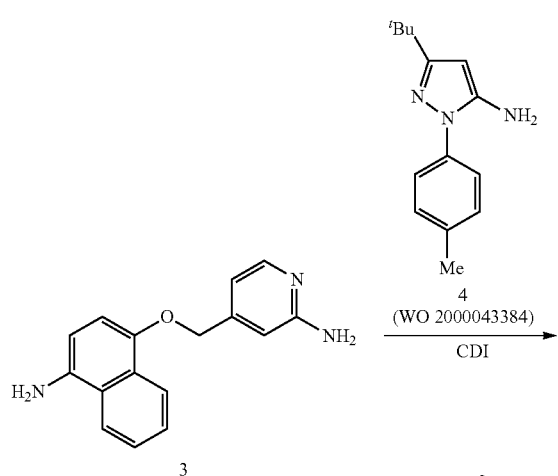

Intermediate A

To a solution of CDI (4.18 g, 25.8 mmol) in DCM (15 mL) was added dropwise under nitrogen a solution of 3-tert-butyl-1-p-tolyl-1H-pyrazol-5-amine (4) (WO 2000043384) (5.91 g, 25.8 mmol) in DCM (15 mL) over 40 min. The resulting solution was stirred at RT for 1 hr then added dropwise under nitrogen to a solution of 2-amino-4-((4-aminonaphthalen-1-yloxy)methyl)pyridine (3) (3.80 g, 12.9 mmol). The mixture was stirred overnight and the volatiles were removed in vacuo. The crude material was purified by column chromatography (120 g); eluting with 0 to 6% MeOH in DCM to give 1-(4-((2-aminopyridin-4-yl)methoxy) naphthalen-1-yl)-3-(3-tert-butyl-1-p-tolyl-1H-pyrazol-5-yl)urea (Intermediate A) as an off white solid (4.27 g, 63%): m/z 521 (M+H)$^+$ (ES$^+$).

EXAMPLE 1

N-(4-((4-(3-(3-tert-Butyl-1-p-tolyl-1H-pyrazol-5-yl)ureido)naphthalen-1-yloxy)methyl)pyridin-2-yl)-2-methoxyacetamide

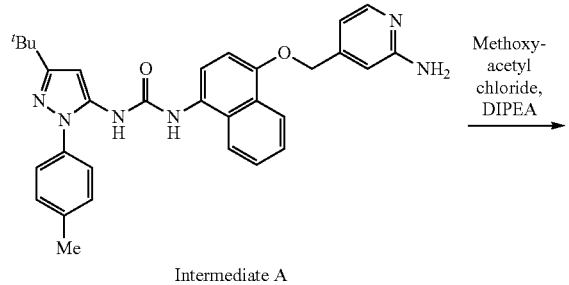

Intermediate A

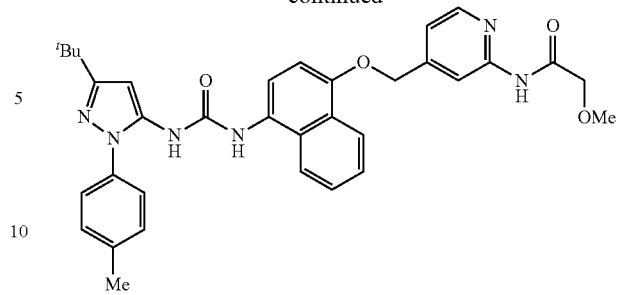

Example 1

To a mixture of 1-(4-((2-aminopyridin-4-yl)methoxy)naphthalen-1-yl)-3-(3-tert-butyl-1-p-tolyl-1H-pyrazol-5-yl)urea (Intermediate A) (526 mg, 0.96 mmol) and DIPEA (184 µL, 1.06 mmol) in DCM/DMF (10:1, 11 mL) was added methoxyacetyl chloride (92 µL, 1.01 mmol). After stirring for 1 hr at RT, further DIPEA (184 µL, 1.06 mmol) and methoxyacetyl chloride (92 µL, 1.01 mmol) were added sequentially and stirring was continued for 1 hr. After the addition of a solution of 1% NH$_3$ in MeOH (40 mL), the mixture was stirred for 15 min and evaporated in vacuo. The crude product was purified by column chromatography (40 g); eluting with 0 to 6% MeOH in DCM to furnish N-(4-((4-(3-(3-tert-butyl-1-p-tolyl-1H-pyrazol-5-yl)ureido) naphthalen-1-yloxy)methyl)pyridin-2-yl)-2-methoxyacetamide (Example 1) as a white solid (286 mg, 49%): m/z 593 (M+H)$^+$ (ES$^+$). $^1$H NMR (400 MHz, DMSO-d$_6$) δ: 1.27 (9H, s), 2.39 (3H, s), 3.32 (3H, s), 4.08 (2H, s), 5.39 (2H, s), 6.36 (1H, s), 7.03 (1H, d), 7.28 (1H, dd), 7.36 (2H, m), 7.44 (2H, m), 7.56-7.64 (3H, m), 7.93 (1H, m), 8.30-8.35 (3H, m), 8.58 (1H, s), 8.79 (1H, s), 10.02 (1H, s).

EXAMPLE 2

Methyl 4-((4-(3-(3-tert-butyl-1-p-tolyl-1H-pyrazol-5-yl)ureido)naphthalen-1-yloxy)methyl)pyridin-2-ylurea

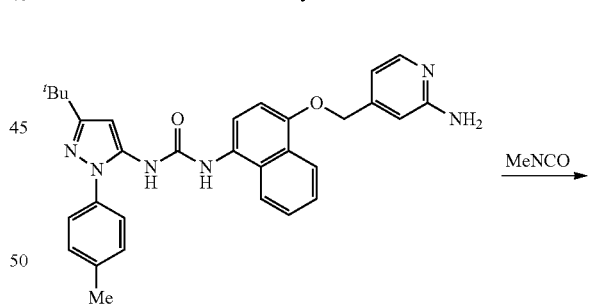

Intermediate A

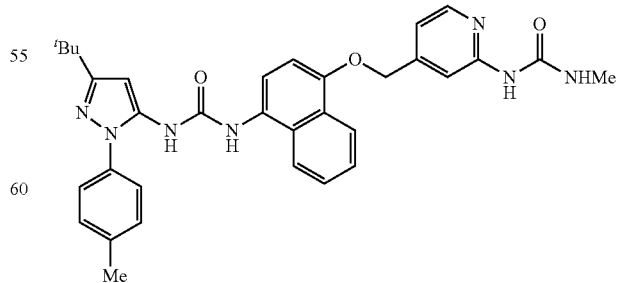

Example 2

To a solution of 1-(4-((2-aminopyridin-4-yl)methoxy)naphthalen-1-yl)-3-(3-tert-butyl-1-p-tolyl-1H-pyrazol-5-yl)

urea (Intermediate A) (70 mg, 0.13 mmol) in anhydrous pyridine (1.5 mL) was added methyl isocyanate (14 μL, 0.24 mmol) and the mixture allowed to stir at RT for 72 hr. Pyridine was removed under vacuum and the residue triturated with DCM (3.0 mL). Filtration afforded an off-white powder, methyl 4-((4-(3-(3-tert-butyl-1-p-tolyl-1H-pyrazol-5-yl)ureido)naphthalen-1-yloxy)methyl)pyridin-2-ylurea (Example 2) (36 mg, 45%): m/z 578 (M+H)$^+$ (ES$^+$). $^1$H NMR (400 MHz, DMSO-d$_6$) δ: 1.27 (9H, s), 2.39 (3H, s), 2.74 (3H, d), 5.30 (2H, s), 6.36 (1H, s), 6.99 (1H, d), 7.05 (d, 1H), 7.35, (2H, d), 7.44 (2H, d), 7.54-7.64 (4H, m), 7.93 (1H, d), 8.19 (1H, d), 8.23 (1H, brs), 8.35 (1H, d), 8.58 (1H, s), 8.79 (1H, s), 9.36 (1H, s).

EXAMPLE 3

N-(4-((4-(3-(3-tert-Butyl-1-p-tolyl-1H-pyrazol-5-yl)ureido)naphthalen-1-yloxy)methyl)pyridin-2-yl)tetrahydro-2H-pyran-4-carboxamide DMF (2 drops) was added to a stirred solution of tetrahydropyran-2H-4-carboxylic acid and oxalyl chloride (21 μL, 0.25 mmol) in DCM (1.0 mL) and the resulting solution was stirred at RT for 1 hr. The solution was evaporated in vacuo to give a colourless oil, which was redissolved in DCM (1.0 mL) and added dropwise to a stirred mixture of 1-(4-((2-aminopyridin-4-yl)methoxy)naphthalen-1-yl)-3-(3-tert-butyl-1-p-tolyl-1H-pyrazol-5-yl)urea (Intermediate A) (50 mg, 0.10 mmol) and DIPEA (84 μL, 0.50 mmol) in DCM (1.0 mL). Stirring was continued for 18 hr. The reaction mixture was stirred in 1% NH$_3$ in MeOH (20 mL) for 30 mins, evaporated in vacuo, pre-adsorbed on silica, and purified by column chromatography (12 g, 0-5% MeOH in DCM, gradient elution) to give N-(4-((4-(3-(3-tert-butyl-1-p-tolyl-1H-pyrazol-5-yl)ureido) naphthalen-1-yloxy)methyl)pyridin-2-yl)tetrahydro-2H-pyran-4-carboxamide (Example 3) as a light tan solid (18 mg, 28%): m/z 633 (M+H)$^+$ (ES$^+$). $^1$H NMR (400 MHz, DMSO-d$_6$) δ: 1.26 (9H, s), 1.57-1.72 (4H, m), 2.38

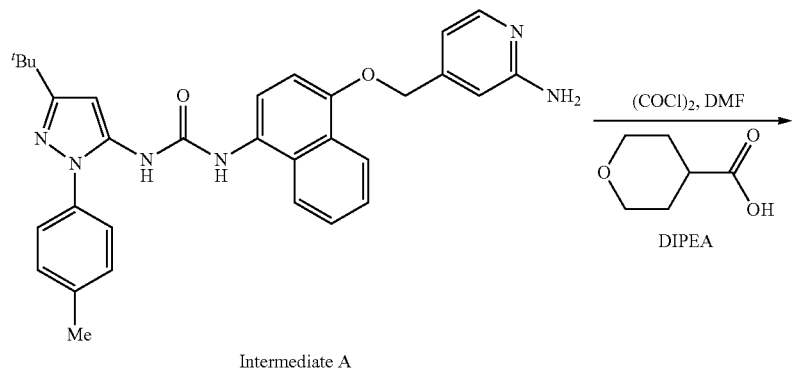

Intermediate A

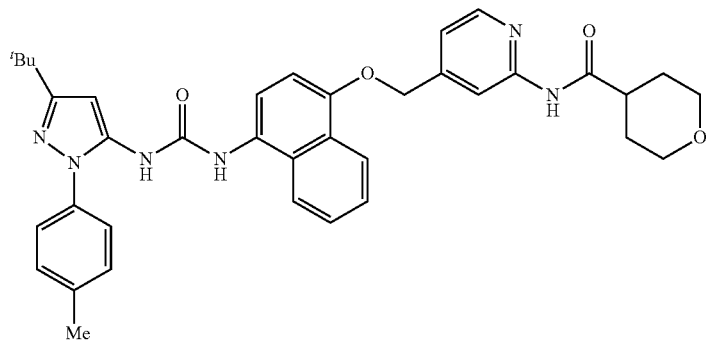

Example 3

(3H, s), 2.75 (1H, m), 3.28-3.33 (2H, m), 3.88 (2H, m), 5.35 (2H, s), 6.34 (1H, s), 6.99 (1H, d), 7.24 (1H, dd), 7.35 (2H, m), 7.43 (2H, m), 7.55-7.64 (3H, m), 7.92 (1H, m), 8.27-8.33 (3H, m), 8.58 (1H, s), 8.78 (1H, s), 10.50 (1H, s).

EXAMPLE 4

(S)—N-(4-((4-(3-(3-tert-Butyl-1-p-tolyl-1H-pyrazol-5-yl)ureido)naphthalen-1-yloxy)methyl)pyridin-2-yl)-2-methoxypropanamide

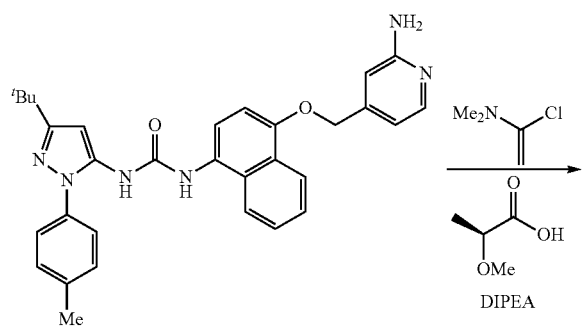

Intermediate A

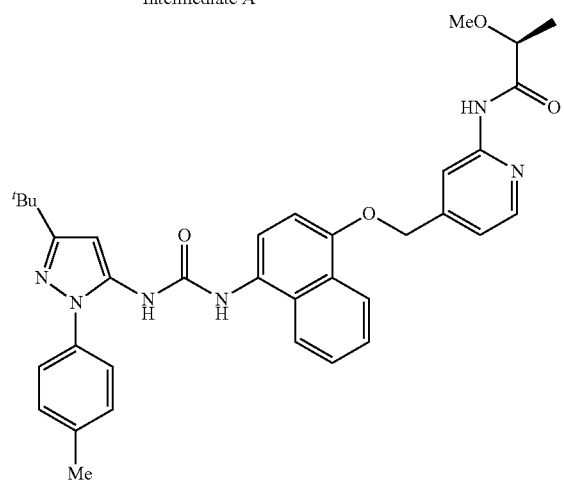

Example 4

1-Chloro-N,N-dimethylethenamine (50 µL, 0.48 mmol) was added to a stirring solution of (S)-2-methoxypropionic acid (50 mg, 0.48 mmol) in DCM (1.0 mL) and the resulting yellow solution was stirred at RT for 1 hr. The solution was added dropwise to a stirring mixture of 1-(4-((2-aminopyridin-4-yl)methoxy)naphthalen-1-yl)-3-(3-tert-butyl-1-p-tolyl-1H-pyrazol-5-yl)urea (Intermediate A) (50 mg, 0.10 mmol) and DIPEA (167 µl, 0.96 mmol) in DCM (1.0 mL). Stirring was continued overnight. The reaction mixture was stirred in 1% NH₃ in MeOH (20 mL), evaporated in vacuo, pre-adsorbed on silica and purified by column chromatography (12 g, 10-50% EtOAc in iso-hexane, gradient elution) to give (S)—N-(4-((4-(3-(3-tert-butyl-1-p-tolyl-1H-pyrazol-5-yl)ureido)naphthalen-1-yloxy)methyl)pyridin-2-yl)-2-methoxypropanamide (Example 4) as a colourless solid (18 mg, 30%): m/z 607 (M+H)⁺ (ES⁺). ¹H NMR (400 MHz, DMSO-d₆) δ: 1.27 (9H, d), 1.31 (3H, s), 2.38 (3H, s), 3.30 (3H, s), 4.02 (1H, q), 5.39 (2H, s), 6.37 (1H, s), 7.00 (1H, d), 7.29 (1H, dd), 7.35 (2H, m), 7.45 (2H, m), 7.56-7.64 (3H, m), 7.93 (1H, m), 8.30-8.37 (3H, m), 8.58 (1H, s), 8.79 (1H, s), 10.06 (1H, s).

EXAMPLE 5

(R)—N-(4-((4-(3-(3-tert-Butyl-1-p-tolyl-1H-pyrazol-5-yl)ureido)naphthalen-1-yloxy)methyl)pyridin-2-yl)-2-methoxypropanamide

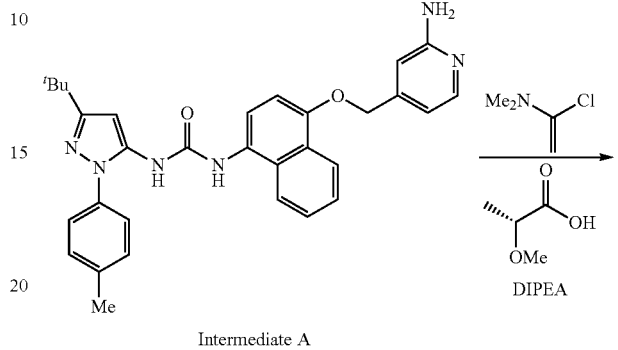

Intermediate A

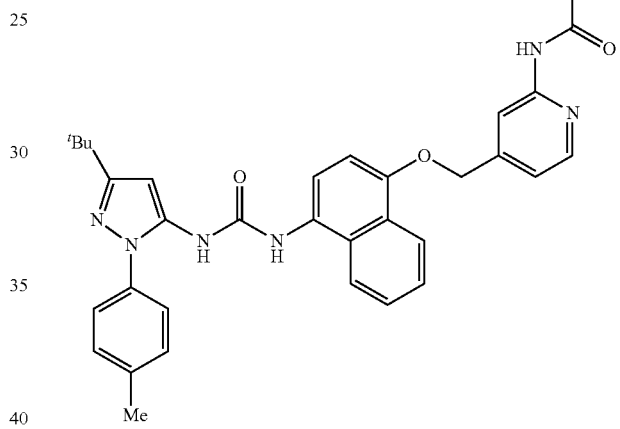

Example 5

1-Chloro-N,N-dimethylethenamine (38 µL, 0.36 mmol) was added to a stirred solution of (R)-2-methoxypropionic acid (37 mg, 0.36 mmol) in DCM (1.0 mL) and the resulting solution was stirred at RT for 1 hr. The solution was added dropwise to a stirred mixture of 1-(4-((2-aminopyridin-4-yl)methoxy)naphthalen-1-yl)-3-(3-tert-butyl-1-p-tolyl-1H-pyrazol-5-yl)urea (Intermediate A) (75 mg, 0.14 mmol) and DIPEA (75 µL, 0.43 mmol) in DCM (2.0 mL) at 0° C. Stirring was continued for a further 48 hr. The mixture was poured into 1% NH₃ in MeOH (20 mL) and stirred for 1 hr, and evaporated in vacuo to give a yellow residue. Column chromatography (12 g, 20-50% EtOAc in iso-hexane) gave (R)—N-(4-((4-(3-(3-tert-butyl-1-p-tolyl-1H-pyrazol-5-yl)ureido)naphthalen-1-yloxy)methyl)pyridin-2-yl)-2-methoxypropanamide (Example 5) as a light pink solid (39 mg, 43%): m/z 607 (M+H)⁺ (ES⁺). ¹H NMR (400 MHz, DMSO-d₆) δ: 1.27 (9H, d), 1.30 (3H, s), 2.39 (3H, s), 3.31 (3H, s), 4.02 (1H, q), 5.39 (2H, s), 6.35 (1H, s), 7.02 (1H, d), 7.29 (1H, dd), 7.35 (2H, m), 7.45 (2H, m), 7.56-7.64 (3H, m), 7.93 (1H, m), 8.30-8.37 (3H, m), 8.58 (1H, s), 8.79 (1H, s), 10.09 (1H, s).

Intermediate B: N-(4-((4-(3-(3-tert-Butyl-1-p-tolyl-1H-pyrazol-5-yl)ureido)naphthalen-1-yloxy)methyl)pyridin-2-yl)-2-chloroacetamide

EXAMPLE 6

N-(4-((4-(3-(3-tert-Butyl-1-p-tolyl-1H-pyrazol-5-yl)ureido)naphthalen-1-yloxy)methyl)pyridin-2-yl)-2-(methylthio)acetamide

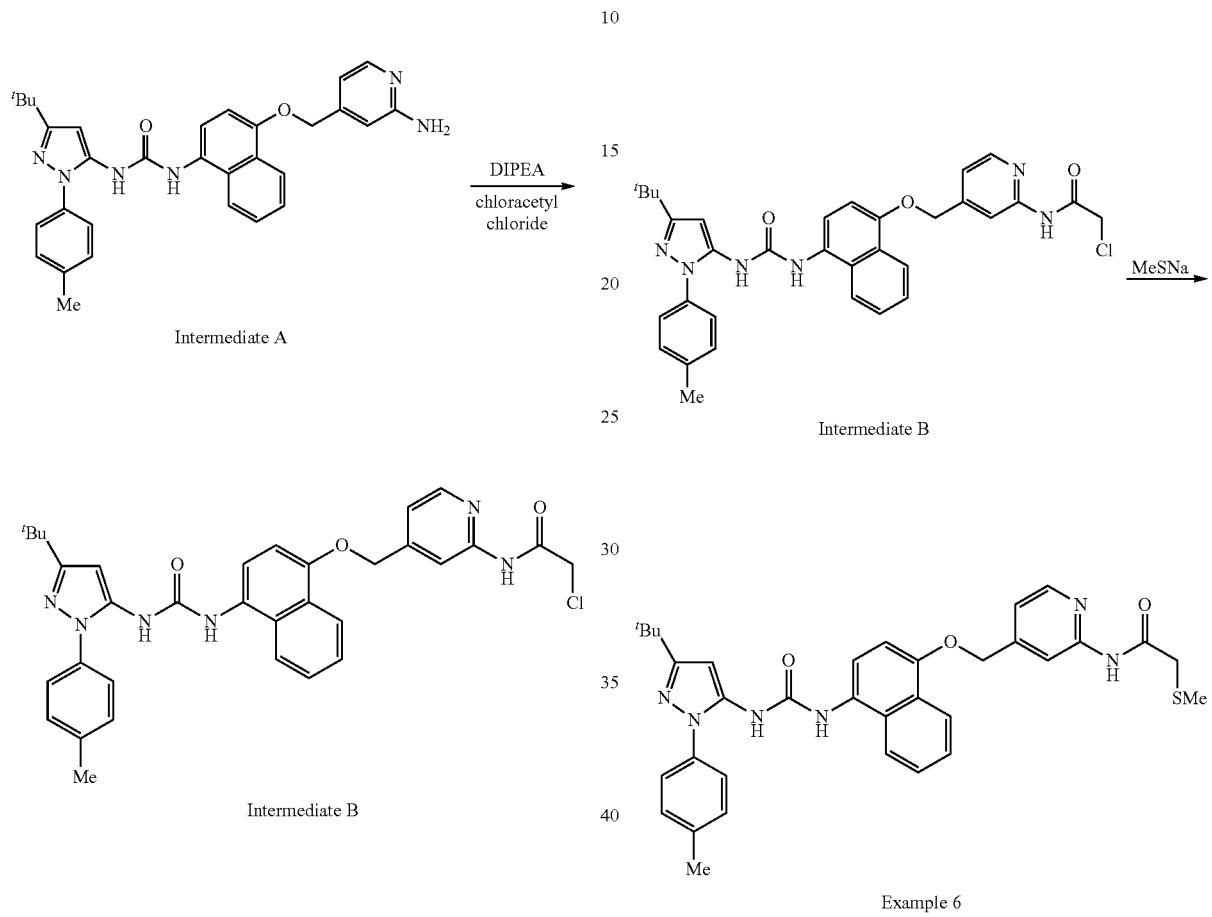

To a solution of DIPEA (1.37 ml, 7.68 mmol) and 1-(4-((2-aminopyridin-4-yl)methoxy)naphthalen-1-yl)-3-(3-tert-butyl-1-p-tolyl-1H-pyrazol-5-yl)urea (Intermediate A) (2.00 g, 3.84 mmol) in DCM (40 mL) and DMF (8.0 mL) was added chloroacetyl chloride (0.61 mL, 7.68 mmol). The reaction mixture was stirred at RT for 1 hr. LC-MS indicated nearly complete consumption of the starting material. A further portion of chloracetyl chloride (100 µl, 1.25 mmol) was added. After stirring for 1 hr at RT, the reaction mixture was partitioned between DCM (40 mL) and saturated aq NaHCO$_3$ solution (40 mL). The organic phase was concentrated in vacuo and purified by column chromatography (80 g, 0-10% MeOH in DCM, gradient elution). Product fractions were concentrated in vacuo and the residue triturated with diethyl ether (20 mL) and iso-hexane (20 mL). The solid was collected by filtration to afford N-(4-((4-(3-(3-tert-butyl-1-p-tolyl-1H-pyrazol-5-yl)ureido)naphthalen-1-yloxy)methyl)pyridin-2-yl)-2-chloroacetamide (Intermediate B) as a light purple solid (1.07 g, 42%): m/z 597, 599 (M+H)$^+$ (ES$^+$).

N-(4-((4-(3-(3-tert-Butyl-1-p-tolyl-1H-pyrazol-5-yl)ureido)naphthalen-1-yloxy)methyl)pyridin-2-yl)-2-chloroacetamide (Intermediate B) (100 mg, 0.17 mmol) was added portionwise to a stirred mixture of sodium thiomethoxide (35 mg, 0.50 mmol) in MeOH (5.0 mL) and the resulting mixture was stirred for 1 hr at RT. The mixture was evaporated in vacuo and partitioned between brine (20 mL) and DCM (30 mL). The organic layer was concentrated in vacuo, the residue pre-adsorbed on silica and purified by column chromatography (12 g, 10-100% EtOAc in iso-hexane, gradient elution). Product fractions were evaporated in vacuo to give N-(4-((4-(3-(3-tert-butyl-1-p-tolyl-1H-pyrazol-5-yl)ureido)naphthalen-1-yloxy)methyl)pyridin-2-yl)-2-(methylthio) acetamide (Example 6) as a light yellow solid (28 mg, 26%): m/z 610 (M+H)$^+$ (ES$^+$). $^1$H NMR (400 MHz, DMSO-d$_6$) δ: 1.27 (9H, s), 2.16 (3H, s), 2.39 (3H, s), 3.53 (2H, s), 5.37 (2H, s), 6.35 (1H, s), 7.01 (1H, d), 7.26 (1H, dd), 7.35 (2H, m), 7.44 (2H, m), 7.55-7.64 (3H, m), 7.92 (1H, m), 8.30-8.35 (3H, m), 8.58 (1H, s), 8.78 (1H, s), 10.60 (1H, s).

EXAMPLE 7

N-(4-((4-(3-(3-tert-Butyl-1-p-tolyl-1H-pyrazol-5-yl)ureido)naphthalen-1-yloxy)methyl)pyridin-2-yl)-2-morpholinoacetamide

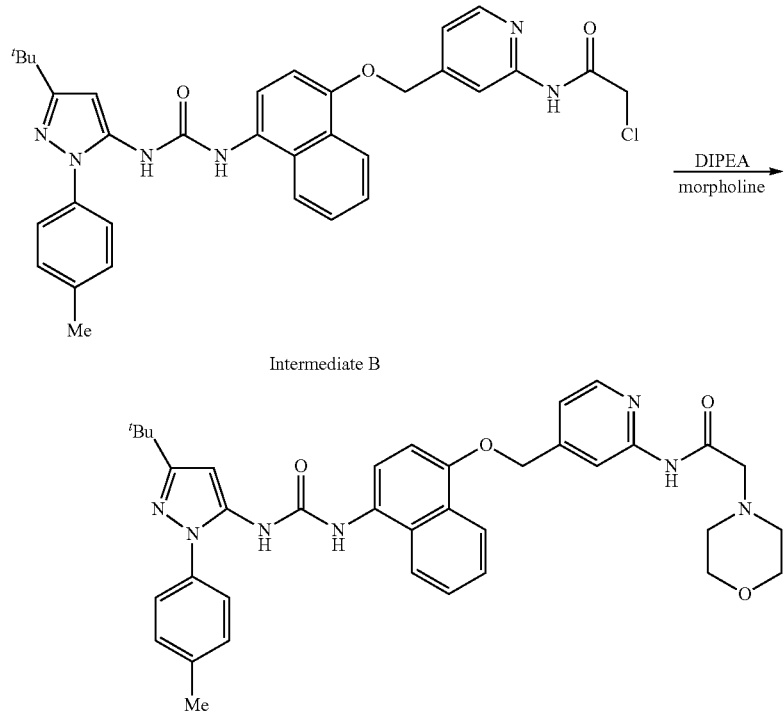

Intermediate B

Example 7

To a solution of N-(4-((4-(3-(3-tert-butyl-1-p-tolyl-1H-pyrazol-5-yl)ureido)naphthalen-1-yloxy)methyl)pyridin-2-yl)-2-chloroacetamide (Intermediate B) (50 mg, 0.08 mmol) in DCM (1.0 mL), DMF (0.1 mL) and DIPEA (21.9 µl, 0.13 mmol) was added morpholine (11.0 µl, 0.13 mmol). The reaction mixture was stirred at RT for 3 hr. LC-MS indicated 20% conversion to product. The reaction mixture was heated to 40° C. and stirred for 12 hr. LC-MS indicated 87% conversion to product. A further portion of morpholine (11.0 µl, 0.13 mmol) was added and the reaction mixture stirred at 40° C. for 5 hr. LC-MS indicated 94% conversion to product. The crude reaction mixture was purified by column chromatography (12 g, 0-10% MeOH in DCM, gradient elution). Product fractions were concentrated in vacuo and the residue triturated with MeOH (5.0 mL). The solid was collected by filtration to afford N-(4-((4-(3-(3-tert-butyl-1-p-tolyl-1H-pyrazol-5-yl)ureido)naphthalen-1-yloxy)methyl)pyridin-2-yl)-2-morpholinoacetamide (Example 7) as a light yellow solid (11 mg, 20%): m/z 648 (M+H)$^+$ (ES$^+$). $^1$H NMR (400 MHz, DMSO-d$_6$) δ: 1.27 (9H, s), 2.39 (3H, s), 2.54 (4H, m), 3.20 (2H, s), 3.63 (4H, m), 5.39 (2H, s), 6.35 (1H, s), 7.01 (1H, d), 7.28 (1H, d), 7.35 (2H, d), 7.43 (2H, d), 7.63-7.56 (3H, m), 7.92 (1H, d), 8.37-8.29 (3H, m), 8.58 (1H, s), 8.79 (1H, s), 10.01 (1H, s).

EXAMPLE 8

N-(4-((4-(3-(3-tert-Butyl-1-p-tolyl-1H-pyrazol-5-yl)ureido)naphthalen-1-yloxy)methyl)pyridin-2-yl)-2-(pyrrolidin-1-yl)acetamide

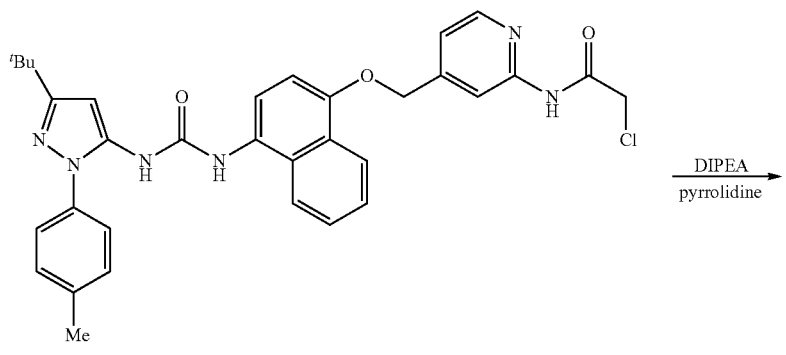

Intermediate B

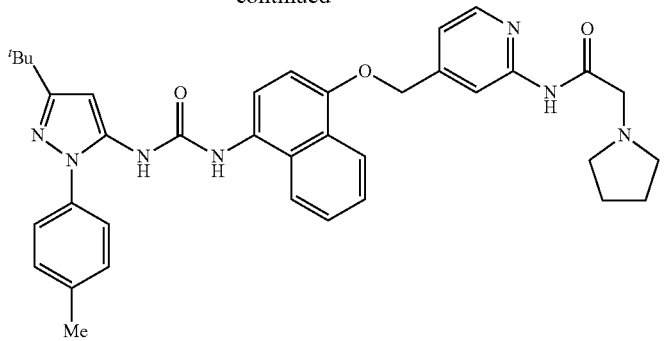

Example 8

To a solution of N-(4-((4-(3-(3-tert-butyl-1-p-tolyl-1H-pyrazol-5-yl)ureido)naphthalen-1-yloxy)methyl)pyridin-2-yl)-2-chloroacetamide (Intermediate B) (50 mg, 0.08 mmol) in DCM (1.0 mL), DMF (0.1 mL) and DIPEA (22 µl, 0.13 mmol) was added pyrrolidine (7.0 µl, 0.08 mmol). The reaction mixture was stirred at RT for 3 hr. LC-MS indicated 50% conversion to product.

The reaction mixture was heated to 40° C. and stirred for 12 hr. LC-MS indicated 95% conversion to product. A further portion of pyrrolidine (7.0 µl, 0.08 mmol) was added and the reaction mixture continued to stir at 40° C. for 5 hr. LC-MS indicated complete conversion to product. The crude reaction mixture was purified by column chromatography (12 g, 0-10% MeOH in DCM, gradient elution) to afford N-(4-((4-(3-(3-tert-butyl-1-p-tolyl-1H-pyrazol-5-yl)ureido)naphthalen-1-yloxy)methyl)pyridin-2-yl)-2-(pyrrolidin-1-yl)acetamide (Example 8) as a light orange solid (17 mg, 32%): m/z 632 (M+H)$^+$ (ES$^+$). $^1$H NMR (400 MHz, DMSO-d$_6$) δ: 1.27 (9H, s), 1.76 (4H, m), 2.39 (3H, s), 2.62 (4H, m), 5.39 (2H, s), 6.35 (1H, s), 7.01 (1H, d), 7.28 (1H, d), 7.34 (2H, d), 7.44 (2H, d), 7.65-7.55 (3H, m), 7.92 (1H, d), 8.36-8.29 (3H, m), 8.58 (1H, s), 8.79 (1H, s), 9.93 (1H, s).

EXAMPLE 9

N-(4-((4-(3-(3-tert-Butyl-1-p-tolyl-1H-pyrazol-5-yl)ureido)naphthalen-1-yloxy)methyl)pyridin-2-yl)-2-(4-methylpiperazin-1-yl)acetamide

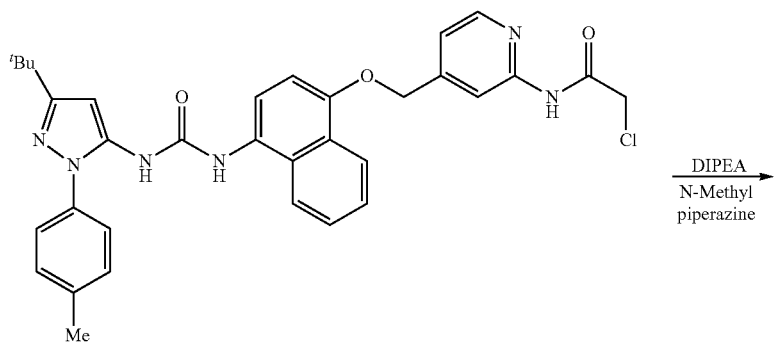

Intermediate B

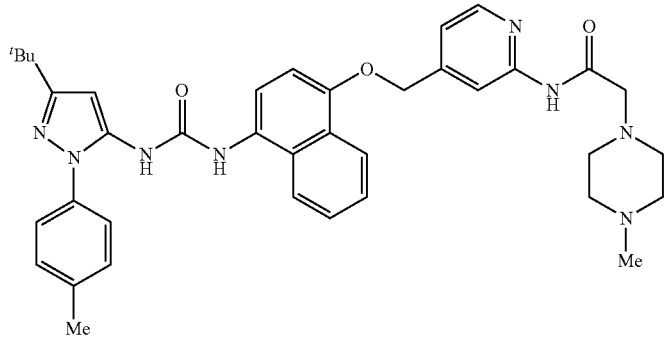

Example 9

To a solution of N-(4-((4-(3-(3-tert-butyl-1-p-tolyl-1H-pyrazol-5-yl)ureido)naphthalen-1-yloxy)methyl)pyridin-2-yl)-2-chloroacetamide (Intermediate B) (50 mg, 0.08 mmol) in DCM (1.0 mL), DMF (0.1 mL) and DIPEA (22 µl, 0.13 mmol) was added N-methyl piperazine (9.3 µl, 0.08 mmol).

The reaction mixture was stirred at RT for 3 hr. LC-MS indicated 20% conversion to product. The reaction mixture was heated to 40° C. and stirred for 12 hr. LC-MS indicated 91% conversion to product. A further portion of N-methyl piperazine (9.0 µl, 0.08 mmol) was added and the reaction mixture continued to stir at 40° C. for 5 hr. LC-MS indicated 98% conversion to product. The crude reaction mixture was purified by column chromatography (12 g, 0-10% MeOH in DCM, gradient elution). Product fractions were concentrated in vacuo and the residue triturated with a mixture of diethyl ether, DCM and iso-hexane (2:1:2, 5.0 mL) to afford N-(4-((4-(3-(3-tert-butyl-1-p-tolyl-1H-pyrazol-5-yl)ureido)naphthalen-1-yloxy)methyl)pyridin-2-yl)-2-(4-methylpiperazin-1-yl)acetamide (Example 9) as a light orange solid (26 mg, 47%): m/z 661 (M+H)$^+$ (ES$^+$). $^1$H NMR (400 MHz, DMSO-d$_6$) δ: 1.27 (9H, s), 2.39 (3H, s), 2.69-2.60 (3H, bm), 2.88-2.73 (3H, bm), 3.17-2.95 (4H, bm), 5.39 (2H, s), 6.34 (1H, s), 7.00 (1H, d), 7.29 (1H, d), 7.35 (2H, d), 7.45 (2H, d), 7.66-7.56 (3H, m), 7.98 (1H, d), 8.37-8.28 (3H, m), 8.73 (1H, s), 8.91 (1H, s), 10.12 (1H, s).

EXAMPLE 10

N-(4-((4-(3-(3-tert-Butyl-1-p-tolyl-1H-pyrazol-5-yl)ureido)naphthalen-1-yloxy)methyl)pyridin-2-yl)-2-(4-(2-methoxyethyl)piperazin-1-yl)acetamide To a solution of N-(4-((4-(3-(3-tert-butyl-1-p-tolyl-1H-pyrazol-5-yl)ureido)naphthalen-1-yloxy)methyl)pyridin-2-yl)-2-chloroacetamide (Intermediate B) (50 mg, 0.08 mmol) in DCM (1.0 mL), DMF (0.1 mL) and DIPEA (22 µl, 0.13 mmol) was added N-methoxyethyl piperazine (12.5 µl, 0.08 mmol). The reaction mixture was stirred at RT for 3 hr. LC-MS indicated 20% conversion to product. The reaction mixture was heated to 40° C. and stirred for 12 hr. LC-MS indicated 78% conversion to product. A further portion of N-methoxyethyl piperazine (12.5 µl, 0.08 mmol) was added and the reaction mixture continued to stir at 40° C. for 5 hr. LC-MS indicated 89% conversion to product. The crude reaction mixture was purified by column chromatography (12 g, 0-10% MeOH in DCM, gradient elution) to afford N-(4-((4-(3-(3-tert-butyl-1-p-tolyl-1H-pyrazol-5-yl)ureido)naphthalen-1-yloxy)methyl)pyridin-2-yl)-2-(4-(2-methoxyethyl)piperazin-1-yl)acetamide (Example 10) as a light orange solid (45 mg, 73%): m/z 705 (M+H)$^+$ (ES$^+$). $^1$H NMR (400 MHz, DMSO) δ: 1.27 (9H, s), 2.39 (3H, s), 2.46-2.48 (3H, m, obscured by DMSO), 2.57-2.50 (4H, m), 3.17 (2H, s), 3.23 (3H, s), 3.42 (2H, t), 5.39 (2H, s), 6.35 (1H, s), 7.01 (1H, d), 7.29 (1H, d), 7.35 (2H, d), 7.43 (2H, d), 7.65-7.55 (3H, m), 7.93 (1H, d), 8.36-8.30 (3H, m), 8.58 (1H, s), 8.79 (1H, s), 9.92 (1H, s).

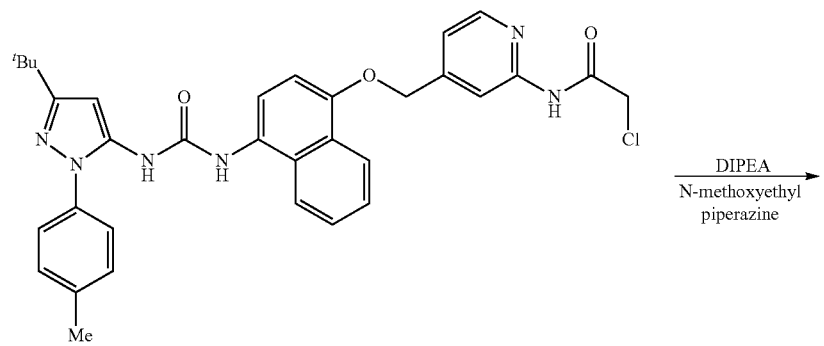

Intermediate B

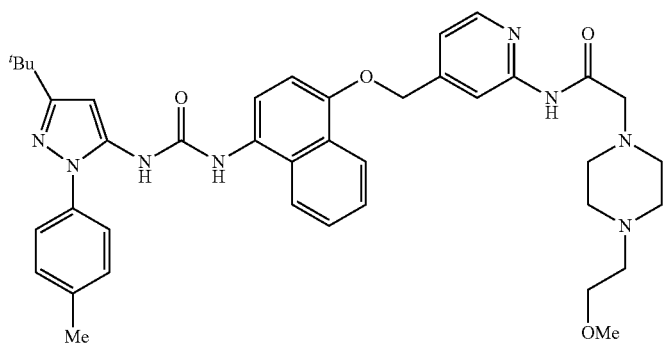

Example 10

EXAMPLE 11

N-(4-((4-(3-(3-tert-Butyl-1-p-tolyl-1H-pyrazol-5-yl)ureido)naphthalen-1-yloxy)methyl)pyridin-2-yl)-2-(2-methoxyethylamino)acetamide

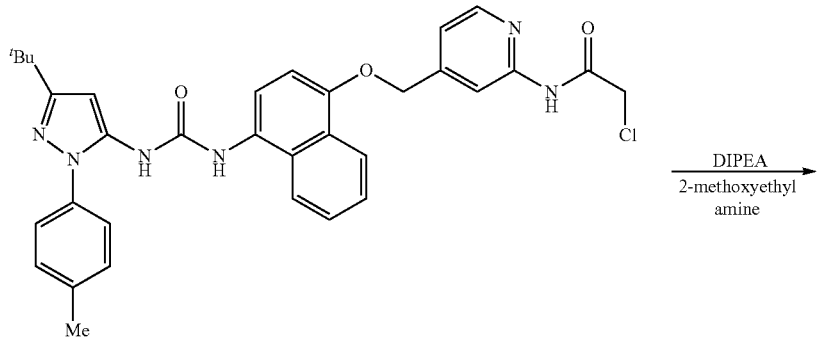

To a solution of N-(4-((4-(3-(3-tert-butyl-1-p-tolyl-1H-pyrazol-5-yl)ureido)naphthalen-1-yloxy)methyl)pyridin-2-yl)-2-chloroacetamide (Intermediate B) (50 mg, 0.08 mmol) in DCM (1.0 mL), DMF (0.1 mL) and DIPEA (17 µl, 0.10 mmol) was added 2-methoxyethylamine (7.0 µl, 0.08 mmol). The reaction mixture was heated to 40° C. and stirred for 12 hr. The crude reaction mixture was purified by column chromatography (12 g, 0-10% MeOH in DCM, gradient elution). Product fractions were concentrated in vacuo and the residue triturated with a mixture of diethyl ether, DCM and isohexane (2:1:2, 5.0 mL) to afford N-(4-((4-(3-(3-tert-butyl-1-p-tolyl-1H-pyrazol-5-yl)ureido)naphthalen-1-yloxy)methyl)pyridin-2-yl)-2-(2-methoxyethylamino)acetamide (Example 11) as an off-white solid (6 mg, 11%): m/z 637 (M+H)$^+$ (ES$^+$).
$^1$H NMR (400 MHz, DMSO-d$_6$) δ: 1.27 (9H, s), 2.39 (3H, s), 2.71 (2H, t), 3.24 (3H, s), 3.33 (2H, m (obscured by DHO)), 3.40 (2H, t), 5.38 (2H, s), 6.35 (1H, s), 7.01 (1H, d), 7.27 (1H, d), 7.36 (2H, d), 7.43 (2H, d), 7.64-7.57 (3H, m), 7.92 (1H, m), 8.36-8.30 (3H, m), 8.59 (1H, s), 8.79 (1H, s).

EXAMPLE 12

N-(4-((4-(3-(3-tert-Butyl-1-p-tolyl-1H-pyrazol-5-yl)ureido)naphthalen-1-yloxy)methyl)pyridin-2-yl)-2-(dimethylamino)acetamide

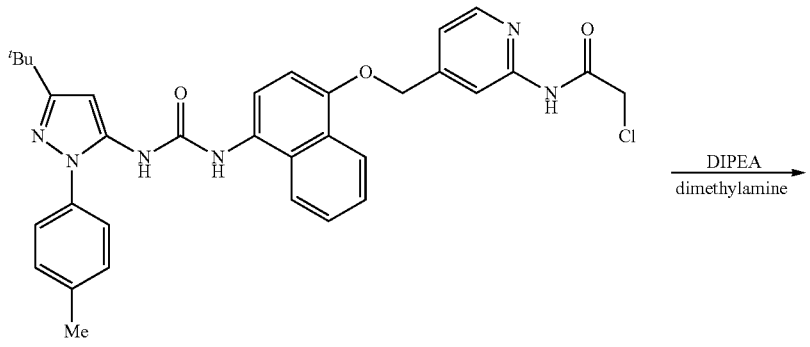

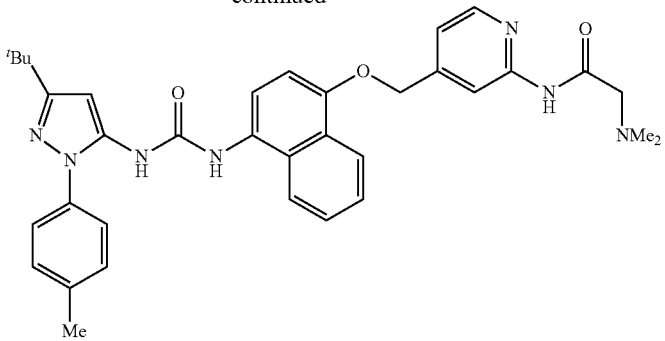

Example 12

To a solution of N-(4-((4-(3-(3-tert-Butyl-1-p-tolyl-1H-pyrazol-5-yl)ureido)naphthalen-1-yloxy)methyl)pyridin-2-yl)-2-chloroacetamide (Intermediate B) (50 mg, 0.08 mmol) in DCM (1.0 mL), DMF (0.1 mL) and DIPEA (17 μl, 0.1 mmol) was added dimethylamine (2.0M solution in THF) (41 μl, 0.08 mmol). The reaction mixture was heated to 40° C. and stirred for 12 hr. The crude reaction mixture was purified by column chromatography (12 g silica, 0-10% MeOH in DCM, gradient elution). Product fractions were concentrated in vacuo and the residue triturated with a mixture of diethyl ether, DCM and iso-hexane (2:1:2, 5.0 mL) to afford N-(4-((4-(3-(3-tert-butyl-1-p-tolyl-1H-pyrazol-5-yl)ureido)naphthalen-1-yloxy)methyl)pyridin-2-yl)-2-(dimethylamino)acetamide (Example 12) as an orange solid (18 mg, 35%): m/z 607 (M+H)$^+$ (ES$^+$). $^1$H NMR (400 MHz, DMSO-d$_6$) δ: 1.27 (9H, s), 2.31 (6H, s), 2.39 (3H, s), 3.14 (2H, s), 5.39 (2H, s), 6.35 (1H, s), 7.01 (1H, d), 7.29 (1H, d), 7.35 (2H, d), 7.44 (2H, d), 7.65-7.55 (3H, m), 7.94 (1H, m), 8.38-8.28 (3H, m), 8.59 (1H, s), 8.79 (1H, s), 9.93 (1H, s).

EXAMPLE 13

N-(4-((4-(3-(3-tert-Butyl-1-p-tolyl-1H-pyrazol-5-yl)ureido)naphthalen-1-yloxy)methyl)pyridin-2-yl)-2-(methylamino)acetamide

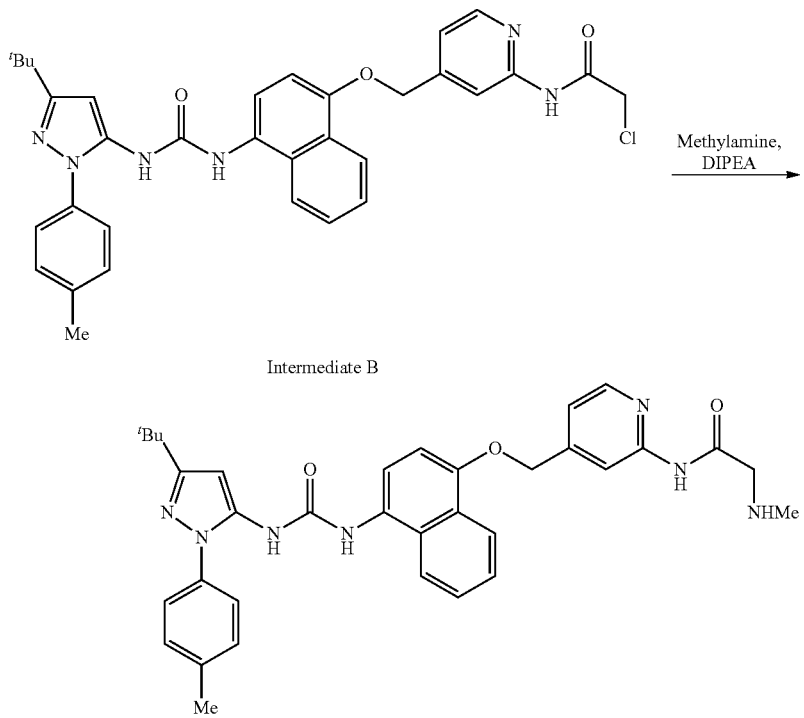

Example 13

To a solution of N-(4-((4-(3-(3-tert-butyl-1-p-tolyl-1H-pyrazol-5-yl)ureido)naphthalen-1-yloxy)methyl)pyridin-2-yl)-2-chloroacetamide (Intermediate B) (50 mg, 0.08 mmol) in DCM (1.0 mL), DMF (0.2 mL) and DIPEA (17 μl, 0.10 mmol) was added methylamine (2.0M solution in THF) (41 μl, 0.08 mmol). The reaction mixture was heated to 40° C. and stirred for 12 hr. The crude reaction mixture was purified by column chromatography (12 g, 0-10% MeOH in DCM, gradient elution). Product fractions were contaminated with an impurity; the crude material was re-purified by column chromatography (12 g, 0-10% MeOH in DCM, gradient elution) to afford N-(4-((4-(3-(3-tert-butyl-1-p-tolyl-1H-pyrazol-5-yl)ureido)naphthalen-1-yloxy)methyl)pyridin-2-yl)-2-(methylamino) acetamide (Example 13) as a light brown solid (6 mg, 12%): m/z 593 (M+H)$^+$ (ES$^+$). $^1$H NMR (400 MHz, DMSO-d$_6$) δ: 1.27 (9H, s), 2.32 (3H, s), 2.39 (3H, s), 3.28 (2H, s), 5.39 (2H, s), 6.35 (1H, s), 7.01 (1H, d), 7.27 (1H, d), 7.35 (2H, d), 7.44 (2H, d), 7.63-7.55 (3H, m), 7.93 (1H, m), 8.37-8.30 (3H, m), 8.59 (1H, s), 8.80 (1H, s).

EXAMPLE 14

N-(4-((4-(3-(3-tert-Butyl-1-p-tolyl-1H-pyrazol-5-yl)ureido)naphthalen-1-yloxy)methyl)pyridin-2-yl)-2-((4-methoxybenzyl)(methyl)amino)acetamide To a solution of N-(4-((4-(3-(3-tert-butyl-1-p-tolyl-1H-pyrazol-5-yl)ureido)naphthalen-1-yloxy)methyl)pyridin-2-yl)-2-chloroacetamide (Intermediate B) (50 mg, 0.08 mmol) in DCM (1.0 mL), DMF (0.2 mL) and DIPEA (17.5 μl, 0.10 mmol) was added N-(4-methoxybenzyl)-N-methylamine (15.5 μl, 0.09 mmol) The reaction mixture was stirred at 55° C. for 12 hr. The crude reaction mixture was purified by column chromatography (12 g, 0-10% MeOH in DCM, gradient elution). Product fractions were concentrated in vacuo and the residue triturated with a mixture of diethyl ether, DCM and iso-hexane (2:1:2, 5.0 mL) to afford N-(4-((4-(3-(3-tert-butyl-1-p-tolyl-1H-pyrazol-5-yl)ureido)naphthalen-1-yloxy)methyl)pyridin-2-yl)-2-((4-methoxybenzyl)(methyl)amino) acetamide (Example 14) as a white solid (7 mg, 11%): m/z 713 (M+H)$^+$ (ES$^+$). $^1$H NMR (400 MHz, DMSO-d$_6$) δ: 1.27 (9H, s), 2.25 (3H, s), 2.39 (3H, s), 3.22 (2H, s), 3.59 (2H, s), 3.72 (3H, s), 5.38 (2H, s), 6.35 (1H, s), 6.90 (2H, m),

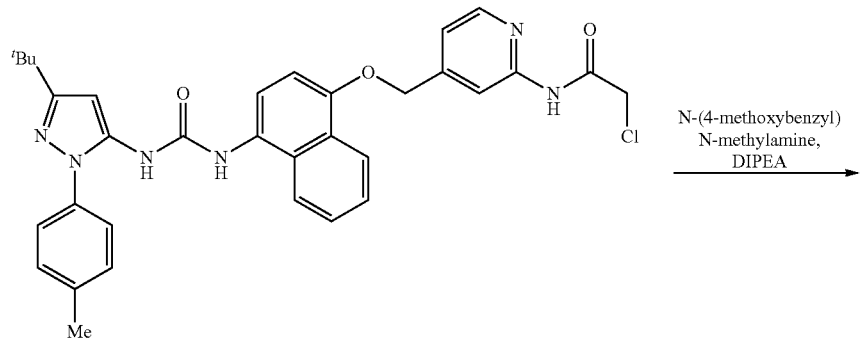

Intermediate B

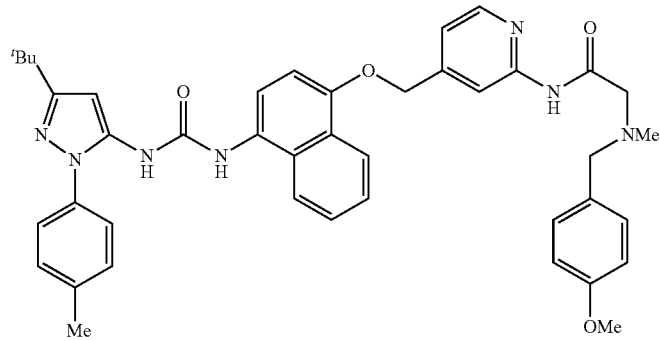

Example 14

7.01 (1H, m), 7.27 (3H, m), 7.35 (2H, m), 7.43 (2H, m), 7.64-7.55 (3H, m), 7.94 (1H, m), 8.37-8.28 (3H, m), 8.58 (1H, s), 8.79 (1H, s), 9.97 (1H, s).

Intermediate C: 1-(4-((3-Aminopyridin-4-yl)methoxy)naphthalen-1-yl)-3-(3-tert-butyl-1-p-tolyl-1H-pyrazol-5-yl)urea

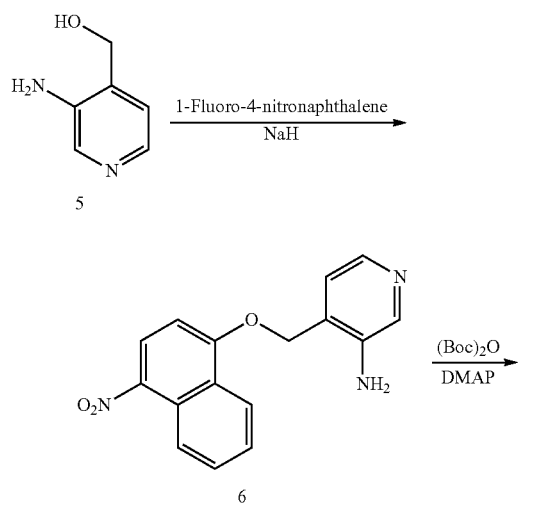

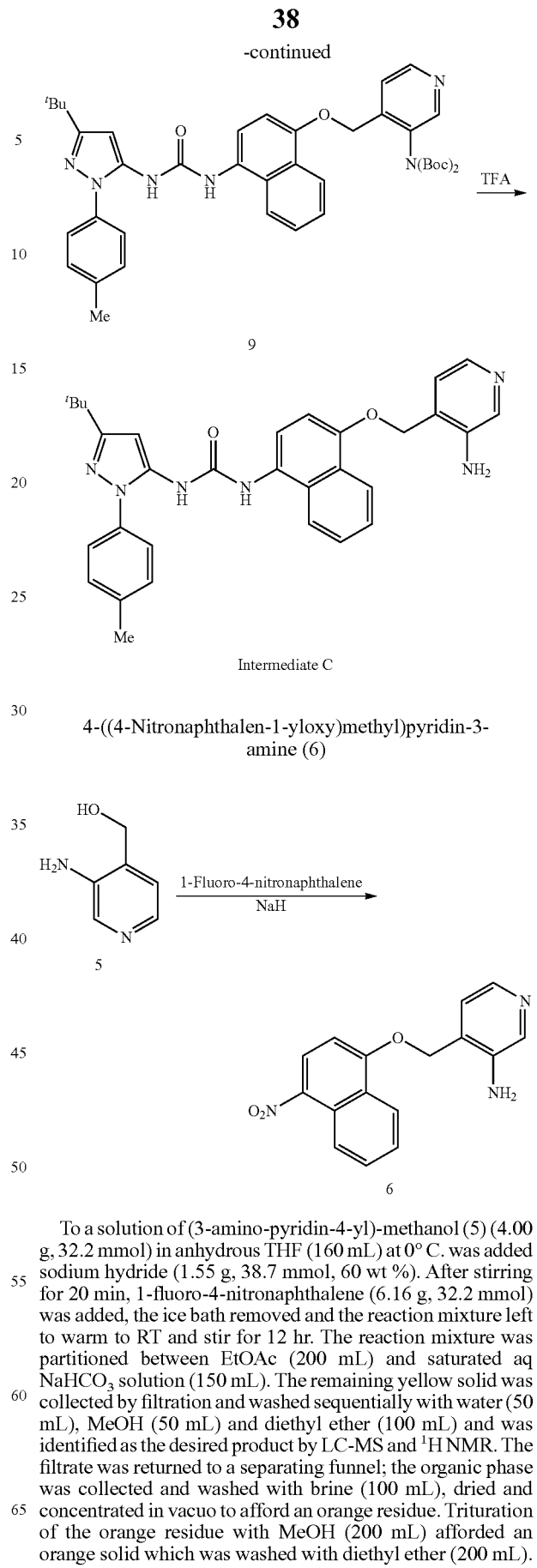

4-((4-Nitronaphthalen-1-yloxy)methyl)pyridin-3-amine (6)

To a solution of (3-amino-pyridin-4-yl)-methanol (5) (4.00 g, 32.2 mmol) in anhydrous THF (160 mL) at 0° C. was added sodium hydride (1.55 g, 38.7 mmol, 60 wt %). After stirring for 20 min, 1-fluoro-4-nitronaphthalene (6.16 g, 32.2 mmol) was added, the ice bath removed and the reaction mixture left to warm to RT and stir for 12 hr. The reaction mixture was partitioned between EtOAc (200 mL) and saturated aq NaHCO$_3$ solution (150 mL). The remaining yellow solid was collected by filtration and washed sequentially with water (50 mL), MeOH (50 mL) and diethyl ether (100 mL) and was identified as the desired product by LC-MS and $^1$H NMR. The filtrate was returned to a separating funnel; the organic phase was collected and washed with brine (100 mL), dried and concentrated in vacuo to afford an orange residue. Trituration of the orange residue with MeOH (200 mL) afforded an orange solid which was washed with diethyl ether (200 mL).

LC-MS and ¹H NMR analysis of the orange solid were identical to that observed for the insoluble solid obtained earlier. The two products were combined to afford 4-((4-nitronaphthalen-1-yloxy)methyl)pyridin-3-amine (6) (7.80 g, 77%): m/z 296 (M+H)⁺ (ES⁺).

Di-tert-butyl 4-((4-nitronaphthalen-1-yloxy)methyl)pyridin-3-yliminodicarbonate (7)

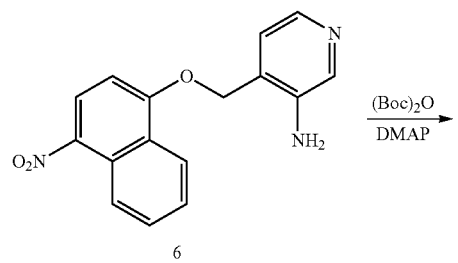

To a suspension of 4-((4-nitronaphthalen-1-yloxy)methyl)pyridin-3-amine (6) (3.00 g, 10.2 mmol) and DMAP (0.25 g, 2.03 mmol) in THF (30 mL) was added a solution of di-tert-butyldicarbonate (2.33 g, 10.7 mmol) in THF (15 mL). After 2-3 min a solution was obtained. The reaction mixture was stirred at RT for 12 hr whereupon further di-tert-butyldicarbonate (2.33 g, 10.7 mmol) was added and the reaction mixture was stirred at RT for 12 hr. The reaction was partitioned between EtOAc (100 mL) and saturated aq NaHCO₃ solution (50 mL). The organic layer was collected, dried and concentrated in vacuo to afford an orange oil. The oil was purified by column chromatography (0-50% EtOAc in iso-hexane, gradient elution) to afford di-tert-butyl 4-((4-nitronaphthalen-1-yloxy)methyl)pyridin-3-yliminodicarbonate (7) as an orange oil which crystallised on standing (2.33 g, 43%): m/z 496 (M+H)⁺ (ES⁺).

Di-tert-butyl 4-((4-aminonaphthalen-1-yloxy)methyl)pyridin-3-yliminodicarbonate (8)

A solution of di-tert-butyl 4-((4-nitronaphthalen-1-yloxy)methyl)pyridin-3-yliminodicarbonate (7) (2.30 g, 4.64 mmol) in MeOH (100 mL) and AcOH (20 mL) was passed through a Thales H-cube (1.0 mL·min⁻¹, 25° C., 55 mm 10% Pt/C Cat-Cart, full hydrogen mode) and the volatiles were removed in vacuo to afford di-tert-butyl 4-((4-aminonaphthalen-1-yloxy)methyl)pyridin-3-yliminodicarbonate (8) as a brown oil (2.12 g, 82%): m/z 466 (M+H)⁺ (ES⁺).

Di-tert-butyl 4-((4-(3-(3-tert-butyl-1-p-tolyl-1H-pyrazol-5-yl)ureido)naphthalen-1-yloxy)methyl)pyridin-3-yliminodicarbonate (9)

A solution of 3-tert-butyl-1-p-tolyl-1H-pyrazol-5-amine (4) (WO 2000043384) (1.55 g, 6.77 mmol) in DCM (4.0 mL) was added dropwise over 25 min to a suspension of CDI (1.10 g, 6.77 mmol) in DCM (4.0 mL) at RT. The reaction mixture was stirred for 80 min at RT and a solution of di-tert-butyl 4-((4-aminonaphthalen-1-yloxy)methyl)pyridin-3-yliminodicarbonate (8) (2.10 g, 4.51 mmol) in DCM (10 mL) was added to the reaction mixture in one portion and stirred for 12 hr. The reaction mixture was partitioned between saturated aq NaHCO₃ solution (20 mL) and DCM (20 mL). The organic layer was collected, dried and concentrated in vacuo to afford a purple residue. The crude material was purified by column chromatography (80 g, 0-100% EtOAc in iso-hexane, gradient elution) to afford di-tert-butyl 4-((4-(3-(3-tert-butyl-1-p-tolyl-1H-pyrazol-5-yl)ureido)naphthalen-1-yloxy)methyl)pyridin-3-yliminodicarbonate (9) as a purple solid (1.77 g, 53%): m/z 721 (M+H)⁺ (ES⁺).

Intermediate C: 1-(4-((3-aminopyridin-4-yl)methoxy)naphthalen-1-yl)-3-(3-tert-butyl-1-p-tolyl-1H-pyrazol-5-yl)urea

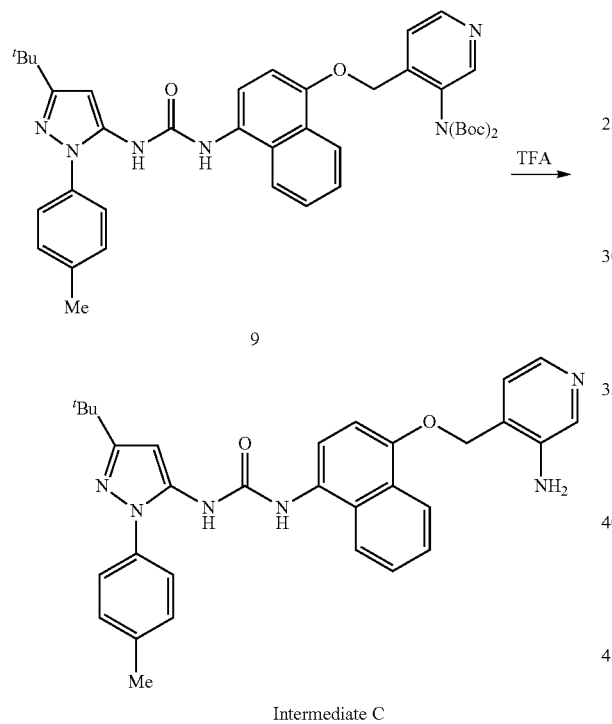

Intermediate C

TFA (2.0 mL) was added to a solution of di-tert-butyl 4-((4-(3-(3-tert-butyl-1-p-tolyl-1H-pyrazol-5-yl)ureido)naphthalen-1-yloxy)methyl)pyridin-3-yliminodicarbonate (9) (1.70 g, 2.36 mmol) in DCM (10 mL). After for 1 hr stirring at RT further TFA (2.0 mL) was added and the reaction mixture stirred for 12 hr at RT. The solvents were removed in vacuo and the product purified by SCX capture and release, followed by trituration with DCM (20 mL) to afford 1-(4-((3-aminopyridin-4-yl)methoxy)naphthalen-1-yl)-3-(3-tert-butyl-1-p-tolyl-1H-pyrazol-5-yl)urea (Intermediate C) as a pale buff solid (0.96 g, 77%): m/z 521 (M+H)⁺ (ES⁺). ¹H NMR (400 MHz, DMSO-d₆) δ: 1.27 (9H, s), 2.39 (3H, s), 5.16 (2H, s), 5.38 (2H, s), 6.35 (1H, s), 7.05 (1H, d), 7.32 (1H, d), 7.35 (2H, d), 7.43 (2H, m), 7.64-7.51 (2H, m), 7.63 (1H, d), 7.82 (1H, d), 7.91 (1H, m), 8.03 (1H, s), 8.29 (1H, m), 8.57 (1H, s), 8.78 (1H, s).

EXAMPLE 15

1-(4-((3-Methylureidopyridin-4-yl)methoxy)naphthalen-1-yl)-3-(3-tert-butyl-1-p-tolyl-1H-pyrazol-5-yl)urea

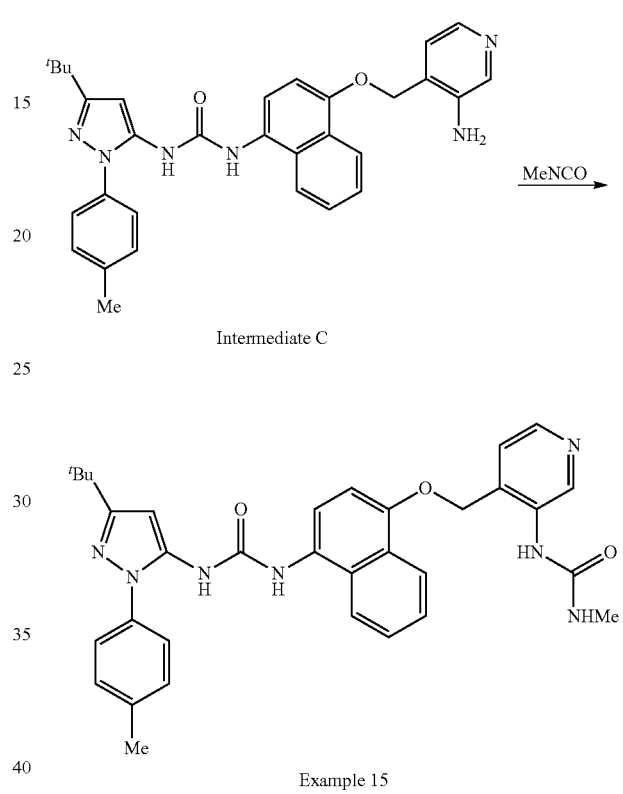

Example 15

Methyl isocyanate (8.5 μl, 0.14 mmol) was added to a solution of 1-(4-((3-aminopyridin-4-yl)methoxy)naphthalen-1-yl)-3-(3-tert-butyl-1-p-tolyl-1H-pyrazol-5-yl)urea (Intermediate C) (50 mg, 0.10 mmol) in pyridine (1.0 mL). The reaction mixture was stirred for 2 hr at RT and a further portion of methyl isocyanate (8.5 μl, 0.14 mmol) was added and stirring continued for 72 hr at RT. The solvent was removed in vacuo and the crude product was purified by column chromatography (4 g, 10-25% MeOH in DCM, gradient elution). The crude product fractions were combined and triturated with DCM (20 mL). The solid was filtered off to afford 1-(4-((3-methylureidopyridin-4-yl)methoxy)naphthalen-1-yl)-3-(3-tert-butyl-1-p-tolyl-1H-pyrazol-5-yl)urea (Example 15) (8 mg, 14%): m/z 578 (M+H)⁺ (ES⁺). ¹H NMR (400 MHz, DMSO-d₆) δ: 1.27 (9H, s), 2.39 (3H, s), 2.68 (3H, d), 5.27 (2H, s), 6.35 (1H, s), 6.53 (1H, m), 6.98 (1H, d), 7.35 (2H, d), 7.45 (2H, d), 7.65-7.52 (4H, m), 7.92 (1H, d), 8.16 (1H, s), 8.28 (2H, m), 8.61 (1H, s), 8.82 (1H, s), 8.88 (1H, s).

EXAMPLE 16

N-(4-((4-(3-(3-tert-Butyl-1-p-tolyl-1H-pyrazol-5-yl)ureido)naphthalen-1-yloxy)methyl)pyridin-3-yl)-2-methoxyacetamide

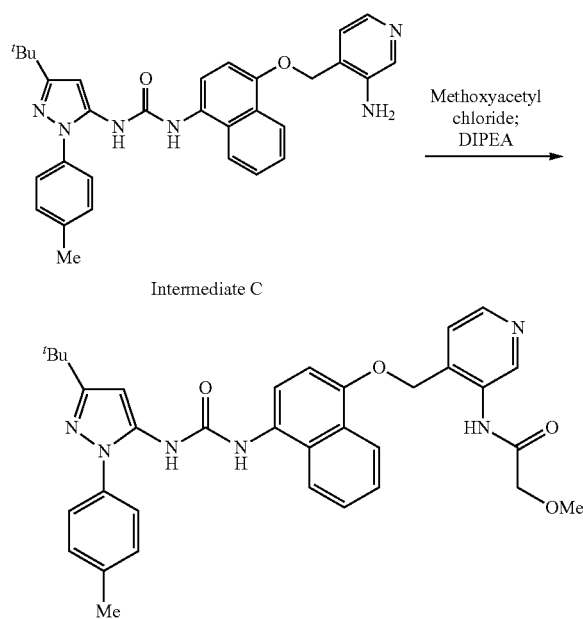

To a solution of 1-(4-((3-aminopyridin-4-yl)methoxy)naphthalen-1-yl)-3-(3-tert-butyl-1-p-tolyl-1H-pyrazol-5-yl)urea (Intermediate C) (50 mg, 0.10 mmol) and DIPEA (33.5 µl, 0.19 mmol) in anhydrous DCM (1.0 mL) and anhydrous DMF (0.1 mL) was added methoxyacetyl chloride (10 µl, 0.11 mmol). The reaction mixture was stirred for 12 hr at RT. LC-MS indicated 50% conversion to the desired product. Methoxyacetyl chloride (10 µl, 0.11 mmol) was added and the reaction mixture was stirred at RT for a further 5 hr; LC-MS indicated the reaction was nearing completion. A further portion of methoxyacetyl chloride (8 µl, 0.09 mmol) was added, and after 2 hr, LC-MS indicated the reaction had reached completion. 1% $NH_3$ In MeOH (10 mL) was added and the reaction mixture was stirred for 20 min at RT. The solvents were removed in vacuo to afford a purple oily solid. This was dissolved in MeOH (2.0 mL) and 3 drops of AcOH were added. The solution was subjected to SCX capture and release, eluting the product with 1% $NH_3$ in MeOH. The solvent was removed in vacuo and the residue was triturated with diethyl ether (10 mL) to afford N-(4-((4-(3-(3-tert-butyl-1-p-tolyl-1H-pyrazol-5-yl)ureido)naphthalen-1-yloxy)methyl)pyridin-3-yl)-2-methoxyacetamide (Example 16) as a light purple solid (24 mg, 41%) m/z 593 $(M+H)^+$ $(ES^+)$. $^1H$ NMR (400 MHz, DMSO-$d_6$) δ: 1.27 (9H, s), 2.39 (3H, s), 3.31 (3 H, s (obscured by DHO peak)), 4.06 (2H, s), 5.34 (2H, s), 6.35 (1H, s), 6.96 (1H, d), 7.35 (2H, d), 7.43 (2H, d), 7.64-7.54 (4H, m), 7.93 (1H, d), 8.29 (1H, dd), 8.45 (1H, d), 8.58 (1H, s), 8.70 (1H, s), 8.79 (1H, s), 9.76 (1H, s).

EXAMPLE 17

N-(4-((4-(3-(3-tert-Butyl-1-p-tolyl-1H-pyrazol-5-yl)ureido)naphthalen-1-yloxy)methyl)pyridin-3-yl)-2-(2-methoxyethoxy)acetamide

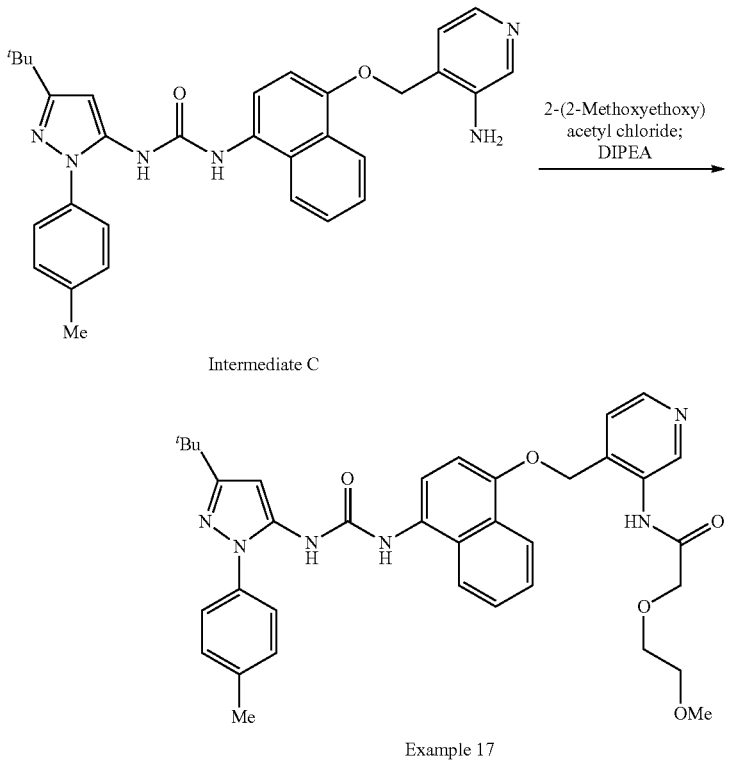

To a solution of 1-(4-((3-aminopyridin-4-yl)methoxy) naphthalen-1-yl)-3-(3-tert-butyl-1-p-tolyl-1H-pyrazol-5-yl) urea (Intermediate C) (50 mg, 0.10 mmol) and DIPEA (33.5 μl, 0.19 mmol) in anhydrous DCM (1.0 mL) and anhydrous DMF (0.2 mL) was added 2-(2-methoxyethoxy)acetyl chloride (15 μl, 0.11 mmol). The reaction mixture was stirred for 12 hr at RT. LC-MS indicated 50% conversion to the desired product. 2-(2-methoxyethoxy)acetyl chloride (15 μl, 0.11 mmol) was added and the reaction mixture stirred at RT. After 6 hr, LC-MS indicated the reaction had gone to completion. MeOH (2.0 mL) and AcOH (5 drops) were added and the reaction mixture was subjected to SCX capture and release, eluting with 1% $NH_3$ in MeOH. The solvent was removed in vacuo and the crude material purified by column chromatography (4 g, 0-10% MeOH in EtOAc, gradient elution) to afford N-(4-((4-(3-(3-tert-butyl-1-p-tolyl-1H-pyrazol-5-yl) ureido)naphthalen-1-yloxy)methyl)pyridin-3-yl)-2-(2-methoxyethoxy)acetamide (Example 17) as a white solid (27 mg, 43%): m/z 637 $(M+H)^+$ $(ES^+)$. $^1H$ NMR (400 MHz, DMSO-$d_6$) δ: 1.27 (9H, s), 2.39 (3H, s), 3.18 (3H, s), 3.36 (2H, m), 3.61 (2H, m), 4.14 (2H, s), 5.33 (2H, s), 6.35 (1H, s), 6.97 (1H, d), 7.35 (2H, d), 7.43 (2H, d), 7.67-7.55 (4H, m), 7.92 (1H, d), 8.27 (1H, d), 8.46 (1H, d), 8.58 (1H, s), 8.74 (1H, s), 8.80 (1H, s), 9.65 (1H, s).

Intermediate D: 1-(4-(2-(2-Aminopyridin-4-yl) ethoxy)naphthalen-1-yl)-3-(3-tert-butyl-1-p-tolyl-1 H-pyrazol-5-yl)urea

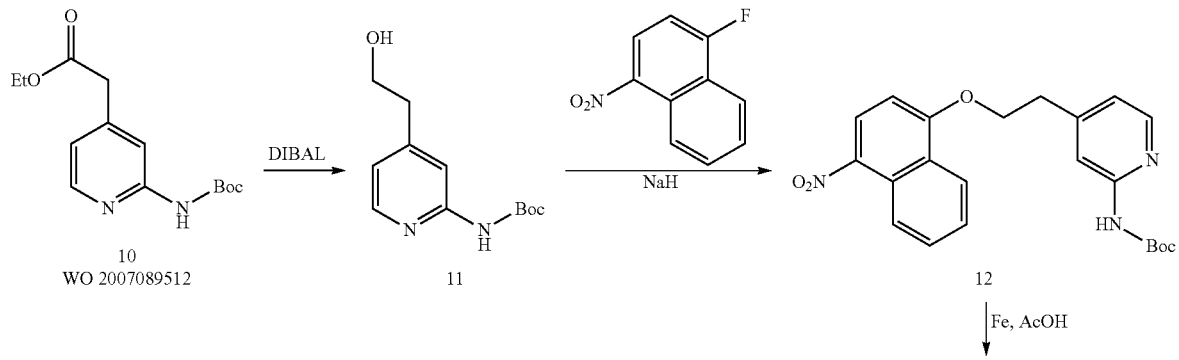

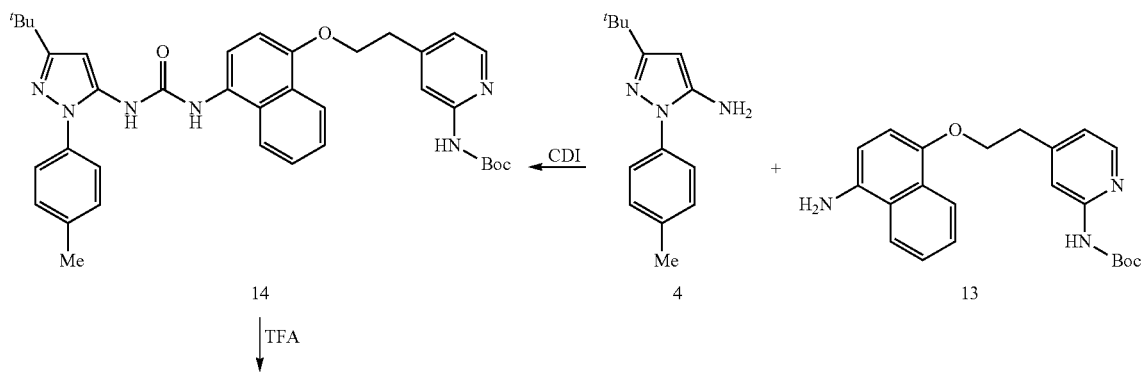

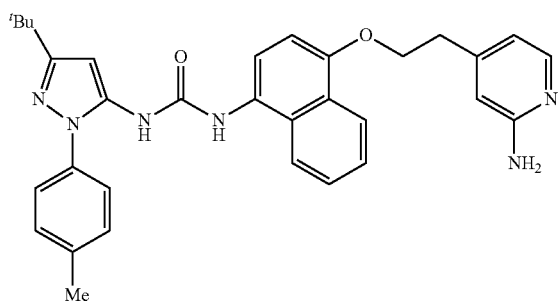

Intermediate D tert-Butyl 4-(2-hydroxyethyl)pyridin-2-ylcarbamate (11)

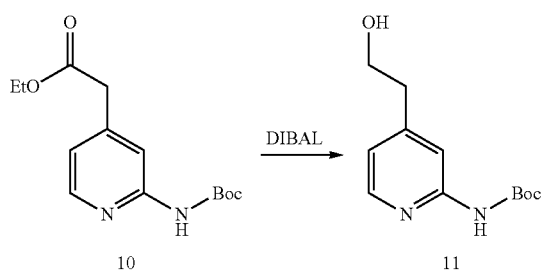

To a solution of ethyl 2-(2-(tert-butoxycarbonylamino)pyridin-4-yl)acetate (10) (WO 2007089512) (10.0 g, 35.7 mmol) under nitrogen in THF (100 mL), at −78° C., was added DIBAL (1M solution in THF, 71.3 mL, 71.3 mmol) over 1 hr. The reaction mixture was stirred at −78 to −60° C. for 40 min and then warmed to −15° C. over 1 hr. The solution was re-cooled to −78° C. and treated with further DIBAL (1M solution in THF, 35 mL, 35.7 mmol). The mixture was allowed to warm to −40° C. and stirred for 1 hr. Water (10 mL) was added cautiously to quench the reaction followed by $MgSO_4$ (20 g) and the solids removed by filtration. The filtrate was concentrated to dryness under reduced pressure and the residue subjected to column chromatography (330 g), eluting with 65% EtOAc in hexanes to give tert-butyl 4-(2-hydroxyethyl)pyridin-2-ylcarbamate (11) (6.00 g, 64%) as a yellow solid: m/z 239 (M+H)$^+$ (ES$^+$).

tert-Butyl 4-(2-(4-nitronaphthalen-1-yloxy)ethyl)pyridin-2-ylcarbamate (12)

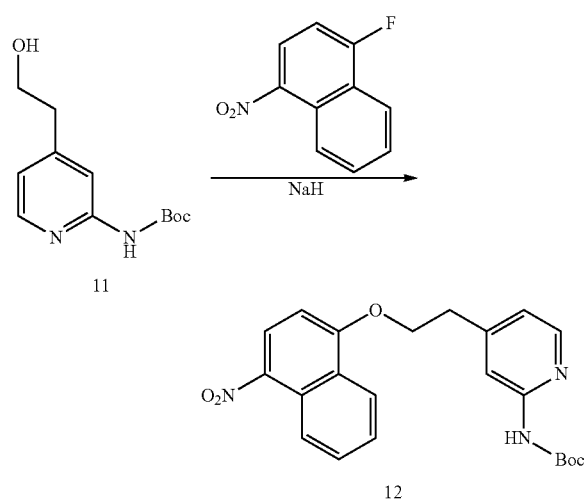

To a solution of tert-butyl 4-(2-hydroxyethyl)pyridin-2-ylcarbamate (11) (6.00 g, 25.2 mmol) in THF (70 mL) was added sodium hydride (2.52 g, 63.0 mmol, 60 wt %) at 0° C. The bright yellow suspension was stirred for 20 min at 0° C. before the addition of 1-fluoro-4-nitronaphthalene (4.81 g, 25.2 mmol) in a single portion. After stirring at RT for 2 hr, water (100 mL) was added followed by EtOAc (100 mL). The solid formed between the layers was collected by filtration and the organic phase was washed with saturated aq $NaHCO_3$ (100 mL), brine (100 mL) and dried. The volatiles were removed to give an orange solid. The solids were combined and triturated from MeOH (50 mL) to give tert-butyl 4-(2-(4-nitronaphthalen-1-yloxy)ethyl)pyridin-2-ylcarbamate (12) as a yellow solid (11.0 g, 98%): m/z 410 (M+H)$^+$ (ES$^+$).

tert-Butyl 4-(2-(4-aminonaphthalen-1-yloxy)ethyl)pyridin-2-ylcarbamate (13)

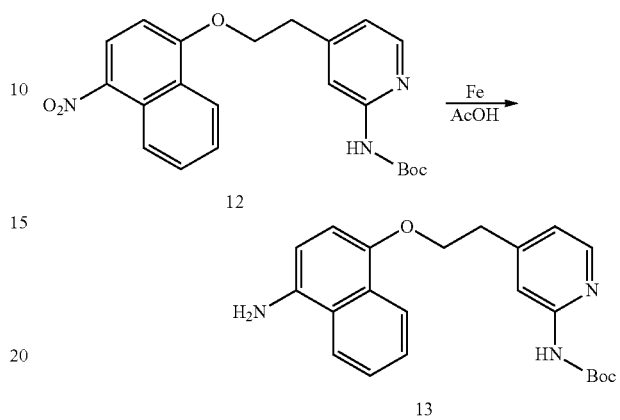

tert-Butyl 4-(2-(4-nitronaphthalen-1-yloxy)ethyl)pyridin-2-ylcarbamate (11) (5.20 g, 12.7 mmol) and iron mesh (4.30 g, 76 mmol) were suspended in a mixture of AcOH and EtOH (1:2, 120 mL). The suspension was placed in a pre-heated oil bath at 60° C. and stirred rapidly until the reaction was judged to be complete by LC-MS. The mixture was cooled to RT, poured carefully onto saturated aq $NaHCO_3$ (1000 mL) and extracted with EtOAc (500 mL×2). The combined organic layers were washed with further saturated aq $NaHCO_3$ (1000 mL), water (1000 mL), brine (1000 mL) and dried. This was filtered and evaporated to give tert-butyl 4-(2-(4-aminonaphthalen-1-yloxy)ethyl)pyridin-2-ylcarbamate (13) as a yellow oil (5.00 g, 95%): m/z 380 (M+H)$^+$ (ES$^+$).

tert-Butyl-4-(2-(4-(3-(3-tert-butyl-1-p-tolyl-1H-pyrazol-5-yl)ureido)naphthalen-1-yloxy)ethyl)pyridin-2-ylcarbamate (14)

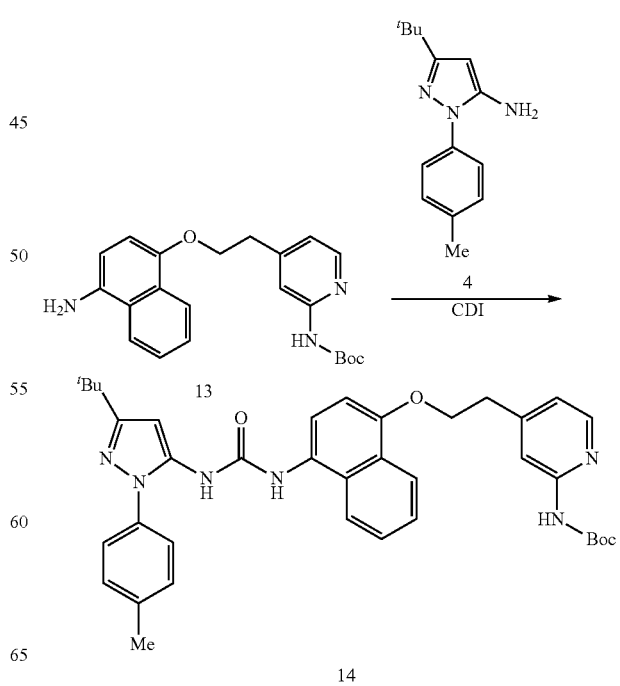

To a suspension of CDI (3.00 g, 18.18 mmol) in DCM (15 mL) was added a solution of 3-tert-butyl-1-p-tolyl-1H-pyrazol-5-amine (4) (WO 2000043384) (4.17 g, 18.18 mmol) in DCM (40 mL) over 1.5 hrs. After stirring at RT for 2 hr, a solution of tert-butyl 4-(2-(4-aminonaphthalen-1-yloxy) ethyl)pyridin-2-ylcarbamate (13) (3.00 g, 7.91 mmol) in DCM (15 mL) was added. After stirring overnight, the solution was diluted with MeOH (10 mL) and absorbed onto silica gel (30 g) and subjected to column chromatography (330 g) eluting with 30% to 100% EtOAc in iso-hexane and then 0% to 6% MeOH in EtOAc to give tert-butyl-4-(2-(4-(3-(3-tert-butyl-1-p-tolyl-1H-pyrazol-5-yl)ureido)naphthalen-1-yloxy)ethyl)pyridin-2-ylcarbamate (13) as a beige solid (4.20 g, 80%): m/z 635 (M+H)$^+$ (ES$^+$).

Intermediate D: 1-(4-(2-(2-Aminopyridin-4-yl) ethoxy)naphthalen-1-yl)-3-(3-tert-butyl-1-p-tolyl-1H-pyrazol-5-yl)urea

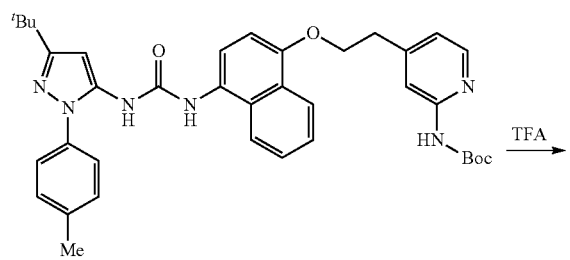

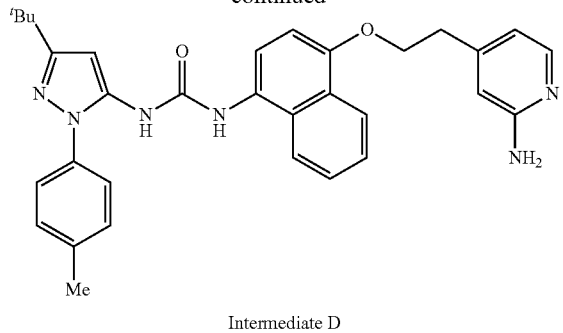

Intermediate D

To a suspension of tert-butyl-4-(2-(4-(3-(3-tert-butyl-1-p-tolyl-1H-pyrazol-5-yl)ureido) naphthalen-1-yloxy)ethyl)pyridin-2-ylcarbamate (14) (1.35 g, 2.20 mmol) in DCM (10 mL) was added TFA (10 mL). After stirring at RT for 2 hr, the volatiles were evaporated and the residue was taken up in EtOAc (50 mL) and extracted with saturated aq NaHCO$_3$ (50 mL). The layers were separated; the organic was washed with brine (50 mL), dried and evaporated to give 1-(4-(2-(2-aminopyridin-4-yl)ethoxy)naphthalen-1-yl)-3-(3-tert-butyl-1-p-tolyl-1H-pyrazol-5-yl)urea (Intermediate D) as a pale pink solid (1.20 g, 100%): m/z 535 (M+H)$^+$ (ES$^+$).

EXAMPLE 18

N-(4-(2-(4-(3-(3-tert-Butyl-1-p-tolyl-1H-pyrazol-5-yl)ureido)naphthalen-1-yloxy)ethyl)pyridin-2-yl)-2-methoxyacetamide

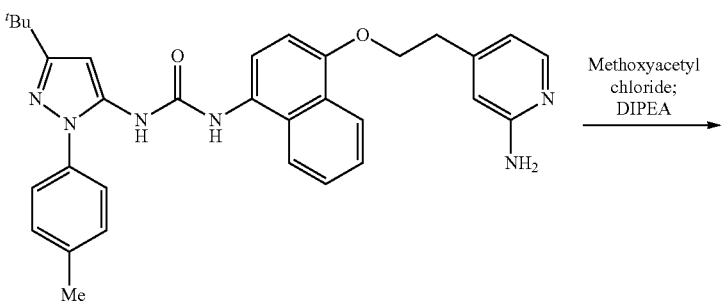

Intermediate D

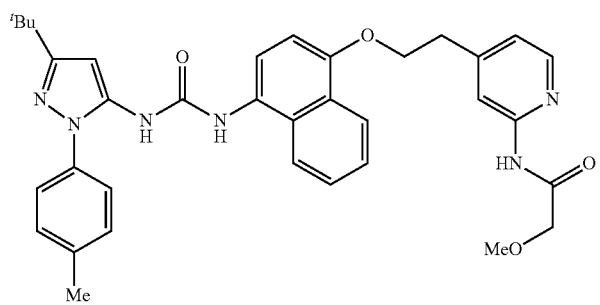

Example 18

To a suspension of 1-(4-(2-(2-aminopyridin-4-yl)ethoxy) naphthalen-1-yl)-3-(3-tert-butyl-1-p-tolyl-1H-pyrazol-5-yl) urea (Intermediate D) (35 mg, 0.065 mmol) in DCM (0.5 mL) was added DIPEA (23 μl, 0.131 mmol) and methoxyacetyl chloride (7 μl, 0.072 mmol). The mixture was stirred at RT, until judged to be complete by LC-MS; diluted with saturated aq NaHCO$_3$ (1.5 mL) and the layers were separated through a phase separator cartridge. The organics were collected, evaporated under reduced pressure and the residue subjected to SCX capture and release. The resulting residue was purified further by preparative RP HPLC to give N-(4-(2-(4-(3-(3-tert-butyl-1-p-tolyl-1H-pyrazol-5-yl)ureido)naphthalen-1-yloxy)ethyl)pyridin-2-yl)-2-methoxyacetamide (Example 18) as a white solid (5 mg, 13%): m/z 607 (M+H)$^+$ (ES$^+$). $^1$H NMR (400 MHz, DMSO-d$_6$) δ: 1.26 (9H, s), 2.37 (3H, s), 3.20 (2H, t), 3.37 (3H, s), 4.06 (2H, s), 4.38 (2H, t), 6.33 (1 H, s), 6.95 (1H, d), 7.19 (1H, dd), 7.33 (2H, m), 7.42-7.47 (3H, m), 7.54 (1H, m), 7.59 (1H, d), 7.87 (1H, d), 8.12 (1H, d), 8.18 (1H, bs), 8.23 (1H, d), 8.67 (1H, s), 8.84 (1H, s), 9.89 (1 H, s).

EXAMPLE 19

N-(4-(2-(4-(3-(3-tert-Butyl-1-p-tolyl-1H-pyrazol-5-yl)ureido)naphthalen-1-yloxy)ethyl)pyridin-2-yl)-2-(2-methoxyethoxy)acetamide To a suspension of 1-(4-(2-(2-aminopyridin-4-yl)ethoxy) naphthalen-1-yl)-3-(3-tert-butyl-1-p-tolyl-1H-pyrazol-5-yl) urea (Intermediate D) (35 mg, 0.065 mmol) in DCM (0.5 mL) was added DIPEA (23 μl, 0.131 mmol) and 2-(2-methoxy) ethoxyacetyl chloride (11 mg, 0.072 mmol). The mixture was stirred at RT, until judged to be complete by LC-MS; diluted with saturated aq NaHCO$_3$ (1.5 mL) and the layers were separated through a phase separator cartridge. The organics were collected, evaporated under reduced pressure and the residue subjected to SCX capture and release. The resulting residue was purified further by preparative RP HPLC to give N-(4-(2-(4-(3-(3-tert-butyl-1-p-tolyl-1H-pyrazol-5-yl)ureido)naphthalen-1-yloxy)ethyl)pyridin-2-yl)-2-(2-methoxyethoxy)acetamide (Example 19) as an off white solid (13 mg, 31%): m/z 651 (M+H)$^+$ (ES$^+$). $^1$H NMR (400 MHz, DMSO-d$_6$) δ: 1.26 (9H, s), 2.38 (3H, s), 3.21 (2H, t), 3.28 (3H, s), 3.49-3.51 (2H, m), 3.66-3.68 (2H, m), 4.13 (2H, s), 4.38 (2H, t), 6.34 (1H, s), 6.95 (1H, d), 7.19 (1H, dd), 7.34 (2H, m), 7.41-7.48 (3H, m), 7.51-7.56 (1H, m), 7.59 (1H, d), 7.87 (1H, d), 8.11-8.14 (1H, dd), 8.20 (1H, bs), 8.23-8.25 (1H, dd), 8.55 (1H, s), 8.75 (1H, s), 9.83 (1H, s).

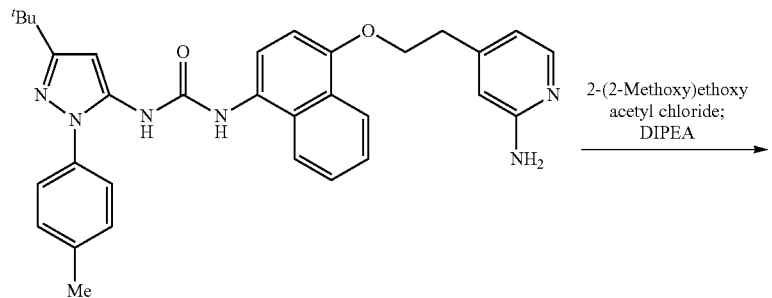

2-(2-Methoxy)ethoxy acetyl chloride; DIPEA

Intermediate D

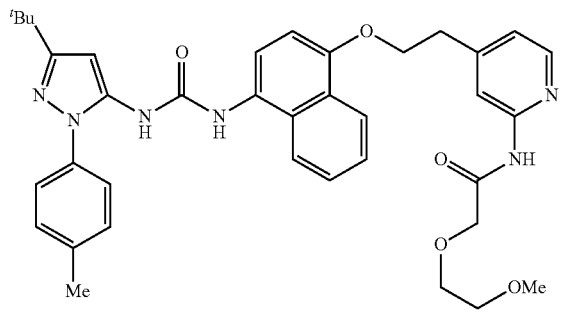

Example 19

EXAMPLE 20

4-(2-(4-(3-(3-tert-Butyl-1-p-tolyl-1H-pyrazol-5-yl)ureido)naphthalen-1-yloxy)ethyl)-1-methyl-3-(pyridin-2-yl)urea

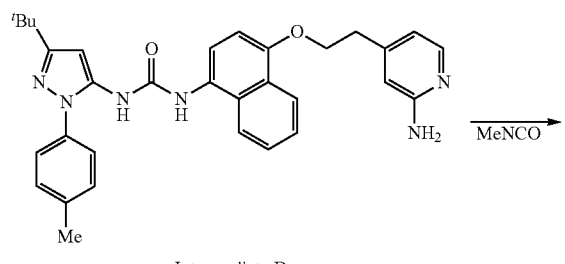

Intermediate D

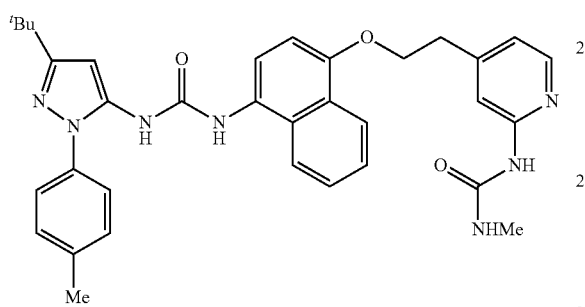

Example 20

To a solution of 1-(4-(2-(2-aminopyridin-4-yl)ethoxy)naphthalen-1-yl)-3-(3-tert-butyl-1-p-tolyl-1H-pyrazol-5-yl)urea (7) (Intermediate D) (50 mg, 0.094 mmol) in pyridine (1.0 mL) was added methyl isocyanate (5.34 mg, 0.094 mmol). The mixture was stirred at RT for 72 hr and the solvent was evaporated under reduced pressure. The resulting residue was triturated from MeOH (5.0 mL) to give 4-(2-(4-(3-(3-tert-butyl-1-p-tolyl-1H-pyrazol-5-yl)ureido)naphthalen-1-yloxy)ethyl)-1-methyl-3-(pyridin-2-yl))urea (Example 20) as an off white solid (7 mg, 13%): m/z 592 (M+H)$^+$ (ES$^+$). $^1$H NMR (400 MHz, DMSO-d$_6$) δ: 1.26 (9H, s), 2.38 (3H, s), 3.13 (2H, t), 3.31 (3H, s, obscured by H$_2$O), 4.32 (2H, t), 6.34 (1H, s), 6.93 (1H, d), 7.34 (2H, m), 7.40-7.48 (6H, m), 7.53-7.57 (1H, m), 7.61 (1H, d), 7.81-7.83 (2H, d), 7.86-7.89 (1H, d), 8.02-8.04 (1H, dd), 8.55 (1H, s), 8.75 (1H, s).

EXAMPLE 21

4-(2-(4-(3-(3-tert-Butyl-1-p-tolyl-1H-pyrazol-5-yl)ureido)naphthalen-1-yloxy)ethyl)-3-(pyridin-2-yl)urea

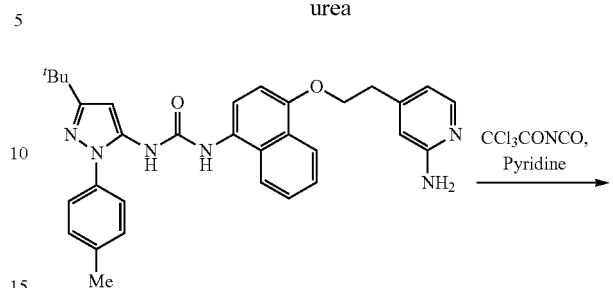

Intermediate D

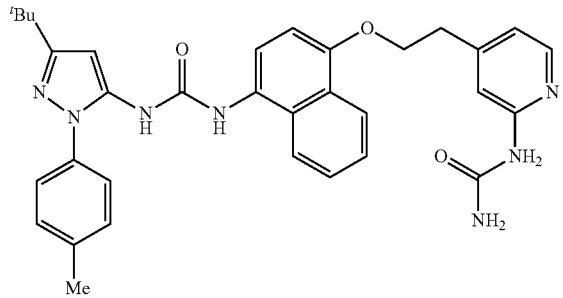

Example 21

To a solution of 1-(4-(2-(2-aminopyridin-4-yl)ethoxy)naphthalen-1-yl)-3-(3-tert-butyl-1-p-tolyl-1H-pyrazol-5-yl)urea (7) (Intermediate D) (50 mg, 0.094 mmol) in pyridine (1.0 mL) was added trichloroacetylisocyanate (12 µl, 0.103 mmol). The mixture was stirred at RT until judged to be complete by LC-MS and solvent was evaporated under reduced pressure. The resulting residue was subjected to SCX capture and release and triturated from DCM (10 mL) to give 4-(2-(4-(3-(3-tert-butyl-1-p-tolyl-1H-pyrazol-5-yl)ureido)naphthalen-1-yloxy)ethyl)-3-(pyridin-2-yl)urea (Example 21) as an off white solid (25 mg, 44%): m/z 578 (M+H)$^+$ (ES$^+$). $^1$H NMR (400 MHz, DMSO-d$_6$) δ: 1.26 (9H, s), 2.38 (3H, s), 3.12 (2H, t), 4.35 (2H, t), 6.34 (1H, s), 6.94-6.99 (2H, m), 7.19 (1H, dd), 7.33-7.35 (2H, m), 7.41-7.50 (5H, m), 7.52-7.56 (1H, m), 7.60 (1H, d), 7.87 (1H, d), 8.09-8.13 (2H, m), 8.54 (1H, s), 8.75 (1H, s), 9.08 (1H, s).

Intermediate E: 1-(4-(2-(3-Aminopyridin-4-yl)ethoxy)naphthalen-1-yl)-3-(3-tert-butyl-1-p-tolyl-1H-pyrazol-5-yl)urea

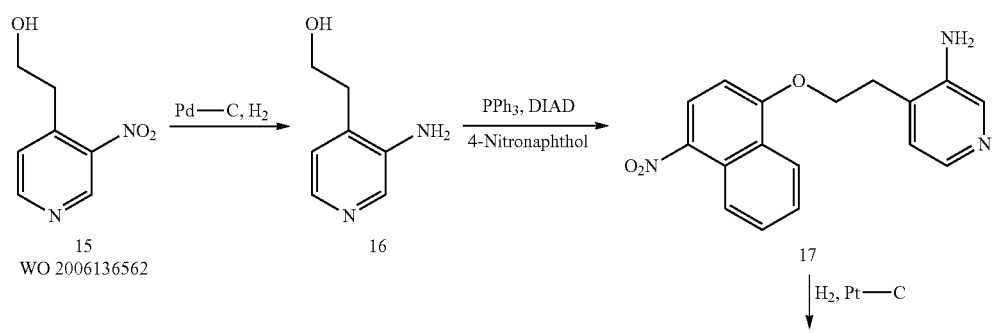

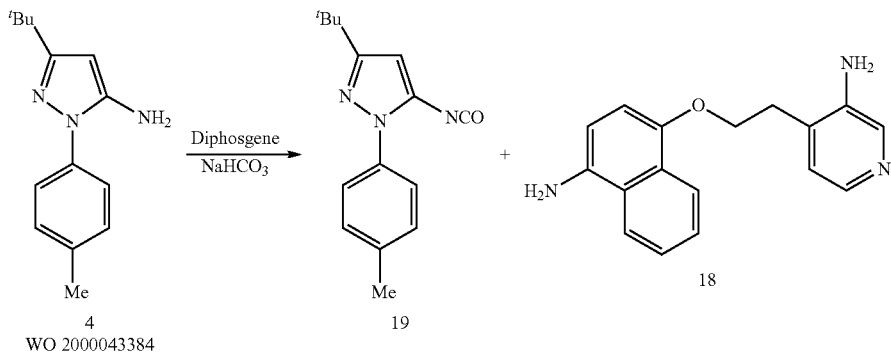

Intermediate E 2-(3-Aminopyridin-4-yl)ethanol (16)

4-(2-(4-Nitronaphthalen-1-yloxy)ethyl)pyridin-3-amine (17)

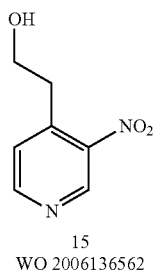

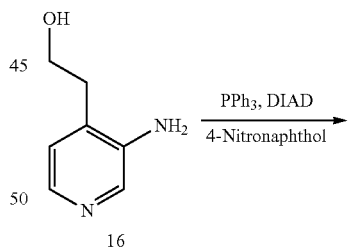

2-(3-Nitropyridin-4-yl)ethanol (15) (WO 2006136562) (2.00 g, 11.89 mmol) in MeOH (150 mL) was passed through a Thales H-cube at 2.0 mL·min$^{-1}$ using Pd/C Cat-Cart (55 mm) in controlled mode at 30° C., 30 bar. Analysis by LC-MS showed a significant amount of starting material was still present. The solution was passed through the H-cube a second time at 2.0 mL·min$^{-1}$ in full hydrogen mode at RT, and again at 2.0 mL·min$^{-1}$ in full hydrogen mode at 40° C. Evaporation of the volatiles gave 2-(3-Aminopyridin-4-yl)ethanol (16) as a purple oil (1.30 g, 81%): m/z 139 (M+H)$^+$ (ES$^+$).

To a solution of 4-nitronaphthol (0.95 g, 5.00 mmol), PPh$_3$ (1.97 g, 7.50 mmol) and 2-(3-aminopyridin-4-yl)ethanol (16) (1.04 g, 7.50 mmol) in THF (20 mL) was added dropwise DIAD (590 μl, 3.75 mmol) at −15° C. The mixture was stirred for 1 hr at RT and the volatiles removed in vacuo. The residues was absorbed on silica (20 g) and purified by column chromatography (80 g) gradient elution with 50-100% EtOAc/iso-hexane and final elution with 5% MeOH/EtOAc to give 4-(2-(4-nitronaphthalen-1-yloxy)ethyl)pyridin-3-amine a yellow solid (17) (1.36 g, 88%): m/z 310 (M+H)+ (ES+).

4-(2-(4-Aminonaphthalen-1-yloxy)ethyl)pyridin-3-amine (18)

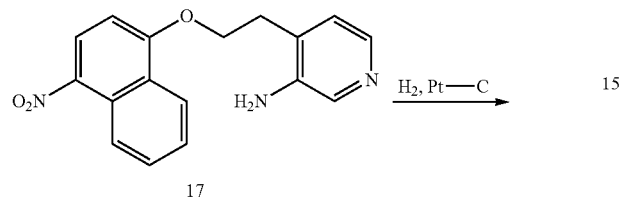

A solution of 4-(2-(4-nitronaphthalen-1-yloxy)pyridin-3-amine (17) (700 mg, 2.263 mmol) in a mixture of MeOH (50 mL), EtOAc (25 mL), and DCM (25 mL) was passed through a Thales H-cube (10% Pt/C 30 mm, 1.0 mL·min⁻¹, at 40° C., full hydrogen mode). The solvent was removed in vacuo to give 4-(2-(4-aminonaphthalen-1-yloxy)ethyl)pyridin-3-amine (18) as a brown solid (612 mg, 92%). m/z 280 (M+H)+ (ES+).

3-tert-Butyl-5-isocyanato-1-p-tolyl-1H-pyrazole (19)

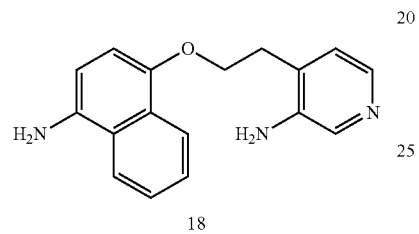

To a solution of 3-tert-butyl-1-p-tolyl-1H-pyrazol-5-amine (4) (WO 2000043384) (1.00 g, 4.36 mmol) in DCM (90 mL) was added a saturated aq solution of NaHCO₃ (60 mL). The mixture was stirred vigorously, cooled to 0° C. and diphosgene (2.1 mL, 17.4 mmol) was added in a single portion. After stirring for 1 hr at RT, the layers were separated and the organics dried and evaporated to give a brown oil. The oil was triturated with iso-hexane (5.0 mL) and the solid filtered. The filtrate was concentrated in vacuo to give 3-tert-butyl-5-isocyanato-1-p-tolyl-1H-pyrazole (19) as a light brown oil (1.00 g, 3.92 mmol, 90%). m/z 288 (in MeOH) (M+H+MeOH)+ (ES+).

Intermediate E: 1-(4-(2-(3-Aminopyridin-4-yl)ethoxy)naphthalen-1-yl)-3-(3-tert-butyl-1-p-tolyl-1H-pyrazol-5-yl)urea

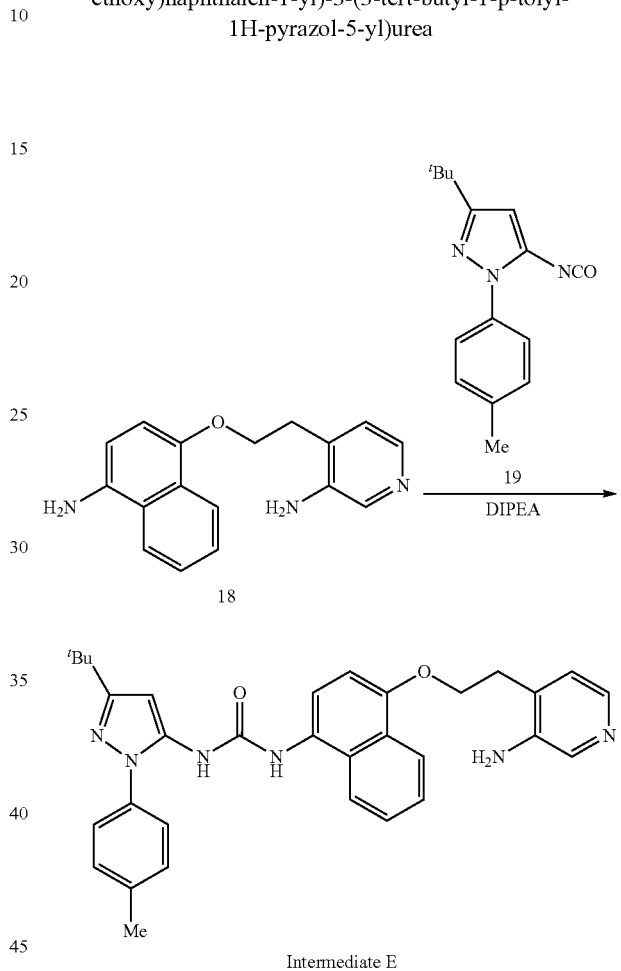

Intermediate E

A solution of 3-tert-butyl-5-isocyanato-1-p-tolyl-1H-pyrazole (19) (530 mg, 2.076 mmol) in THF (2.0 mL) was added to a solution of 4-(2-(4-aminonaphthalen-1-yloxy)ethyl)pyridin-3-amine (18) (580 mg, 2.076 mmol) and DIPEA (1085 µl, 6.23 mmol) in THF (10 mL) and MeCN (1.0 mL) the reaction mixture stirred at RT overnight. The mixture was poured into brine (25 mL) and extracted with EtOAc (2×25 mL), dried, filtered and the solvent removed in vacuo. The product was pre-adsorbed onto hyflo (10 g), and purified by reverse phase column chromatography (40 g, C18 (from Silicycle), acetonitrile/water, 0 to 100%) and the product fractions concentrated in vacuo to give 1-(4-(2-(3-aminopyridin-4-yl)ethoxy)naphthalen-1-yl)-3-(3-tert-butyl-1-p-tolyl-1H-pyrazol-5-yl)urea (Intermediate E) as an off white solid (410 mg, 36%). m/z 535 (M+H)+ (ES+).

EXAMPLE 22

N-(4-(2-(4-(3-(3-tert-Butyl-1-p-tolyl-1H-pyrazol-5-yl)ureido)naphthalen-1-yloxy)ethyl)pyridin-3-yl)-2-(2-methoxyethoxy)acetamide

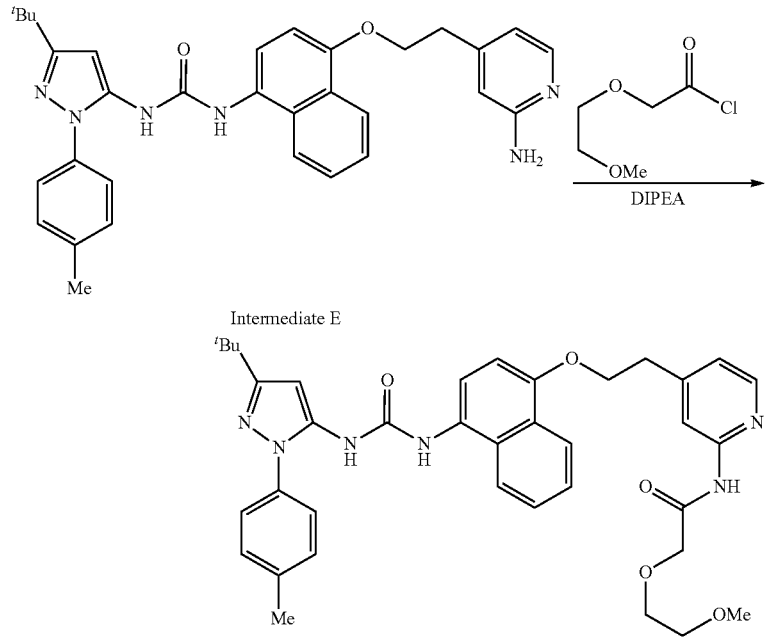

Example 22

To 1-(4-(2-(3-aminopyridin-4-yl)ethoxy)naphthalen-1-yl)-3-(3-tert-butyl-1-p-tolyl-1H-pyrazol-5-yl)urea (Intermediate E) (50 mg, 0.094 mmol) and DMAP (5.71 mg, 0.047 mmol) in DCM (3.0 mL) was added 2-(2-methoxyethoxy)acetyl chloride (30 µl, 0.281 mmol) at 0° C. and the reaction mixture stirred at RT for 1.5 hr. The solvent was removed in vacuo and the residue subjected to SCX capture and release eluting with 1% $NH_3$ in MeOH solution. The residue was purified by column chromatography (4.0 g) gradient elution with 0-8% MeOH in DCM and the product fractions concentrated in vacuo to give N-(4-(2-(4-(3-(3-tert-butyl-1-p-tolyl-1H-pyrazol-5-yl)ureido)naphthalen-1-yloxy)ethyl)pyridin-3-yl)-2-(2-methoxyethoxy)acetamide (Example 22) as a light purple solid (35 mg, 56%): m/z 651 (M+H)$^+$ (ES$^+$). $^1$H NMR (400 MHz, DMSO-$d_6$) δ: 1.25 (9H, s), 2.40 (3H, s), 3.26 (5H, m), 3.50 (2H, m), 3.70 (2H, m), 4.15 (2H, s), 4.40 (2H, t), 6.35 (1H, s), 6.98 (1H, d), 7.35 (2H, m), 7.42 (2H, m), 7.50 (3H, m), 7.62 (1H, d), 7.87 (1H, d), 8.07 (1H, dd), 8.36 (1H, d), 8.56 (1H, br s), 8.60 (1H, s), 8.76 (1H, br s), 9.55 (1H, br s).

Intermediate F: 1-(4-(1-(2-aminopyridin-4-yl)ethoxy)naphthalen-1-yl)-3-(3-tert-butyl-1-p-tolyl-1H-pyrazol-5-yl)urea

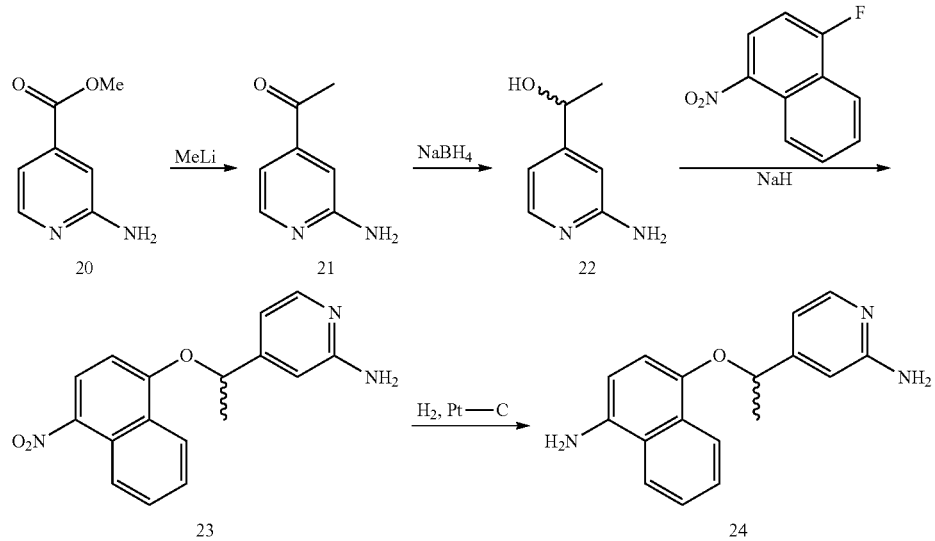

-continued

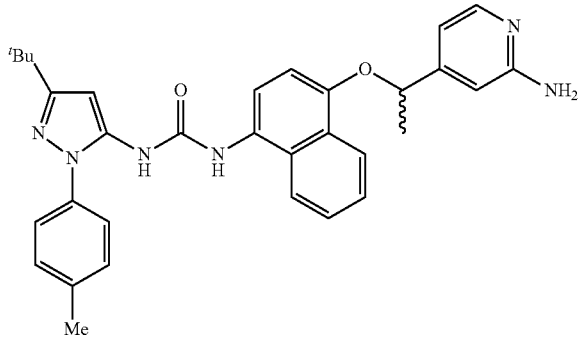

Intermediate F

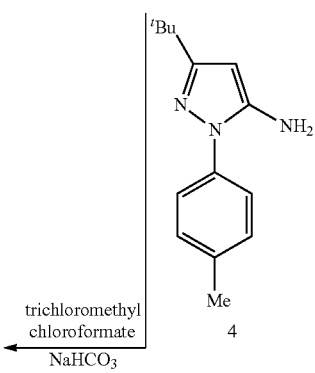

trichloromethyl chloroformate
NaHCO₃

1-(2-Aminopyridin-4-yl)ethanone (21)

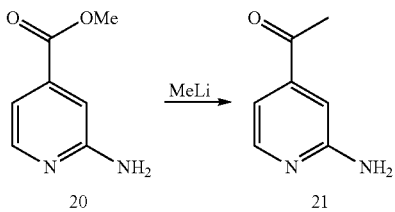

To a stirred solution of methyl-2-aminopyridine-4-carboxylate (20) (1.00 g, 6.57 mmol) in THF (100 mL), at −78° C. under nitrogen, was added methyllithium (1.6 M in diethyl ether, 16.43 ml, 26.3 mmol), over 10 min. After a further 30 min at −78° C., the viscous reaction mixture was warmed to 0° C. After a further 3 hr, the reaction was quenched at 0° C. by the cautious addition of iso-propanol (8.0 mL). The mixture was warmed to RT, brine (200 mL) and EtOAc (150 mL) were added, and the layers were separated. The aqueous layer was extracted with EtOAc (100 mL×3), and the combined organic extracts were dried and the solvents removed under reduced pressure. The crude residue was purified by column chromatography (80 g) eluting with 0 to 8% MeOH in EtOAc, to give 1-(2-aminopyridin-4-yl)ethanone (21) (176 mg, 20%) as a yellow powder: m/z 137 (M+H)⁺ (ES⁺).

1-(2-Aminopyridin-4-yl)ethanol (20)

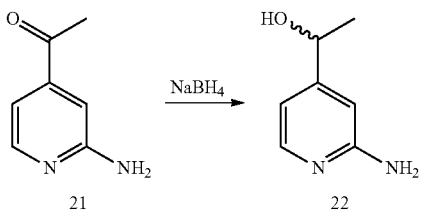

To a mixture of 1-(2-aminopyridin-4-yl)ethanone (21) (168 mg, 1.234 mmol) in MeOH (10 mL), under nitrogen at 0° C., was added sodium borohydride (46.7 mg, 1.234 mmol). The resulting reaction mixture was stirred at RT for 2 hr, and then the solvents were removed under reduced pressure. The residue was taken up into EtOAc (25 mL), and extracted with saturated aq NaHCO₃ solution (30 mL) and the layers separated. The aqueous layer was extracted with EtOAc (20 mL×2), and the combined organic extracts were washed with brine (30 mL), dried and the solvents removed under reduced pressure, to give 1-(2-aminopyridin-4-yl)ethanol (22) (77 mg, 45%) as a yellow oil: m/z 139 (M+H)⁺ (ES⁺).

4-(1-(4-Nitronaphthalen-1-yloxy)ethyl)pyridin-2-amine (23)

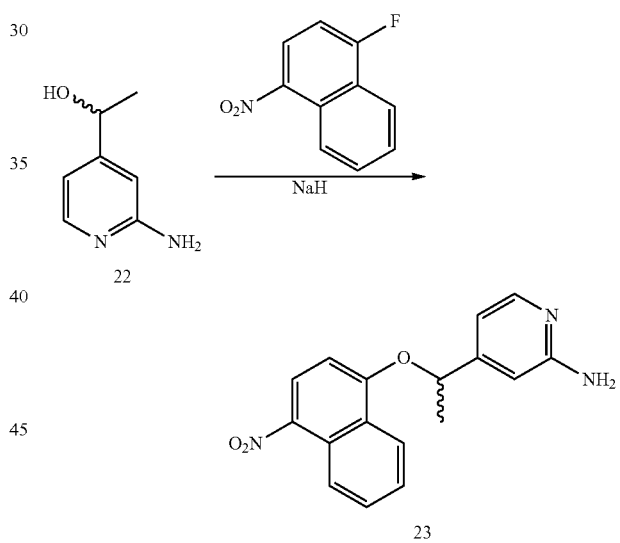

To a stirred solution of 1-(2-aminopyridin-4-yl)ethanol (22) (73 mg, 0.528 mmol) in DMF (1.5 mL), under nitrogen at 0° C., was added sodium hydride (32 mg, 0.793 mmol, 60 wt %). The resulting mixture was stirred at 0° C. for 40 min, and a solution of 1-fluoro-4-nitronaphthalene (101 mg, 0.528 mmol) in DMF (1.5 mL) was added dropwise. The resulting dark-red mixture was stirred at 0° C. for a further 5 min, and then at RT. After a further 40 min, the reaction was quenched by the addition of 1.0 mL of NH₄Cl solution. Water (20 mL) and EtOAc (20 mL) were added, and the layers were separated. The aqueous layer was extracted with EtOAc (15 mL×3). The combined organic extracts were washed with brine, dried and the solvents removed under reduced pressure. The crude material was purified by column chromatography (12 g), eluting with 0 to 80% EtOAc in iso-hexane, to give 4-(1-(4-nitronaphthalen-1-yloxy)ethyl)pyridin-2-amine (23) (94.6 mg, 57%) as an orange gum: m/z 310 (M+H)⁺ (ES⁺).

4-(1-(4-Aminonaphthalen-1-yloxy)ethyl)pyridin-2-amine (24)

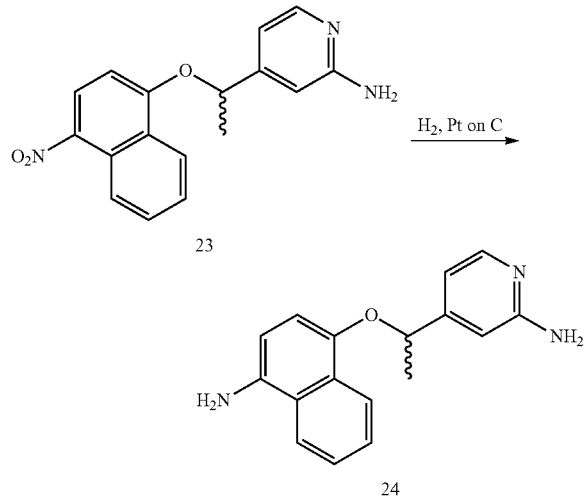

4-(1-(4-Nitronaphthalen-1-yloxy)ethyl)pyridin-2-amine (23) (91 mg, 0.294 mmol) in MeOH (15 mL) and AcOH (3.0 mL) was passed through a Thales H-cube (1.0 mL·min⁻¹, 30° C., 55 mm 10% Pt/C Cat-Cart, full hydrogen mode). The volatiles were removed under reduced pressure, leaving a purple solid, which was then subjected to SCX capture and release to give 4-(1-(4-aminonaphthalen-1-yloxy)ethyl)pyridin-2-amine (24) (81 mg, 99%) as a purple oil: m/z 280 (M+H)⁺ (ES⁺).

Intermediate F: 1-(4-(1-(2-Aminopyridin-4-yl)ethoxy)naphthalen-1-yl)-3-(3-tert-butyl-1-p-tolyl-1H-pyrazol-5-yl)urea

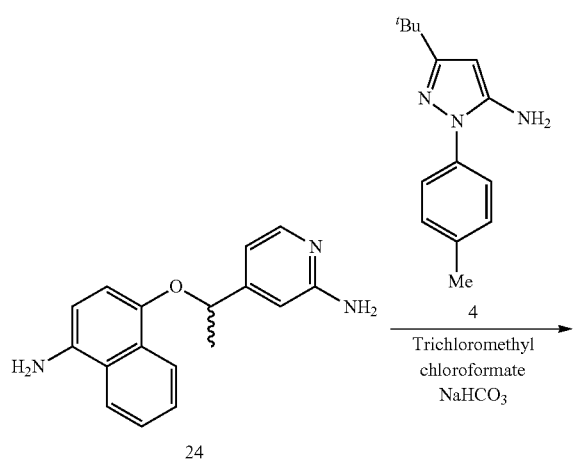

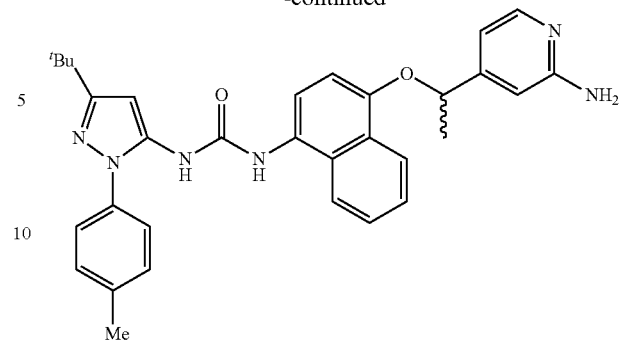

Intermediate F

To a solution of 3-tert-butyl-1-p-tolyl-1H-pyrazol-5-amine (4) (WO 2000043384) (57 mg, 0.250 mmol) in DCM (6.0 mL) was added a saturated aq NaHCO₃ solution (4.0 mL), and the mixture was stirred vigorously. The mixture was cooled to 0° C. and then trichloromethylchloroformate (0.091 ml, 0.750 mmol) was added in one portion. The resulting mixture was stirred at 0° C. for 1.5 hr. The layers were separated, the organic extract was dried and the solvents removed under reduced pressure to afford an oil, which was left drying under high vacuum, at 35° C. for a further 35 min. The resulting oil was taken up into THF (5.0 mL), and then added to 4-(1-(4-aminonaphthalen-1-yloxy)ethyl)pyridin-2-amine (24) (81 mg, 0.290 mmol). DIPEA (179 μl, 1.029 mmol) was added, and the reaction mixture was stirred at RT for 16 hr. Water (15 mL) and EtOAc (10 mL) were added to the reaction mixture and the layers were separated. The aqueous layer was extracted with EtOAc (15 mL). The combined organic extracts were washed with brine (20 mL), dried and the solvents removed under reduced pressure. The resulting residue was dissolved in MeOH (5.0 mL) and AcOH (2.0 mL) and subjected to SCX capture and release. The crude mixture was purified by column chromatography (12 g), eluting with 0 to 10% MeOH in DCM, to give 1-(4-(1-(2-aminopyridin-4-yl)ethoxy)naphthalen-1-yl)-3-(3-tert-butyl-1-p-tolyl-1H-pyrazol-5-yl)urea (Intermediate F) (63 mg, 38%) as a beige powder: m/z 535 (M+H)⁺ (ES⁺).

Intermediate G: 1-(4-(1-(2-Aminopyridin-4-yl)-2-methylpropan-2-yloxy)naphthalen-1-yl)-3-(3-tert-butyl-1-p-tolyl-1H-pyrazol-5-yl)urea

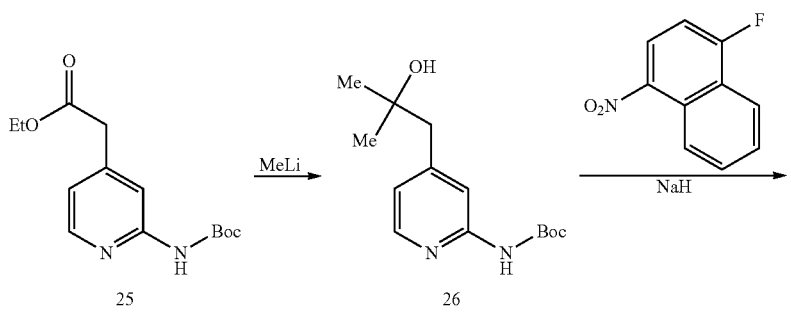

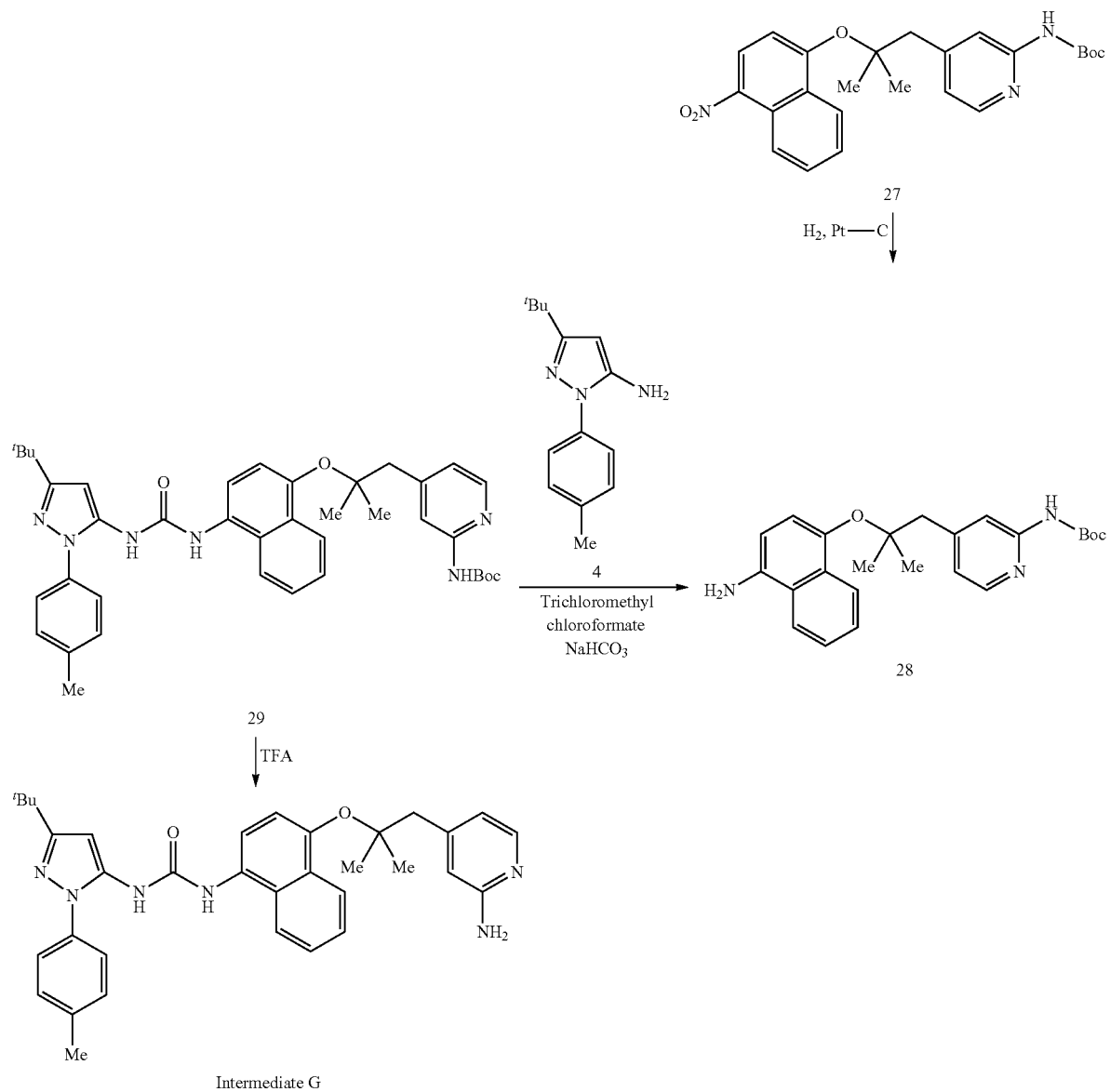

tert-Butyl 4-(2-hydroxy-2-methylpropyl)pyridin-2-ylcarbamate (26)

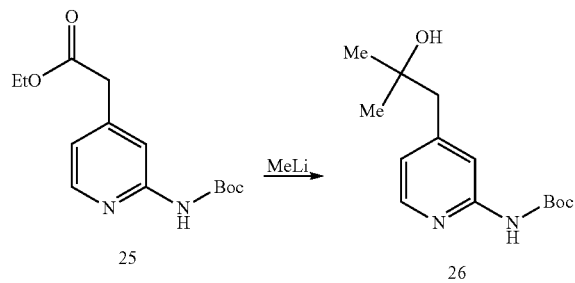

To a solution of ethyl 2-(2-(tert-butoxycarbonylamino)pyridin-4-yl)acetate (25) (WO 2007089512) (1.56 g, 5.58 mmol) in THF (140 mL), at −78° C. under nitrogen, was added methyllithium (1.6 M in diethyl ether, 17.44 ml, 27.9 mmol), over 12 min. The reaction mixture was stirred at −78° C. for 3 hr and the reaction was quenched by the careful addition of 5.0 mL iso-propanol. Water (200 mL) and EtOAc (150 mL) were added, and the layers were separated. The aqueous layer was extracted with EtOAc (100 mL×2) and the combined organic extracts were washed with brine (200 mL), dried and the solvents removed under reduced pressure. The crude material was purified by column chromatography (80 g) eluting with 0 to 80% EtOAc in iso-hexane, to give tert-butyl 4-(2-hydroxy-2-methylpropyl)pyridin-2-ylcarbamate (26) (293 mg, 19%) as a beige powder: m/z 267 (M+H)$^+$ (ES$^+$).

tert-Butyl 4-(2-methyl-2-(4-nitronaphthalen-1-yloxy)propyl)pyridin-2-ylcarbamate (27)

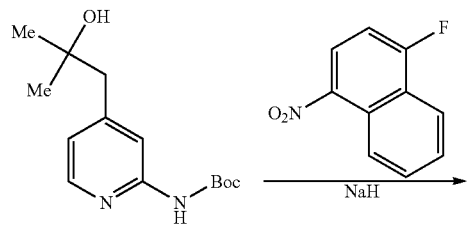

To a stirred solution of tert-butyl 4-(2-hydroxy-2-methylpropyl)pyridin-2-ylcarbamate (26) (292 mg, 1.10 mmol) in DMF (5.0 mL), at 0° C. under nitrogen, was added sodium hydride (132 mg, 3.29 mmol, 60 wt %). The resulting orange mixture was stirred at 0° C. for 45 min, and then a solution of 1-fluoro-4-nitronaphthalene (210 mg, 1.10 mmol) in DMF (5.0 mL) was added dropwise, over 2 min. The dark-brown mixture was stirred at 0° C. for 5 min, and then at RT. After 90 min, the reaction was quenched by addition of 4.0 mL aqueous $Na_4Cl$ solution. Diethyl ether (40 mL), EtOAc (40 mL) and water (40 mL) were added, and the layers separated. The aqueous layer was extracted with a mixture of diethyl ether and EtOAc (1:1, 30 mL×2). The combined organic extracts were washed with brine (50 mL), dried and the solvents removed under reduced pressure. The crude mixture was purified by column chromatography (40 g) eluting with 0 to 70% EtOAc in iso-hexane, to give tert-butyl 4-(2-methyl-2-(4-nitronaphthalen-1-yloxy)propyl)pyridin-2-ylcarbamate (27) (79 mg, 15%) as an orange foam: m/z 438 (M+H)⁺ (ES⁺).

tert-Butyl 4-(2-(4-aminonaphthalen-1-yloxy)-2-methylpropyl)pyridin-2-ylcarbamate (28)

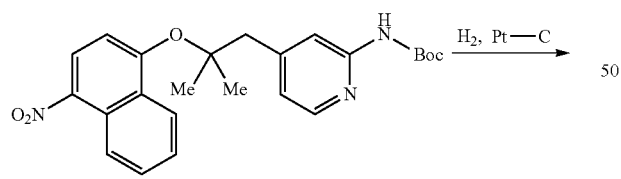

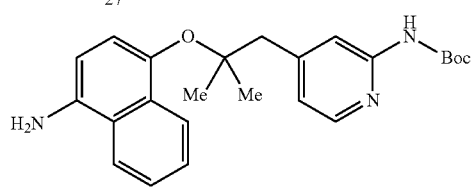

tert-Butyl 4-(2-methyl-2-(4-nitronaphthalen-1-yloxy)propyl)pyridin-2-ylcarbamate (27) (100 mg, 0.229 mmol) in MeOH (30 mL) and AcOH (8.0 mL) was passed through a Thales H-cube (1.0 mL·min⁻¹, 30° C., 55 mm 10% Pt/C Cat-Cart, full hydrogen mode). The volatiles were removed under reduced pressure to give tert-butyl 4-(2-(4-aminonaphthalen-1-yloxy)-2-methylpropyl)pyridin-2-ylcarbamate (28) (92 mg, 99%) as a purple oil: m/z 408 (M+H)⁺ (ES⁺).

tert-Butyl 4-(2-(4-(3-(3-tert-butyl-1-p-tolyl-1H-pyrazol-5-yl)ureido)naphthalen-1-yloxy)-2-methylpropyl)pyridin-2-ylcarbamate (29)

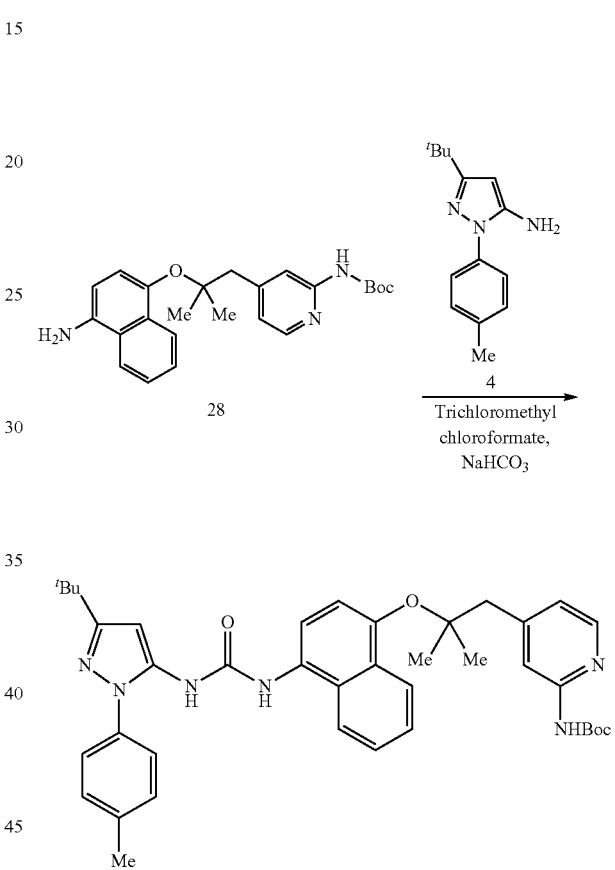

To a solution of 3-tert-butyl-1-p-tolyl-1H-pyrazol-5-amine (4) (WO 2000043384) (250 mg, 1.090 mmol) in DCM (25 mL) was added a saturated solution of aq $NaHCO_3$ (17 mL), and the mixture was stirred vigorously. The mixture was cooled to 0° C. and then trichloromethylchloroformate (395 μl, 3.27 mmol) was added in one portion. The resulting mixture was stirred at 0° C. for 90 min. The layers were then separated, the organic extract was dried and the solvents removed under reduced pressure to afford a brown-orange oil, which was dried under high vacuum, at 30° C. for 30 min. The resulting oil was then taken up in THF (4.0 mL), and was added to tert-butyl 4-(2-(4-aminonaphthalen-1-yloxy)-2-methylpropyl)pyridin-2-ylcarbamate (28) (92 mg, 0.23 mmol).

DIPEA (118 μl, 0.677 mmol) was then added, and the reaction mixture was stirred at RT over 17 hr. Water (15 mL) and EtOAc (15 mL) were added to the purple mixture and the layers separated. The aqueous layer was extracted with EtOAc (10 mL). The combined organic extracts were washed with brine (20 mL), dried and the solvents removed under reduced pressure. The crude material was purified by column chromatography (40 g) eluting with 0 to 50% EtOAc in isohexane, to give tert-butyl 4-(2-(4-(3-(3-tert-butyl-1-p-tolyl-1H-pyrazol-5-yl)ureido)naphthalen-1-yloxy)-2-methylpropyl)pyridin-2-ylcarbamate (29) (24 mg, 14%) as a purple foam: m/z 663 (M+H)$^+$ (ES$^+$).

Intermediate G: 1-(4-(1-(2-aminopyridin-4-yl)-2-methylpropan-2-yloxy)naphthalen-1-yl)-3-(3-tert-butyl-1-p-tolyl-1H-pyrazol-5-yl)urea

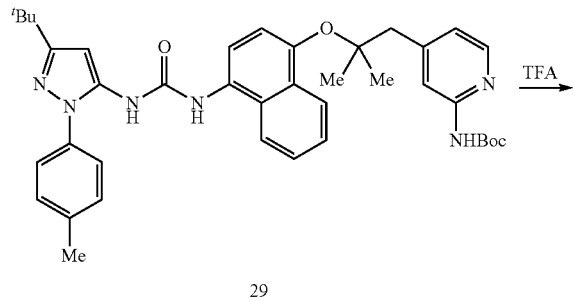

29

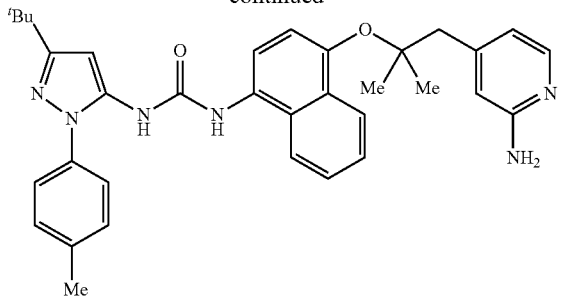

Intermediate G

TFA (1.0 mL) was added to a stirred solution of tert-butyl 4-(2-(4-(3-(3-tert-butyl-1-p-tolyl-1H-pyrazol-5-yl)ureido)naphthalen-1-yloxy)-2-methylpropyl)pyridin-2-ylcarbamate (29) (24.4 mg, 0.031 mmol) in DCM (2.0 mL). The reaction mixture was stirred at 0° C. for a further 15 min, and then at RT. After 2 hr, the solvents were removed under reduced pressure, to leave a dark residue, which was taken back in MeOH (3.0 mL) and then subjected to the SCX capture and release to give 1-(4-(1-(2-aminopyridin-4-yl)-2-methylpropan-2-yloxy)naphthalen-1-yl)-3-(3-tert-butyl-1-p-tolyl-1H-pyrazol-5-yl)urea (Intermediate G) as a purple solid (20 mg, 98%): m/z 563 (M+H)$^+$ (ES$^+$).

Intermediate H: 1-(4-((2-Aminopyrimidin-4-yl)methoxy)naphthalen-1-yl)-3-(3-tert-butyl-1-p-tolyl-1H-pyrazol-5-yl)urea

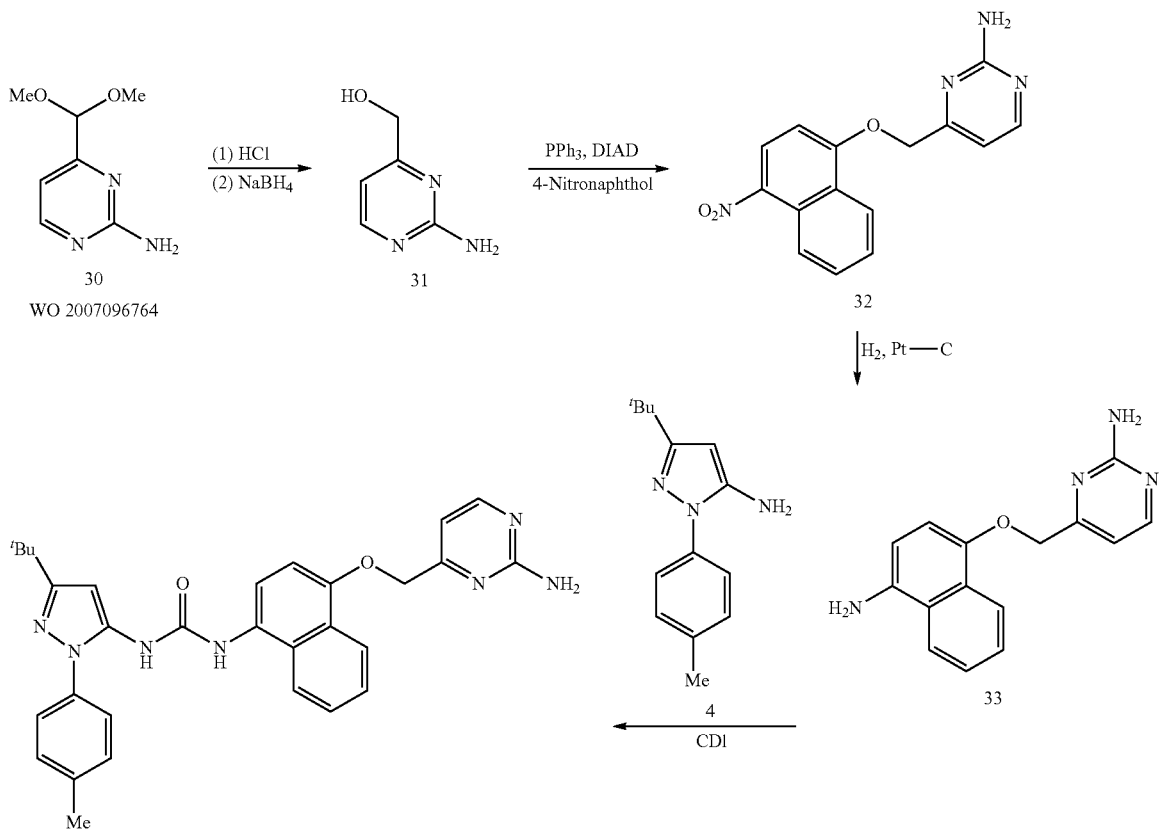

Intermediate H

(2-Aminopyrimidin-4-yl)methanol (31)

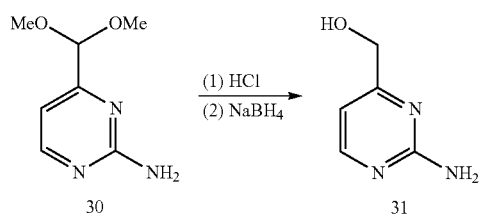

WO 2007096764

Aqueous HCl (2M, 207 mL, 828 mmol) was added to 4-(dimethoxymethyl)pyrimidin-2-amine (30) (WO 2007096764) (14.0 g, 83 mmol). The mixture was placed in a preheated oil bath at 48° C. for 16 hr. The mixture was cooled to RT and neutralized with solid $Na_2CO_3$ which produced a precipitate at pH 7. EtOAc (300 mL) was added, and the solid removed by filtration. After separation of the organic layer, the aqueous layer was extracted with 1% MeOH in THF (4×300 mL). The organics were combined, dried, filtered and evaporated to give crude aldehyde (ca. 4.0 g). This material suspended in MeOH (100 mL), THF (100 mL) and water (100 mL) and treated with $NaBH_4$ (1.565 g, 41.4 mmol). After stirring for 1 hr NaOH (1M, 20 mL) was added and the mixture was allowed to stand at RT for 48 hr. The solvents were evaporated to give a yellow solid which was partitioned between water (50 mL) and EtOAc (100 mL). The solid formed at the interface was removed by filtration and the aqueous layer was extracted with THF (3×300 mL), dried, filtered and evaporated to give a yellow solid. The material was suspended in THF (100 mL) and MeOH (50 mL) and absorbed onto silica gel (20 g) and subjected to column chromatography (80 g) eluting with 15% MeOH in DCM to give (2-aminopyrimidin-4-yl) MeOH (31) as an off-white solid (720 mg, 7%): m/z 126 $(M+H)^+$ $(ES^+)$.

4-((4-Nitronaphthalen-1-yloxy)methyl)pyrimidin-2-amine (32)

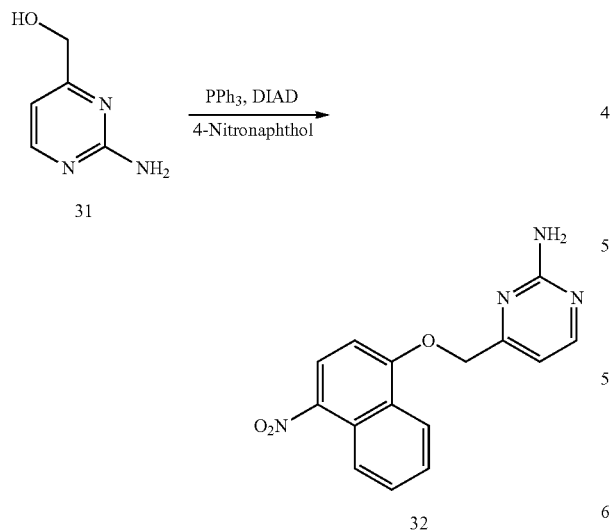

A mixture of 4-nitronaphthol (741 mg, 3.92 mmol), (2-aminopyrimidin-4-yl)methanol (31) (700 mg, 3.92 mmol) and $PPh_3$ (1233 mg, 4.70 mmol) in THF (20 mL) was cooled to −50° C. under nitrogen and was treated dropwise over 5 min with DIAD (996 μl, 4.70 mmol). After completion of the addition, the mixture was allowed to warm to RT and stirred for 1 hr. A yellow precipitate forms during this time. After stirring overnight, the volatiles were evaporated and the residue triturated from MeOH (50 mL). The pale yellow solid collected by filtration and washed with diethyl ether (50 mL) to give 4-((4-nitronaphthalen-1-yloxy)methyl)pyrimidin-2-amine (32) (1.1 g, 93%): m/z 297 $(M+H)^+$ $(ES^+)$.

4-((4-Aminonaphthalen-1-yloxy)methyl)pyrimidin-2-amine (33)

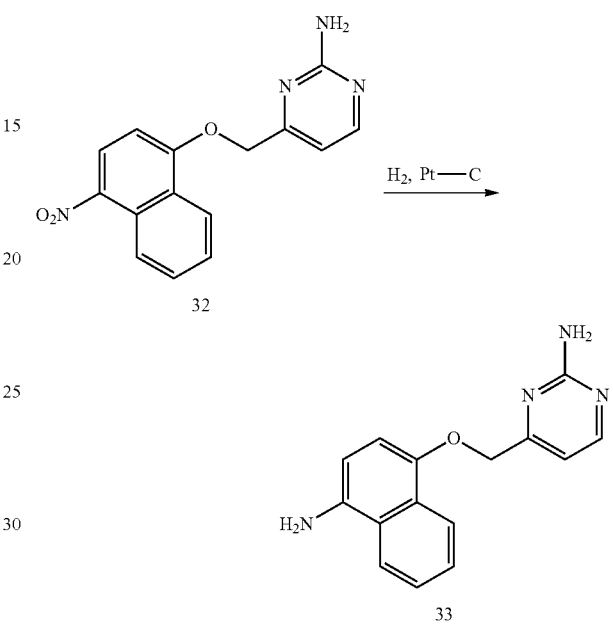

A solution of 4-((4-nitronaphthalen-1-yloxy)methyl)pyrimidin-2-amine (32) (1.10 g, 3.71 mmol) in a DCM (50 mL) and AcOH (40 mL) was passed through a Thales H-cube at 1.0 mL·min$^{-1}$ (full hydrogen mode, 55 mm 10% Pt/C, 40° C.). LC-MS analysis of the solution showed mainly starting material and ca. 20% product. The DCM was evaporated and the solution re-subjected to the above reducing conditions at RT. Analysis showed ca. 70% product together with ca. 20% over reduction and ca. 10% starting material. The volatiles were evaporated to give crude 4-((4-aminonaphthalen-1-yloxy)methyl)pyrimidin-2-amine (33) as a purple solid (0.90 g, 64% yield): m/z 267 $(M+H)^+$ $(ES^+)$.

Intermediate H: 1-(4-((2-Aminopyrimidin-4-yl)methoxy)naphthalen-1-yl)-3-(3-tert-butyl-1-p-tolyl-1H-pyrazol-5-yl)urea

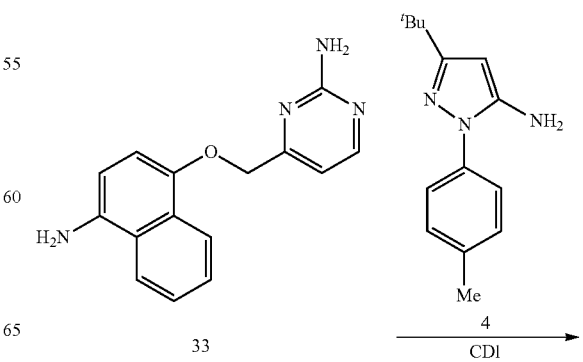

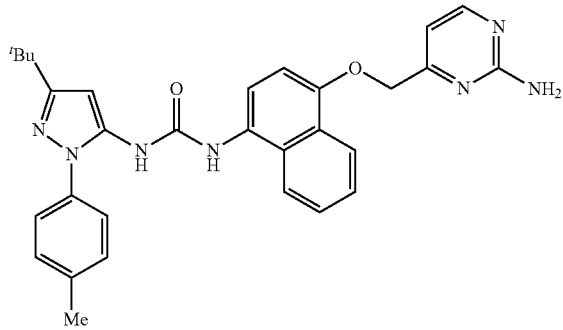

Intermediate H

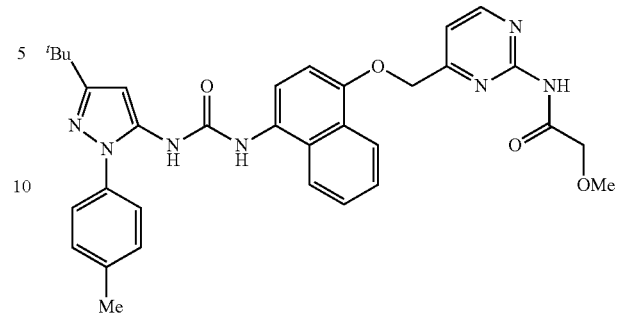

Example 23

A solution of 3-tert-butyl-1-p-tolyl-1H-pyrazol-5-amine (4) (WO 2000043384) (0.98 g, 4.26 mmol) in DCM (4.0 mL) was added dropwise over 1 hr, to a suspension of CDI (0.69 g, 4.26 mmol) in DCM (3.0 mL) and the solution was stirred at RT for 2 hr. This solution was added dropwise to a solution of 4-((4-aminonaphthalen-1-yloxy)methyl)pyrimidin-2-amine (33) (0.9 g, 2.366 mmol) in DCM (10 mL). After each 1.0 mL aliquot was added, the reaction was allowed to stir for 1 hr, and the mixture monitored by LC-MS to ensure consumption of the CDI activated 3-tert-butyl-1-p-tolyl-1H-pyrazol-5-amine, without over acylation. The reaction was quenched with MeOH (20 mL), silica added (20 g) and the volatiles evaporated. The residue was subjected to column chromatography (100 g) eluting with 50 to 100% EtOAc in iso-hexane. The combined fractions were triturated from DCM (20 mL) and the solid collected, and washed with diethyl ether (50 mL) to give 1-(4-((2-aminopyrimidin-4-yl)methoxy)naphthalen-1-yl)-3-(3-tert-butyl-1-p-tolyl-1H-pyrazol-5-yl)urea (Intermediate H) as a purple solid (0.48 g, 38%): m/z 523 (M+H)$^+$ (ES$^+$).

EXAMPLE 23

N-(4-((4-(3-(3-tert-Butyl-1-p-tolyl-1H-pyrazol-5-yl)ureido)naphthalen-1-yloxy)methyl)pyrimidin-2-yl)-2-methoxyacetamide A suspension of 1-(4-((2-aminopyrimidin-4-yl)methoxy)naphthalen-1-yl)-3-(3-tert-butyl-1-p-tolyl-1H-pyrazol-5-yl)urea (Intermediate H) (52 mg, 0.100 mmol) in DCM (1.0 mL) and DMF (100 µl) was treated with methoxyacetyl chloride (27 µl, 0.299 mmol) followed by DIPEA (52 µl, 0.299 mmol). After stirring overnight at RT, the volatiles were evaporated and the residue suspended in a mixture of MeOH (2.0 mL) and AcOH (2.0 mL). The suspension was subjected to SCX capture and release. Very little material eluted off hence the SCX from the cartridge was removed and extracted with MeOH (50 mL). After evaporation, an off white solid was obtained and this was triturated from MeOH (1.0 mL) and diethyl ether (5.0 mL) to give N-(4-((4-(3-(3-tert-butyl-1-p-tolyl-1H-pyrazol-5-yl)ureido)naphthalen-1-yloxy)methyl)pyrimidin-2-yl)-2-methoxy acetamide (Example 23) as a white solid (12 mg, 19% yield): m/z 594 (M+H)$^+$ (ES$^+$). $^1$H NMR (400 MHz, DMSO-d$_6$) δ: 1.27 (9H, s), 2.40 (3H, s), 3.34 (3H, s), 4.24 (2H, s), 5.34 (2H, s), 6.35 (1H, s), 7.02 (1H, d), 7.35 (2H, d), 7.44 (3H, m), 7.60 (3H, m), 7.95 (1H, m), 8.36 (1H, m), 8.59 (1H, br s), 8.68 (1H, d), 8.80 (1H, br s), 10.44 (1H, br s).

Intermediate I: 1-(4-(2-(4-Amino-1H-imidazol-1-yl)ethoxy)naphthalen-1-yl)-3-(3-tert-butyl-1-p-tolyl-1H-pyrazol-5-yl)urea

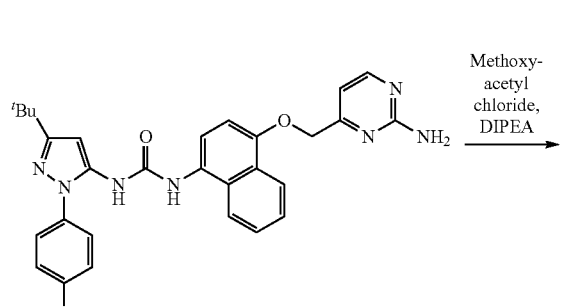

Intermediate H

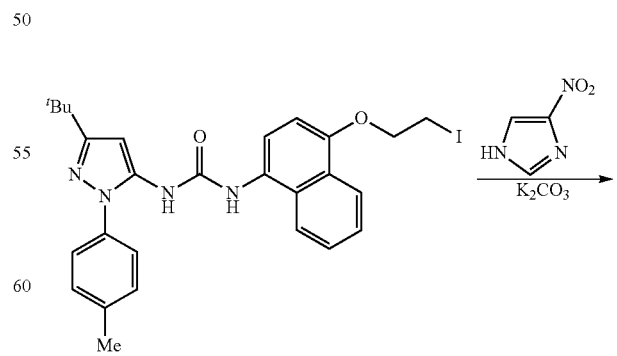

34
J. Med. Chem., 2003, 46, 4676-4686

A mixture of 1-(3-tert-butyl-1-p-tolyl-1H-pyrazol-5-yl)-3-(4-(2-iodoethoxy)naphthalen-1-yl)urea (*J. Med. Chem.*, 2003, 46, 4676-4686) (400 mg, 0.704 mmol), potassium carbonate (292 mg, 2.111 mmol) and 4-nitroimidazole (88 mg, 0.774 mmol) in DMF (2.0 mL) was placed in a pre-heated oil bath at 50° C. and stirred for 16 hr. The mixture was cooled to RT, poured into water (5.0 mL) and extracted with EtOAc (5.0 mL×2). The combined organic layers were dried, filtered and evaporated and the resulting residue was subjected to column chromatography (40 g), eluting with EtOAc to give 1-(3-tert-butyl-1-p-tolyl-1H-pyrazol-5-yl)-3-(4-(2-(4-nitro-1H-imidazol-1-yl)ethoxy)naphthalen-1-yl)urea (35) as a brown solid (276 mg, 60%): m/z 554 (M+H)⁺ (ES⁺).

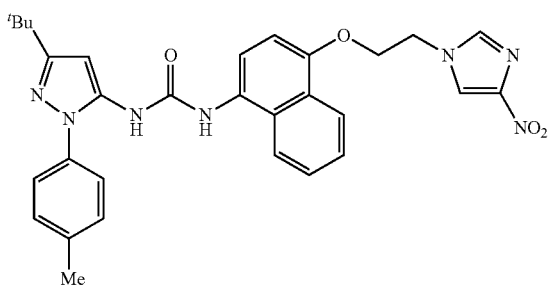

35

↓ H₂, Pt—C

Intermediate I: 1-(4-(2-(4-Amino-1H-imidazol-1-yl)ethoxy)naphthalen-1-yl)-3-(3-tert-butyl-1-p-tolyl-1H-pyrazol-5-yl)urea

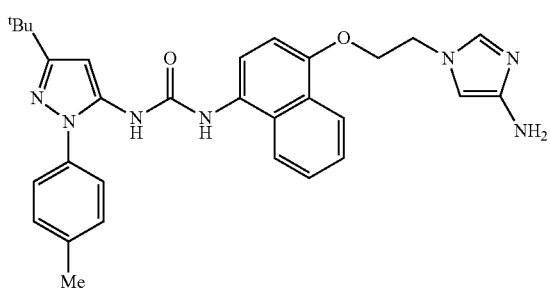

Intermediate I 1-(3-tert-Butyl-1-p-tolyl-1H-pyrazol-5-yl)-3-(4-(2-(4-nitro-1H-imidazol-1-yl)ethoxy)naphthalen-1-yl)urea (35)

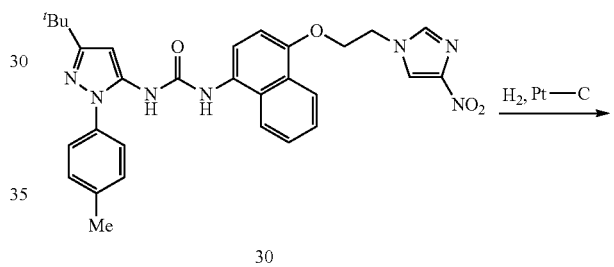

30

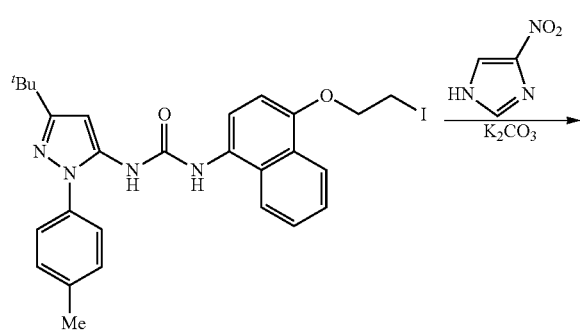

34

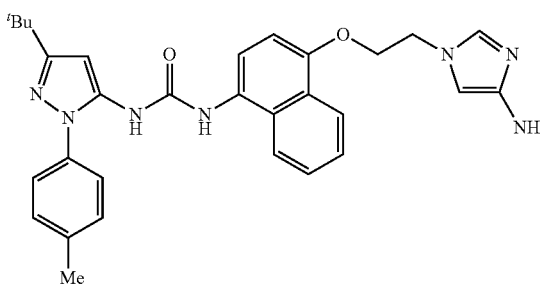

Intermediate I

A solution of 1-(3-tert-butyl-1-p-tolyl-1H-pyrazol-5-yl)-3-(4-(2-(4-nitro-1H-imidazol-1-yl)ethoxy)naphthalen-1-yl)urea (30) (158 mg, 0.253 mmol) in DCM/MeOH/AcOH (1:1:2, 6.0 mL) was passed through a Thales H-cube (10% Pt/C Cat-Cart., 30 mm) at 1.0 ml·min⁻¹ in full hydrogen mode at 50° C. The solvents were evaporated under reduced pressure to give 1-(4-(2-(4-amino-1H-imidazol-1-yl)ethoxy)naphthalen-1-yl)-3-(3-tert-butyl-1-p-tolyl-1H-pyrazol-5-yl)urea (Intermediate I) as a light brown oil (150 mg, 100%): m/z 524 (M+H)⁺ (ES⁺).

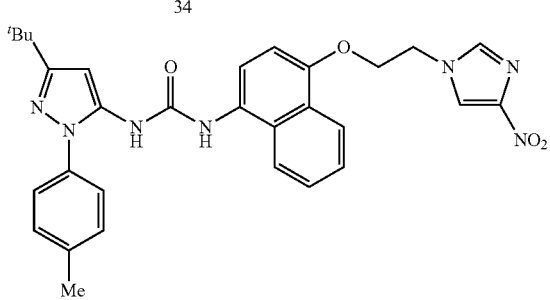

35

EXAMPLE 24

N-(1-(2-(4-(3-(3-tert-butyl-1-p-tolyl-1H-pyrazol-5-yl)ureido)naphthalen-1-yloxy)ethyl)-1H-imidazol-4-yl)-2-methoxyacetamide

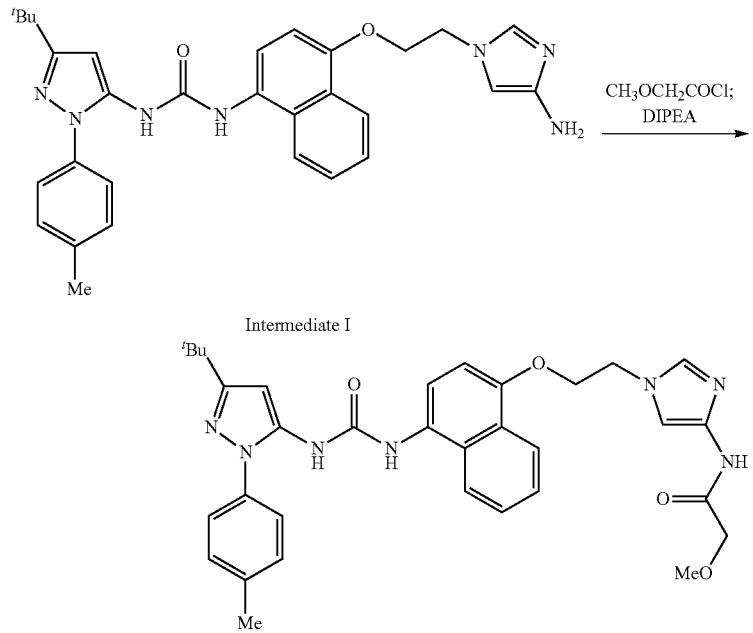

Example 24

To a suspension of 1-(4-(2-(4-amino-1H-imidazol-1-yl)ethoxy)naphthalen-1-yl)-3-(3-tert-butyl-1-p-tolyl-1H-pyrazol-5-yl)urea (Intermediate I) (50 mg, 0.095 mmol) in DCM (2.0 mL) was added DIPEA (33 µl, 0.191 mmol) and 2-methoxyacetyl chloride (10 µl, 0.105 mmol). The mixture was stirred at RT overnight and then partitioned between saturated aq NaHCO$_3$ solution (5.0 mL) and DCM (2.0 mL). The layers were separated through a phase separator cartridge and the organics were collected and evaporated under reduced pressure. The resulting residue was subjected to SCX capture and release and column chromatography (12 g), eluting with 0 to 10% MeOH in EtOAc. Trituration with EtOAc (5.0 mL) gave N-(1-(2-(4-(3-(3-tert-butyl-1-p-tolyl-1H-pyrazol-5-yl)ureido) naphthalen-1-yloxy)ethyl)-1H-imidazol-4-yl)-2-methoxyacetamide (Example 24) as a white solid (8 mg, 14%): m/z 596 (M+H)$^+$ (ES$^+$). $^1$H NMR (400 MHz, DMSO-d$_6$) δ: 1.26 (9H, s), 2.38 (3H, s), 3.29 (3H, s), 3.93 (2H, s), 4.37 (2H, t), 4.47 (2H, t), 6.34 (1H, s), 6.93 (1H, d), 7.34 (2H, m), 7.41-7.45 (3H, m), 7.48-7.62 (4H, m), 7.88 (1H, d), 8.13-8.15 (1H, dd), 8.54 (1H, s), 8.75 (1H, s), 9.84 (1H, s).

Biological Testing

All compound examples demonstrated EC$_{50}$ values of less than 1 µM versus LPS-induced TNFα release in differentiated U937 cells (see below for assay details). Summaries of the properties of Example 1 established using both in vitro and in vivo assays are presented below.

In Vitro Testing for Example 1

| Enzyme IC$_{50}$ (nM) | | Differentiated U937 cells LPS-induced TNFα release | | THP1 cells LPS-induced |
|---|---|---|---|---|
| Alpha subtype | Gamma subtype | EC$_{50}$ (nM)[1] | MTT Assay 4, 24 h (10 µg/ml) | TNFα release IC$_{50}$ (nM) |
| 5.3 | 402 | 0.88 | Negative[2] | 2.3 |

[1]50% effective concentration relative to the effect of 10 µg/ml BIRB796 (as 100%).
[2]no significant toxic effect observed in MTT assay A description of these assays is as follows:

Enzyme Inhibition Assay

The enzyme inhibitory activity of compound was determined by fluorescence resonance energy transfer (FRET) using synthetic peptides labelled with both donor and acceptor fluorophores (Z-LYTE, Invitrogen). Briefly, recombinant, phosphorylated p38 MAPK gamma (MAPK12: Millipore) was diluted in HEPES buffer, mixed with compound at desired final concentrations and incubated for two hours at room temperature. The FRET peptide (2 uM) and ATP (100 uM) were next added to the enzyme/compound mixture and incubated for one hour. Development reagent (protease) was added for one hour prior to detection in a fluorescence microplate reader. The site-specific protease only cleaves non-phosphorylated peptide and eliminates the FRET signal. Phosphorylation levels of each reaction were calculated using the ratio of coumarin emission (donor) over fluorescein emission (acceptor) with high ratios indicating high phosphorylation and low ratios, low phosphorylation levels. The percentage inhibition of each reaction was calculated relative to non-inhibited control, and the 50% inhibitory concentration (IC$_{50}$ value) then calculated from the concentration-response curve.

For p38 MAPK alpha (MAPK14: Invitrogen), enzyme activity was evaluated indirectly by determining activation/phosphorylation of the down-stream molecule, MAPKAP-K2. The p38 MAPK α protein was mixed with its inactive target MAPKAP-K2 (Invitrogen) and compound for two hours at room temperature. The FRET peptide (2 uM), which is a phosphorylation target for MAPKAP-K2, and ATP (10 uM) were then added to the enzymes/compound mixture and incubated for one hour. Development reagent was then added and the mixture incubated for one hour before detection by fluorescence completed the assay protocol.

LPS-Induced TNF Alpha Release in U937 Cells: Potency

U937 cells, human monocytic cell line, were differentiated to macrophage-type cells by incubation with phorbol myristate acetate (PMA; 100 ng/ml) for 48 to 72 hours. Where appropriate, cells were pre-incubated with final concentrations of compound for 2 hrs. Cells were then stimulated with 0.1 ug/ml of LPS (from *E. Coli*: O111:B4, Sigma) for 4 hrs, and the supernatant collected for determination of TNFα concentration by sandwich ELISA (Duo-set, R&D systems). THP-1, human monocytic cell line, was also used for this assay. THP-1 cells were stimulated with 1 ug/ml of LPS (from *E. Coli*: O111:B4, Sigma) for 4 hrs, and the supernatant collected for determination of TNFα concentration. The inhibition of TNFα production was calculated as a percentage of that achieved by 10 µg/ml of BIRB796 at each concentration of test compound by comparison with vehicle control. The 50% effective concentration (EC$_{50}$) was determined from the resultant concentration-response curve.

LPS-Induced TNF Alpha Release in THP-1 Cells: Potency

THP-1 cells, a human monocytic cell line, were stimulated with 1 µg/ml of LPS (from *E. Coli*; O111:B4, Sigma) for 4 hr and the supernatant collected for determination of TNFα concentration by sandwich ELISA (Duo-set, R&D systems). The inhibition of TNFα production was calculated at each concentration by comparison with vehicle control. The 50% inhibitory concentration (IC$_{50}$) was determined from the resultant concentration-response curve.

MTT Assay

Differentiated U937 cells were pre-incubated with compound for 4 hrs in 5% FCS or 10% FCS for 24 hrs and 72 hr. The supernatant was replaced with 200 ul of new media and 10 ul of MTT stock solution (5 mg/ml) added to each well. After 1 hr incubation, the media were removed, 200 ul of DMSO added to each well and the plates were shaken lightly for 1 h prior to reading the absorbance at 550 nm.

The percentage loss of cell viability was calculated for each well relative to vehicle (0.5% DMSO)-treatment. Consequently an apparent increase in cell viability for drug treatment relative to vehicle is tabulated as a negative percentage.

In Vivo Testing for Example 1

LPS-Induced Neutrophilia in the Mouse: Duration of Action

Non-fasted mice were dosed by the intra tracheal route with either vehicle, or the test substance at the time points ("pre-dose") indicated with respect to the start of LPS treatment. At T=0, mice were placed into an exposure chamber and exposed to LPS. Eight hours after LPS challenge, animals were under anesthetized, the trachea cannulated and BALF extracted by infusing and withdrawing 1 ml of PBS into the lungs via a tracheal catheter. Total and differential white cell counts in the BALF samples were measured using a Neubaur haemocytometer. Cytospin smears of the BALF samples were prepared by centrifugation at 200 rpm for 5 min at room temperature and stained using a DiffQuik stain system (Dade Behring). Cells were counted using oil immersion microscopy.

The results are shown in FIGS. 1 and 2. Data for neutrophil numbers is reported as total and differential number (test substance relative to vehicle) of cells per mL of BALF, mean±S.E.M. (n=8).

SUMMARY

The biological studies in vitro show that the compound of Example 1 is a potent inhibitor of p38 MAP kinase subtypes alpha and gamma with good efficacy in an in vitro model of anti-inflammatory activity (LPS-induced TNFalpha release from differentiated U937 cells and THP-1 cells). From the MTT results it may be concluded that the compound does not exhibit overt cellular toxicity at the concentrations used.

The biological studies in vivo show that the compound of Example 1 is effective in inhibiting LPS-induced neutrophil accumulation in an animal model, with a long duration of effect as shown by the significant inhibition even at 12 or more hours of pre-dosing.

Throughout the specification and the claims which follow, unless the context requires otherwise, the word 'comprise', and variations such as 'comprises' and 'comprising', will be understood to imply the inclusion of a stated integer, step, group of integers or group of steps but not to the exclusion of any other integer, step, group of integers or group of steps.

All patents and patent applications referred to herein are incorporated by reference in their entirety.

The application of which this description and claims forms part may be used as a basis for priority in respect of any subsequent application. The claims of such subsequent application may be directed to any feature or combination of features described herein. They may take the form of product, composition, process, or use claims and may include, by way of example and without limitation, the claims.

The invention claimed is:
1. A compound of formula (I)

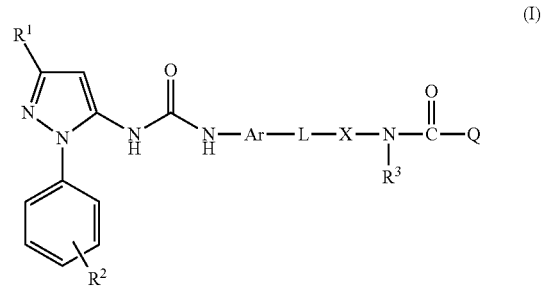

wherein R$^1$ is C$_{1-6}$ alkyl optionally substituted by a hydroxyl group;
R$^2$ is H or C$_{1-6}$ alkyl optionally substituted by a hydroxyl group;
R$^3$ is H, C$_{1-6}$ alkyl or C$_{0-3}$ alkylC$_{3-6}$ cycloalkyl,
Ar is a naphthyl or a phenyl ring either of which may be optionally substituted by one or more groups independently selected from C$_{1-6}$ alkyl, C$_{1-6}$ alkoxy, amino, C$_{1-4}$ mono or di-alkyl amino;
L is a saturated or unsaturated branched or unbranched C$_{1-8}$ alkylene chain, wherein one or more carbons are optionally replaced by —O— and the chain is optionally substituted by one or more halogen atoms,
X is 5 or 6 membered heteroaryl group containing at least one nitrogen atom and optionally including 1 or 2 further heteroatoms selected from O, S and N;

Q is selected from:
a) a saturated or unsaturated, branched or unbranched $C_{1-10}$ alkyl chain, wherein at least one carbon (for example 1, 2 or 3 carbons) is replaced by a heteroatom selected from O, N, $S(O)_p$, wherein said chain is optionally, substituted by one or more groups selected from oxo, halogen, an aryl group, a heteroaryl group or an heterocyclyl group, each aryl, heteroaryl or heterocyclyl group bearing 0 to 3 substituents selected from halogen, $C_{1-6}$ alkyl, $C_{1-6}$ alkoxy, $C_{1-6}$ haloalkyl, amino, $C_{1-4}$ mono or di-alkyl amino,
with the proviso that the atom linked directly to the carbonyl in —$NR^3C(O)$— is not an oxygen or a sulfur atom; and
b) a $C_{0-8}$ alkyl$C_{5-6}$ heterocyclyl said heterocyclyl group comprising at least one heteroatom selected from O, N and S, and optionally substituted by one or two or three groups independently selected from halogen $C_{1-6}$ alkyl, $C_{1-6}$ alkoxy, $C_{1-6}$ haloalkyl, amino, $C_{1-4}$ mono and di-alkyl amino; and
p is 0, 1 or 2;
or a pharmaceutically acceptable salt or solvate thereof, including
all stereoisomers and tautomers thereof.

2. A compound of formula (I) according to claim 1, wherein Ar is napthyl.

3. A compound of formula (I) according to claim 1, wherein $R^1$ is tert-butyl.

4. A compound of formula (I) according to claim 1, wherein $R^2$ is methyl.

5. A compound of formula (I) according to claim 1, wherein $R^2$ is in the para position.

6. A compound of formula (I) according to claim 1, wherein L represents —$(CH_2)_n$—$O(CH_2)_m$— wherein n and m are independently 0, 1, 2, 3, 4, 5, 6 or 7, with the proviso that n+m is zero or an integer from 1 to 7.

7. A compound of formula (I) according to claim 1, wherein $R^3$ is H.

8. A compound of formula (I) according to claim 1, wherein Q is selected from: —$NR^3C(O)CH_2OC_{1-6}$ alkyl, —$NR^3C(O)CH_2O(CH_2)_2OCH_3$, —$NR^3C(O)CH(CH_3)OCH_3$, —$NR^3C(O)CH_2NHCH_3$, —$NR^3C(O)CH_2NHCH_2CH_2OCH_3$, —$NR^3C(O)CH_2SCH_3$, —$NR^3C(O)NH_2$, —$NR^3C(O)CH_2S(O)_2CH_3$, —$NR^3C(O)NHC_{1-7}$ alkyl, —$NR^3C(O)N(C_{1-4}$ alkyl)$C_{1-5}$ alkyl, and —$NR^3C(O)CHN[(CH_2)_2OCH_3]_2$.

9. A compound of formula (I) according to claim 8, wherein Q is selected from: —$NHC(O)CH_2OCH_3$; —$NHC(O)CH_2O(CH_2)_2OCH_3$; —$NHC(O)CH(CH_3)OCH_3$; —$NHC(O)CH_2NHCH_3$; —$NHC(O)CH_2NH(CH_2)_2OCH_3$; —$NHC(O)CH_2SCH_3$; —$NHC(O)NH_2$; —$NHC(O)CH_2S(O)_2CH_3$; —$NHC(O)NHCH_3$; —$NHC(O)N(CH_3)_2$; and —$NHC(O)CHN[(CH_2)_2OCH_3]_2$.

10. A compound of formula (I) according to claim 1, wherein the compound is of formula (IA)

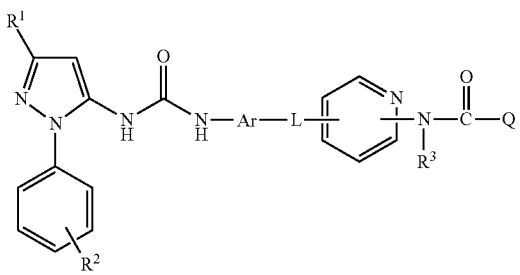

(IA)

or a pharmaceutically acceptable salt or solvate thereof, including all stereoisomers and tautomers thereof.

11. A compound of formula (I) according to claim 10, wherein the compound is of formula (IB)

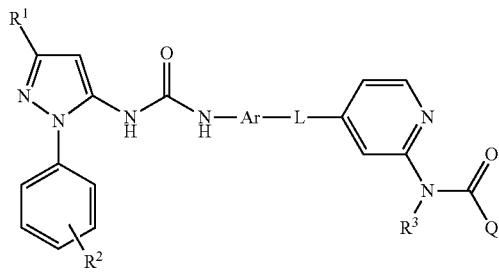

(IB)

or a pharmaceutically acceptable salt or solvate thereof, including all stereoisomers and tautomers thereof.

12. A compound of formula (I) according claim 1, wherein the compound is of formula (IC)

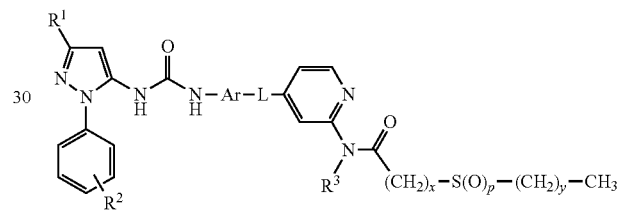

(IC)

wherein x is an integer from 1 to 6 and y is zero or an integer from 1 to 5 with proviso that x+y is an integer from 1 to 6, for example x is 1 and y is 1 or a pharmaceutically acceptable salt or solvate thereof, including all stereoisomers and tautomers thereof.

13. A compound of formula (I) according to claim 1, wherein the compound is of formula (ID)

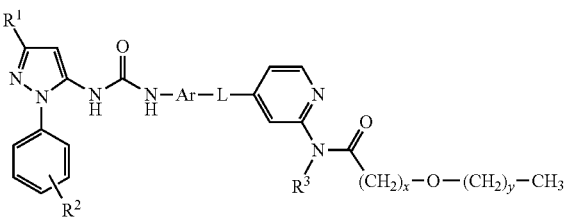

(ID)

wherein x is an integer from 1 to 6 and y is zero or an integer from 1 to 5, with the proviso that x+y is an integer from 1 to 6, for example x is 1 and y is 0 or a pharmaceutically acceptable salt or solvate thereof, including all stereoisomers and tautomers thereof.

14. A compound of formula (I) according to claim 1, wherein the compound is selected from:
N-(4-((4-(3-(3-tert-Butyl-1-p-tolyl-1H-pyrazol-5-yl)ureido)naphthalen-1-yloxy)methyl)pyridin-2-yl)-2-methoxyacetamide;
Methyl 4-((4-(3-(3-tert-butyl-1-p-tolyl-1H-pyrazol-5-yl)ureido)naphthalen-1-yloxy)methyl)pyridin-2-ylurea;

N-(4-((4-(3-(3-tert-Butyl-1-p-tolyl-1H-pyrazol-5-yl)ureido)naphthalen-1-yloxy)methyl)pyridin-2-yl)tetrahydro-2H-pyran-4-carboxamide;
(S)—N-(4-((4-(3-(3-tert-Butyl-1-p-tolyl-1H-pyrazol-5-yl)ureido)naphthalen-1-yloxy)methyl)pyridin-2-yl)-2-methoxypropanamide;
(R)—N-(4-((4-(3-(3-tert-Butyl-1-p-tolyl-1H-pyrazol-5-yl)ureido)naphthalen-1-yloxy)methyl)pyridin-2-yl)-2-methoxypropanamide;
N-(4-((4-(3-(3-tert-Butyl-1-p-tolyl-1H-pyrazol-5-yl)ureido)naphthalen-1-yloxy)methyl)pyridin-2-yl)-2-(methylthio)acetamide;
N-(4-((4-(3-(3-tert-Butyl-1-p-tolyl-1H-pyrazol-5-yl)ureido)naphthalen-1-yloxy)methyl)pyridin-2-yl)-2-morpholinoacetamide;
N-(4-((4-(3-(3-tert-Butyl-1-p-tolyl-1H-pyrazol-5-yl)ureido)naphthalen-1-yloxy)methyl)pyridin-2-yl)-2-(pyrrolidin-1-yl)acetamide;
N-(4-((4-(3-(3-tert-Butyl-1-p-tolyl-1H-pyrazol-5-yl)ureido)naphthalen-1-yloxy)methyl)pyridin-2-yl)-2-(4-methylpiperazin-1-yl)acetamide;
N-(4-((4-(3-(3-tert-Butyl-1-p-tolyl-1H-pyrazol-5-yl)ureido)naphthalen-1-yloxy)methyl)pyridin-2-yl)-2-(4-(2-methoxyethyl)piperazin-1-yl)acetamide;
N-(4-((4-(3-(3-tert-Butyl-1-p-tolyl-1H-pyrazol-5-yl)ureido)naphthalen-1-yloxy)methyl)pyridin-2-yl)-2-(2-methoxyethylamino)acetamide;
N-(4-((4-(3-(3-tert-Butyl-1-p-tolyl-1H-pyrazol-5-yl)ureido)naphthalen-1-yloxy)methyl)pyridin-2-yl)-2-(dimethylamino)acetamide;
N-(4-((4-(3-(3-tert-Butyl-1-p-tolyl-1H-pyrazol-5-yl)ureido)naphthalen-1-yloxy)methyl)pyridin-2-yl)-2-(methylamino)acetamide;
N-(4-((4-(3-(3-tert-Butyl-1-p-tolyl-1H-pyrazol-5-yl)ureido)naphthalen-1-yloxy)methyl)pyridin-2-yl)-2-((4-methoxybenzyl)(methyl)amino)acetamide;
1-(4-((3-Methylureidopyridin-4-yl)methoxy)naphthalen-1-yl)-3-(3-tert-butyl-1-p-tolyl-1H-pyrazol-5-yl)urea;
N-(4-((4-(3-(3-tert-Butyl-1-p-tolyl-1H-pyrazol-5-yl)ureido)naphthalen-1-yloxy)methyl)pyridin-3-yl)-2-methoxyacetamide;
N-(4-((4-(3-(3-tert-Butyl-1-p-tolyl-1H-pyrazol-5-yl)ureido)naphthalen-1-yloxy)methyl)pyridin-3-yl)-2-(2-methoxyethoxy)acetamide;
N-(4-(2-(4-(3-(3-tert-Butyl-1-p-tolyl-1H-pyrazol-5-yl)ureido)naphthalen-1-yloxy)ethyl)pyridin-2-yl)-2-methoxyacetamide;
N-(4-(2-(4-(3-(3-tert-Butyl-1-p-tolyl-1H-pyrazol-5-yl)ureido)naphthalen-1-yloxy)ethyl)pyridin-2-yl)-2-(2-methoxyethoxy)acetamide;
4-(2-(4-(3-(3-tert-Butyl-1-p-tolyl-1H-pyrazol-5-yl)ureido)naphthalen-1-yloxy)ethyl)-1-methyl-3-(pyridin-2-yl)urea;
4-(2-(4-(3-(3-tert-Butyl-1-p-tolyl-1H-pyrazol-5-yl)ureido)naphthalen-1-yloxy)ethyl)-3-(pyridin-2-yl)urea;
N-(4-(2-(4-(3-(3-tert-Butyl-1-p-tolyl-1H-pyrazol-5-yl)ureido)naphthalen-1-yloxy)ethyl)pyridin-3-yl)-2-(2-methoxyethoxy)acetamide;
N-(4-((4-(3-(3-tert-Butyl-1-p-tolyl-1H-pyrazol-5-yl)ureido)naphthalen-1-yloxy)methyl)pyrimidin-2-yl)-2-methoxyacetamide; or
N-(1-(2-(4-(3-(3-tert-butyl-1-p-tolyl-1H-pyrazol-5-yl)ureido)naphthalen-1-yloxy)ethyl)-1H-imidazol-4-yl)-2-methoxyacetamide.

15. A pharmaceutical composition comprising a compound according to claim 1 in combination with one or more pharmaceutically acceptable diluents or carriers.

16. A method of treatment of a condition selected from the group consisting of COPD, asthma, paediatric asthma, cystic fibrosis, sarcoidosis, idiopathic pulmonary fibrosis, allergic rhinitis, rhinitis, sinusitis, allergic conjunctivitis, conjunctivitis, allergic dermatitis, contact dermatitis, psoriasis, ulcerative colitis, inflamed joints secondary to rheumatoid arthritis or osteoarthritis, rheumatoid arthritis, pancreatitis, and cachexia,
which comprises administering to a subject in need thereof an effective amount of a compound of formula (I) according to claim 1.

17. A method of treatment of a condition selected from the group consisting of COPD, asthma, paediatric asthma, cystic fibrosis, sarcoidosis, idiopathic pulmonary fibrosis, allergic rhinitis, rhinitis, sinusitis, allergic conjunctivitis, conjunctivitis, allergic dermatitis, contact dermatitis, psoriasis, ulcerative colitis, inflamed joints secondary to rheumatoid arthritis or osteoarthritis, rheumatoid arthritis, pancreatitis, and cachexia,
which comprises administering to a subject in need thereof an effective amount of a pharmaceutical composition according to claim 15.

18. A method according to claim 16, wherein the condition is selected from the group consisting of
COPD, asthma, paediatric asthma, cystic fibrosis and allergic rhinitis.

19. A method according to claim 17, wherein the condition is selected from the group amended) consisting of
COPD, asthma, paediatric asthma, cystic fibrosis and allergic rhinitis.

* * * * *